United States Patent
Jung et al.

(10) Patent No.: US 12,195,543 B2
(45) Date of Patent: Jan. 14, 2025

(54) ANTI-FLT₃ ANTIGEN BINDING PROTEINS

(71) Applicants: DEUTSCHES KREBSFORSCHUNGSZENTRUM STIFTUNG DES OFFENTLICHEN RECHTS, Heidelberg (DE); EBERHARD KARLS UNIVERSITAT TUBINGEN, Tubingen (DE)

(72) Inventors: Gundram Jung, Rottenburg (DE); Helmut Salih, Tubingen (DE); Fabian Vogt, Neu-Ulm (DE); Latifa Zekri-Metref, Tubingen (DE); Martin Pflügler, Tubingen (DE); Isabelle Ehnes, Tubingen (DE)

(73) Assignees: DEUTSCHES KREBSFORSCHUNGSZENTRUM STIFTUNG DES OFFENTLICHEN RECHTS (DE); EBERHARD KARLS UNIVERSITAT TUBINGEN (DE)

( * ) Notice: Subject to any disclaimer, the term of this patent is extended or adjusted under 35 U.S.C. 154(b) by 781 days.

(21) Appl. No.: 17/275,647

(22) PCT Filed: Sep. 11, 2019

(86) PCT No.: PCT/EP2019/074268
§ 371 (c)(1),
(2) Date: Mar. 11, 2021

(87) PCT Pub. No.: WO2020/053300
PCT Pub. Date: Mar. 19, 2020

(65) Prior Publication Data
US 2022/0056141 A1    Feb. 24, 2022

(30) Foreign Application Priority Data

Sep. 11, 2018 (EP) .................................. 18193889
Aug. 1, 2019 (EP) .................................. 19189566

(51) Int. Cl.
C07K 16/28    (2006.01)
A61K 39/00   (2006.01)
(Continued)

(52) U.S. Cl.
CPC .......... *C07K 16/2863* (2013.01); *A61P 35/02* (2018.01); *C07K 16/2809* (2013.01);
(Continued)

(58) Field of Classification Search
None
See application file for complete search history.

(56) References Cited

U.S. PATENT DOCUMENTS 5,500,362 A    3/1996  Robinson et al.
5,821,337 A    10/1998 Carter et al.
(Continued)

FOREIGN PATENT DOCUMENTS

EP    2155788 B1   6/2012
EP    2155783 B2   7/2013
(Continued)

OTHER PUBLICATIONS

Compete. Merriam Webster. https://www.merriam-webster.com/dictionary/compete. Accessed online Feb. 22, 2024 (Year: 2024).*
(Continued)

*Primary Examiner* — Daniel E Kolker
*Assistant Examiner* — Hilary Ann Petrash
(74) *Attorney, Agent, or Firm* — McAndrews, Held & Malloy, Ltd.

(57) ABSTRACT

The present invention provides novel human fins related tyrosine kinase 3 (FLT₃) antigen binding proteins, such as antibodies, having improved FLT₃ binding affinity, and/or anti-tumor activity. The FLT₃ antibodies of the invention were generated by mutation of a parent FLT₃ antibody and tested in in vitro in binding assays as well as in vivo in a
(Continued)

Figure 1:
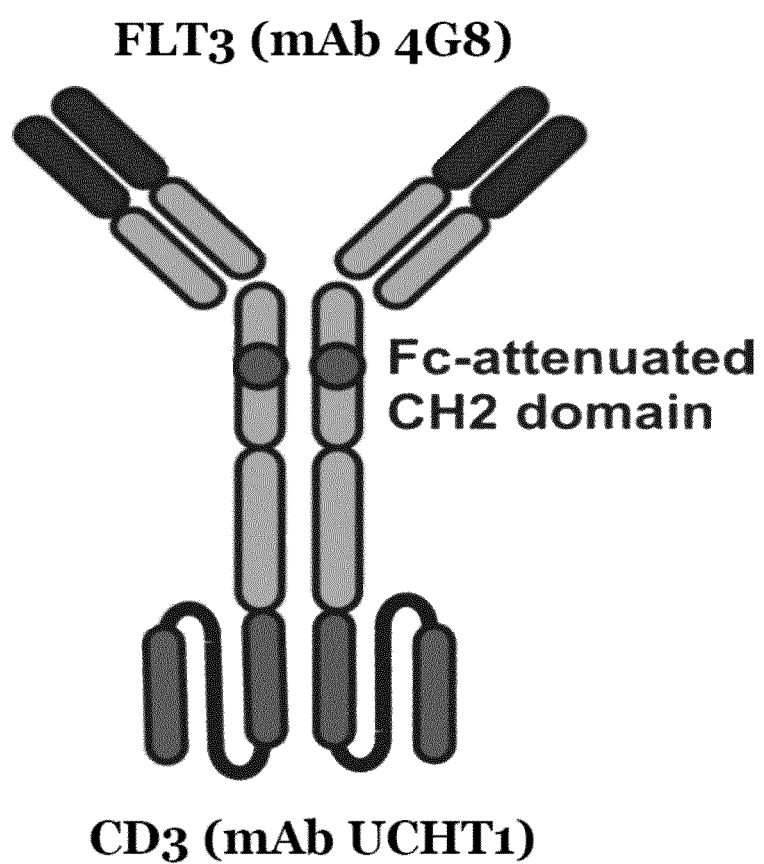

mouse tumor model and in human patient tumor samples. The antibodies of the invention are provided as monospecific constructs or in a bispecific FLT$_3$×CD$_3$ antibody format and show excellent target affinity and/or tumor cell killing. The present invention also relates methods for producing the antigen binding proteins of the invention as well as nucleic acids encoding them, vectors for and host cells for their expression. The invention further relates to methods of treating or diagnosing a disease such as leukemia using an FLT$_3$ antigen binding protein (ABP) of the invention.

11 Claims, 11 Drawing Sheets

Specification includes a Sequence Listing.

(51) Int. Cl.
*A61P 35/02* (2006.01)
*C07K 16/46* (2006.01)

(52) U.S. Cl.
CPC ...... *C07K 16/468* (2013.01); *A61K 2039/505* (2013.01); *C07K 2317/24* (2013.01); *C07K 2317/31* (2013.01); *C07K 2317/565* (2013.01); *C07K 2317/622* (2013.01); *C07K 2317/732* (2013.01); *C07K 2317/92* (2013.01)

(56) References Cited

U.S. PATENT DOCUMENTS

| | | | | |
|---|---|---|---|---|
| 6,156,882 | A * | 12/2000 | Buhring | G01N 33/56972 530/391.1 |
| 9,023,996 | B2 * | 5/2015 | Grosse-Hovest | C07K 16/2896 435/328 |
| 9,718,893 | B2 * | 8/2017 | Jung | C07K 16/2863 |
| 2006/0008883 | A1 * | 1/2006 | Lazar | G16B 30/10 435/69.7 |
| 2006/0024298 | A1 | 2/2006 | Lazar et al. | |
| 2007/0071675 | A1 | 3/2007 | Wu et al. | |

FOREIGN PATENT DOCUMENTS

| | | |
|---|---|---|
| JP | 2008518619 | 6/2008 |
| JP | 2012505654 | 3/2012 |
| JP | 2015502373 | 1/2015 |
| WO | 0177342 A1 | 10/2001 |
| WO | 2006050491 | 5/2006 |
| WO | 2010045340 | 4/2010 |
| WO | 2011/076922 A1 | 6/2011 |
| WO | 2013092001 A1 | 6/2013 |
| WO | 2015/158868 A1 | 10/2015 |
| WO | 2017/176760 A2 | 10/2017 |
| WO | 2013092001 | 10/2017 |
| WO | 2017167760 A2 | 10/2017 |
| WO | 2020/053300 A1 | 3/2020 |

OTHER PUBLICATIONS

Prevention. Cambridge Dictionary. https://dictionary.cambridge.org/us/dictionary/english/prevention. Accessed online Feb. 23, 2024 (Year: 2024).*
Umar, A., Dunn, B. & Greenwald, P. Future directions in cancer prevention. Nat Rev Cancer 12, 835-848 (2012). https://doi.org/10.1038/nrc3397 (Year: 2012).*
Bode, A., Dong, Z. Cancer prevention research—then and now. Nat Rev Cancer 9, 508-516 (2009). https://doi.org/10.1038/nrc2646 (Year: 2009).*
Kaczmarek M, Poznańska J, Fechner F, Michalska N, Paszkowska S, Napierała A, Mackiewicz A. Cancer Vaccine Therapeutics: Limitations and Effectiveness—A Literature Review. Cells. 2023; 12(17):2159. https://doi.org/10.3390/cells 12172159 (Year: 2023).*
Culang et al. The structural basis of antibody-antigen recognition. Front. Immunol., Oct. 8, 2013. Sec. B Cell Biology. Vol. 4—2013 (Year: 2013).*
Kapingidza et al. (2020). Antigen-Antibody Complexes. In: Hoeger, U., Harris, J. (eds) Vertebrate and Invertebrate Respiratory Proteins, Lipoproteins and other Body Fluid Proteins. Subcellular Biochemistry, vol. 94. Springer, Cham. (Year: 2020).*
Portion. Merriam-Webster.https://www.merriam-webster.com/dictionary/portion Accessed online Feb. 26, 2024. (Year: 2024).*
Salih et al. Generation, Functional Characterization and Clinical Application of a Novel Fc-Optimized Anti-FLT3 Antibody for the Treatment of Acute Myeloid Leukemia. Blood. vol. 116, Iss: 21, Nov. 19, 2010 (Year: 2010).*
Safdari et al. (2013) Antibody humanization methods—a review and update, Biotechnology and Genetic Engineering Reviews, 29:2 , 175-186, DOI: 10.1080/02648725.2013.801235 (Year: 2013).*
Sarfati et al. Preventing cancer: the only way forward. The Lancet. vol: 400, Iss: 10352, pp. 540-541, 2022. (Year: 2022).*
Nixon, A., et al., "Engineered protein inhibitors of proteases", Current Opnion in Drug Discovery & Development, 2006, 9(2):261-268.
Nygren, Per-Ake, "Alternative binding proteins: Affibody binding proteins developed from a small three-helix bundle scaffold", FEBS Journal, 275 (2008) 2668-2676.
Perez, P., et al., "Specific targeting of cytotoxic T cells by anti-T3 linked to anti-target cell antibody", Nature, vol. 316, Jul. 25, 1985, pp. 354-356.
Chothia, C., et al., "Canonical Structures for the Hypervariable Regions of Immunoglobulins", J. Mol. Biol. (1987), 196, 901-917.
Ravetch, J., et al., "Fc Receptors", Annu. Rev. Immunol. 1991. 9:457-492.
Rombouts, WJC, et al., "Biological characteristics and prognosis of adult acute myeloid leukemia with internal tandem duplications in the Flt3 gene", Leukemia (2000) 14,675-683.
Rosenthal-Allieri, M., et al., "Monocyte-Independent T Cell Activation by Simultaneous Binding of Three CD2 Monoclonal Antibodies (D66 + T11.1 + GT2)", Cellular Immunology, 163, 88-95 (1995).
Schmidt, T., et al., "Molecular Interaction Between the Streg-tag Affinity Peptide and its Cognate Target, Streptavidin", J. Mol. Biol. (1996) 255, 753-766.
Fujisaki, H., et al., "Expansion of Highly Cytotoxic Human Natural Killer Cells for Cancer Cell Therapy", Cancer Res., 2009; 69: (9), May 1, 2009, 4010-4017.
Laver, W., et al., "Epitopes on Protein Antigens: Misconceptions and Realities", Cell, vol. 61, 553-556, May 18, 1990.
Silverman, J., et al., "Multivalen avimer proteins evolved by exon shuffling of a family of human receptor domains", Nature Biotechnology, vol. 23, No. 12, Dec. 2005, pp. 1556-1561.
Skerra, A., "Alternative binding proteins: Anticalins—harnessing the structural plasticity of the lipocalin ligand pocket to engineer novel binding activities", FEBS Journal, 275 (2008) 2677-2683.
Sondermann, P., et al., "The 3.2-A crystal structure of the human IgG1 Fc fragment-FcgRIII complex", Nature, vol. 406, Jul. 20, 2000, pp. 267-273.
Staerz, U., et al., "Hybrid antibodies can target sites for attack by T cells", Nature, vol. 314, Apr. 18, 1985, pp. 628-631.
Stumpp, M., et al., "DARPins: A new generation of protein therapeutics", Drug Discovery Today, vol. 13, Nos. 15-16, Aug. 2008, pp. 695-701.
Tibben, J., et al., "Pharmacokinetics, Biodistribution and Biological Effects of Intravenously Administered Bispecific Monoclonal Antibody OC/TR F(ab')2 in Ovarian Carcinoma Patients", Int. J. Cancer: 66, 477-483 (1996).
Tomlinson, I., et al., "The structural repertoire of the human Vk domain", The EMBO Journal, vol. 14, No. 18, pp. 4628-4638, 1995.
Topp, M., et al., "Targeted Therapy with the T-Cell-Engaging Antibody Blinatumomab of Chemotherapy-Refractory Minimal Residual Disease in B-Lineage Acute Lymphoblastic Leukemia

(56) References Cited

OTHER PUBLICATIONS

Patients Results in High Response Rate and Prolonged Leukemia-Free Survival", Journal of Clinical Oncology, vol. 29, No. 18, Jun. 20, 2011, pp. 2493-2498.
Venturi, M., et al., "High Level Production of Functional Antibody Fab Fragments in an Oxidizing Bacterial Cytoplasm", J. Mol. Biol. (2002) 315, 1-8.
Virnekäs, B., et al., "Trinucleotide phosphoramidites: ideal reagents for the synthesis of mixed oligonucleotides for random mutagenesis", Nucleic Acids Research, 1994, vol. 22, No. 25, pp. 5600-5607.
Wang, L., et al., "Expanding the genetic code", Chem. Commun., 2002, 1-11.
Wang, L., et al., "Expanding the Genetic Code of *Escherichia coli*", Science, vol. 292, Apr. 20, 2001, pp. 498-500.
Watson, C., et al., "Complete Haplotype Sequence of the Human Immunoglobulin Heavy-Chain Variable, Diversity, and Joining Genes and Characterization of Allelic and Copy-Number Variation", The American Journal of Human Genetics, 92, 530-546, Apr. 4, 2013.
Weng, W-K., et al., "Two Immunoglobulin G Fragment C Receptor Polymorphisms Independently Predict Response to Rituximab in Patiens with Follicular Lymphoma", Journal of Clinical Oncology, vol. 21, No. 21, Nov. 1, 2003, pp. 3940-3947.
Wörn, A., et al., "Stability Engineering of Antibody Single-chain Fv Fragments", J. Mol. Biol. (2001) 305, 989-1010.
Zaccolo, M., et al., "An Approach to Random Mutagenesis of DNA Using Mixtures of Triphosphate Derivatives of Nucleoside Analogues", J. Mol. Biol. (1996) 255, 589-603.
Schmiedel, B., et al., "Azacytidine impairs NK cell reactivity while decitabine augments NK cell responsiveness toward stimulation", International Journal of Cancer, 2011; 128:2911-2922.
Michael Dunbar, et al., "Characterization of a Bispecific FLT3 X CD3 Antibody in an Improved, Recombinant Format for the Treatment of Leukemia," Molecular Therapy, 8 pages, dated Apr. 2015.
Juan C. Almagro, et al., "Humanization of antibodies," Frontiers in Bioscience, vol. 13, 2008, dated Jan. 1, 2008.
Li, Y., et al., "Suppression of Leukemia Expressing Wild-Type or ITD-Mutant FLT3 Receptor by a Fully Human Anti-FLT-3 Neutralizing Antibody", Blood, vol. 104, No. 4, Aug. 15, 2004, pp. 1137-1144.
International Search Report, International Application No. PCT/EP2019/074268, mailed Feb. 14, 2020, 7 pages.
Written Opinion of the International Searching Authority, International Application No. PCT/EP/2019/074268, 12 pages.
Abhinandan, K.R., et al., "Analysis and improvements to Kabat and structurally correct numbering of antibody variable domains", Molecular Immunology 45 (2008) 3832-3839.
Adams, G., et al., "Monoclonal antibody therapy of cancer", Nature Biotechnology, vol. 23, No. 9, Sep. 7, 2005, pp. 1147-1157.
Watson, C., et al., "Complete Haplotype Sequence of the Human Immunoglobulin Heavy-Chain Variable, Diversity, and Joining Genes and Characterization of Allelic and Copy-Number Variation", The American Journal of Human Genetics 92 (4), Apr. 4, 2013, pp. 530-546.
Arakawa, F., et al., Cloning and Sequencing of the VH and Vk Genes of an Anti-CD3 Monoclonal Antibody, and Construction of a Mouse/Human Chimeric Antibody, J. Biochem. 120, 657-662 (1996).
Armour, K., et al., "Recombinant human IgG molecules lacking Fcg receptor I binding and monocyte triggering activities", Eur. J. Immunol. 1999. 29: 2613-2624.
Baerga-Ortiz, A., et al., "Epitope mapping of a monoclonal antibody against human thrombin by H/D-exchange mass spectrometry reveals selection of a diverse sequence in a highly conserved protein", Protein Science (2002), 11: 1300-1308.
Baessler, T., et al., "Glucocorticoid-Induced Tumor Necrosis Factor Receptor-Related Protein Ligand Subverts Immunosurveillance of Acute Myeloid Leukemia in Humans", Cancer Res 2009; 63: (3), Feb. 1, 2009, 1037-1045.
Bos, G., et al., "Controlled Release of Pharmaceutical Proteins from Hydrogels", Business Briefing: Pharmatech 2003:1-6.

Capel, P., et al., "Heterogeneity of Human IgG Fc Receptors", Immunomethods 4, 25-34 (1994).
Carter, P., et al., "High Level *Escherichia coli* Expression and Production of a Bivalent Humanized Antibody Fragment", Biotechnology, 10: 163-167 (1992).
Cartron, G., et al., "Therapeutics activity of humanized anti-CD20 monoclonal antibody and polymorphism in IgG Fo receptor Fc gRIIIa gene", Blood, Feb. 1, 2002, vol. 99, No. 3, 754-758.
Ceuppens, J., et al., "Human T Cell Activation Induced by a Monoclonal Mouse IgG3 Anti-CD3 Antibody (RIV9) Requires Binding of the Fc Part of the Antibody to the Monocytic 72-kDa High-Affinity Fc Receptor (FcRI)", Cellular Immunology 118, 136-146 (1989).
Ceuppens, J., et al., "Direct demonstration of binding of anti-Leu 4 antibody to the 40 kDa Fc receptor on monocytes as a prerequisite for anti-Leu 4-induced T cell mitogenesis", J Immunol 1987; 139:4067-4071.
Chothia, C., et al., "Structural Repertoire of the Human VH Segments", J. Mol. Biol. (1992) 227, 799-817.
Eli Lilly and Company, "Study of IMC-EB10 in Participant with Leukemia", ClinicalTrials.gov Identifier: NCT00887926, 4 pages, 2019.
Clynes, R., et al., Fc receptors are required in passive and active immunity to melanoma, Proc. Natl. Acad. Sci. USA, vol. 95, pp. 652-656, Jan. 1998.
Clynes, R., et al., "Inhibitory Fc receptors modulate in vivo cytoxcity against tumor targets", Nature Medicine, vol. 6, No. 4, Apr. 2000, pp. 443-446.
Coloma, M., et al., "Design and production of novel tetravalent bispecific antibodies", Nature Biotechnology, vol. 15, Feb. 1997, pp. 159-163.
Cragg, M., et al., "Signaling antibodies in cancert therapy", Curr. Opinion in Immunology 1999, 11:541-547.
Davis, L., et al., "Regulation of human T lymphocyte mitogenesis by antibodies to CD3", J Immunol 1986; 137:3758-3767.
De Haas, M., et al., "Fcg receptors of phagocytes", J. Lab. Clin. Med. 126: 3030-41 (1995).
Desmet, J., et al., "Structural basis of IL-23 antagonism by an Alphabody protein scaffold", Nature Communications 5:5237 (2014), 12 pages.
Diem, M., et al., Selection of high-affinity Centyrin FN3 domains from a simple library diversified at a combination of strand and loop positions, Protein Engineering, Design & Selection vol. 27, No. 10, pp. 419-429, 2014.
Ebersbach, H., et al., "Affilin-Novel Binding Molecules Based on Human g-B-Crystallin, an All b-Sheet Protein", J Mo Biol, 372:172-185 (2007).
Skerra, A., "Use of the tetracycline promoter for the tightly regulated production of a murine antibody fragment in *Escherichia coli*", Gene, 151 (1994) 131-135.
Gazzano-Santoro, H., et al., "A non-radioactive complement-dependent cytotoxicity assay for anti-CD20 monocolonal antibody", Journal of Immunological Methods 202 (1997) 163-171.
Gebauer, M., et al., "Engineered protein scaffolds as next-generation antibody therapeutics", Current Opinion in Chemical Biology 2009, 13:245-255.
Glennie, M., et al., "Clinical trials of antibody therapy", Immunol Today, vol. 21. No. 8, 403-410 (2000).
Grabulovsi, D., et al., "A Novel, Non-immunogenic Fyn SH3-derived Binding Protein with Tumor Vascular Targeting Properties", The Journal of Biological Chemistry vol. 282, No. 5, pp. 3196-3204, Feb. 2, 2007.
Grosse-Hovest, L., et al., "A recombinant bispecific single-chain antibody induces targeted, supra-agonistic CD28-stimulation and tumor cell killing", Eur. J. Immunol. 2003, 33: 1334-1340.
Guss, B., et al., "Structure of the lgG-binding regions of streptococcal protein G" The EMBO Journal, vol. 5., No. 7, pp. 1567-1575, 1986.
Holt, L., et al., "Domain antibodies: proteins for therapy", Trends in Biotechnology, vol. 21, No. 11, Nov. 2003, 484-490.
Honegger, A., et al., "Yet Another Numbering Scheme for Immunoglobulin Variable Domains: An Automatic Modeling and Analysis Tool", J. Mol. Biol. (2001) 3009, 657-670.

(56) References Cited

OTHER PUBLICATIONS

Ichiyoshi, Y., et al., "A numan anti-insulin IgG autoantibody apparently arises through clonal selection from an Insulin-specific "germline" natural antibody template. Analysis by V gene segment reassortment and site-directed mutagenesis", J Immunol 1995; 154:226-238.

Patton, J., et al., "The Lungs as a Portal of Entry for Systemic Drug Delivery", Proc. Amer. Thoracic Soc. 2004 vol. 1, pp. 338-344.

Johnson, A., et al., "Sensitive Affimer and Antibody Based Impedimetric Label-Free Assays for C-Reactive Protein", Anal. Chem. 2012, 84, 6553-6560.

Jung, G., et al., "Target cell-induced T cell activation with bi- and trispecific antibody fragments", Eur. J. Immunol. 1991. 21:2431-2435.

Jung, G., et al., "An in-vitro model for tumor immunotherapy with antibody heteroconjugates", Immunology Today, vol. 9, No. 9, 1988, pp. 257-260.

Jung, G., et al., "Activation of human peripheral blood mononuclear cells by anti-T3: Killing of tumor target cells coated with anti-target-anti-T3 conjugates", Proc. Natl. Acad. Sci. USA, vol. 83, pp. 4479-4483, Jun. 1986.

Kashmiri, S., et al., "SCD grafting-a new approach to antibody humanization", Methods 36 (2005) 25-34.

Koide, A., et al., "Antibody Mimics Based on the Scaffold of the Fibronectin Type III Domain", Methods in Molecular Biology, vol. 352: 95 (2007).

Krehenbrink, M., et al., "Artificial Binding Proteins (Affitins) as Probes for Conformational Changes in Secretin PulD", J. Mol. Biol. (2008) 383, 1058-1068.

Kroesen, B.J., et al., "Phase I study of intravenously applied bispecific antibody in renal cell cancer patients receiving subcutaneous interleukin 2", J. Cancer (1994), 70, 652-661.

Lefranc, M-P., et al., "IMGT unique numbering for immunoglobulin and T cell receptor variable domains and Ig superfamily V-like domains", Developmental and Comparative Immunology 27 (2003) 55-77.

Lindmark, R., et al., "Binding of Immunoglobulins to Protein A and Immunoglobulin Levels in Mammalian Sera", Journal of Immunological Methods, 62 (1983) 1-13.

Long, A., et al., "4-1BB costimulation ameliorates T cell exhaustion induced by tonic signaling of chimeric antigen receptors", Nature Medicine, vol. 21, No. 6, Jun. 2015, pp. 581-593.

Meidan, V., et al., "Emerging Technologies in Transdermal Therapeutics", American Journal of Therapeutics 11, 312-316 (2004).

Christian Klein et al.: "Epitope interactions of monoclonal antibodies targeting CD20 and their relationship to functional properties", MABS, vol. 5, No. 1, Jan. 1, 2013 (Jan. 1, 2013), pp. 22-33, XP055117097, ISSN: 1942-0862, DOI: 10.4161 /mabs.22771.

Li Yiwen et al: "Suppression of leukemia expressing wild-type or ITD-mutant FL T3 receptor by a fully human anti-FL T3 neutralizing antibody", Blood, vol. 104, No. 4, Aug. 15, 2004 (Aug. 15, 2004), pp. 1137-1144, XP002548252, ISSN: 0006-4971, DOI: 10.1182/BLOOD-2003-07-2585 [retrieved on Apr. 22, 2004].

Intellectual Property of the Russian Federation, "Office Action" regarding Application No. 2021109833, 17 pages, mailed Jan. 15, 2024.

China National Intellectual Property Administration, "Office Action" regarding Application No. 201980069438.6, 32 pages, mailed Jan. 18, 2024.

Israel Patent Office, "Official Notification," regarding Application No. 281351, 5 pages, dated Apr. 5, 2024.

Singapore Patent Ofrfice, "Second Written Opinion," regarding Application No. 11202102178P, 8 pages, dated Jun. 19, 2024.

\* cited by examiner

FIGURE 2

A

*IgGsc_FLT3 (4G8 mouse)_CD3 (hUCHT1) Heavy chain*

<u>QVQLQQPGAELVKPGASLKLSCKSSGYTFTSYWMHWVRQRPGHGLEWIGEIDPSDSYKDY</u>
FLT3 (4G8) HC variable region <u>NQKFKDKATLTVDRSSNTAYMHLSSLTSDDSAVYYCARAITTTPFDFWGQGTTLTVSS</u>
FLT3 (4G8) HC variable region <u>ASTKGPSVFPLAPSSKSTSGGTAALGCLVKDYFPEPVTVSWNSGALTSGVHTFPAVLQSSG</u>
IgG1 CH1 domain <u>LYSLSSVVTVPSSSLGTQTYICNVNHKPSNTKVDKKV</u><u>EPKSCDKTHTCPPCPAPPVAGPSVF</u>
IgG1 CH1 domain                IgG1 hinge region <u>LFPPKPKDTLMISRTPEVTCVVVGVSHEDPEVKFNWYVDGVEVHNAKTKPREEQYNSTYR</u>
Mutated IgG1CH2 domain <u>VVSVLTVLHQDWLNGKEYKCKVSNKQLPSPIEKTISKAK</u><u>GQPREPQVYTLPPSRDELTKNQV</u>
Mutated IgG1CH2 domain          IgG1 CH3 domain <u>SLTCLVKGFYPSDIAVEWESNGQPENNYKTTPPVLDSDGSFFLYSKLTVDKSRWQQGNVFS</u>
IgG1 CH3 domain <u>CSVMHEALHNHYTQKSLSLSPGK</u><u>SGDIQMTQSPSSLSASVGDRVTITCRASQDIRNYLNWY</u>
IgG1 CH3 domain      Humanized CD3 single chain (UCHT1) LC variable region <u>QQKPGKAPKLLIYYTSRLESGVPSRFSGSGSGTDYTLTISSLQPEDFATYYCQQGNTLPWTF</u>
Humanized CD3 single chain (UCHT1) LC variable region <u>GQGTKVEIK</u><u>GGGGSGGGGSGGGGS</u><u>EVQLVESGGGLVQPGGSLRLSCAASGYSFTGYTM</u>
         Linker region        Humanized CD3 single chain (UCHT1) HC variable region <u>NWVRQAPGKGLEWVALINPYKGVSTYNQKFKDRFTISVDKSKNTAYLQMNSLRAEDTAVYY</u>
Humanized CD3 single chain (UCHT1) HC variable region <u>CARSGYYGDSDWYFDVWGQGTLVTVSS</u>**
Humanized CD3 single chain (UCHT1) HC variable region

B

*FLT3 (4G8 mouse)_Kappa_ Light chain*

<u>DIVLTQSPATLSVTPGDSVSLSCRASQSISNNLHWYQQKSHESPRLLIKYASQSISGIPSRFS</u>
FLT3 (4G8) LC variable region

Binding to NALM16 cells (FLT3+)

FIGURE 8
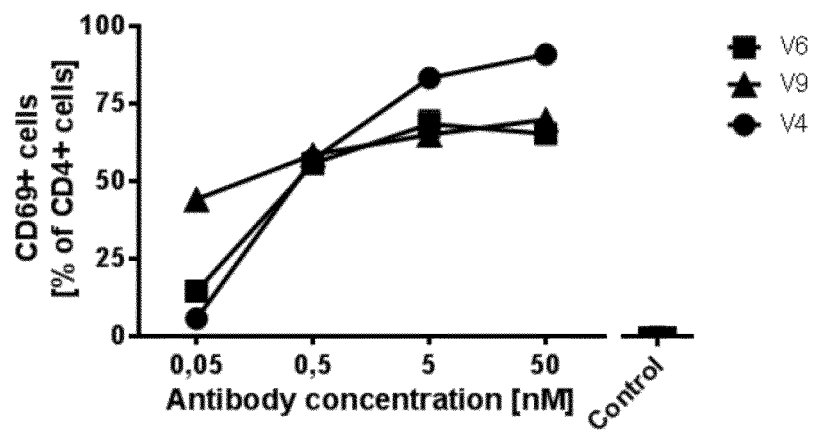
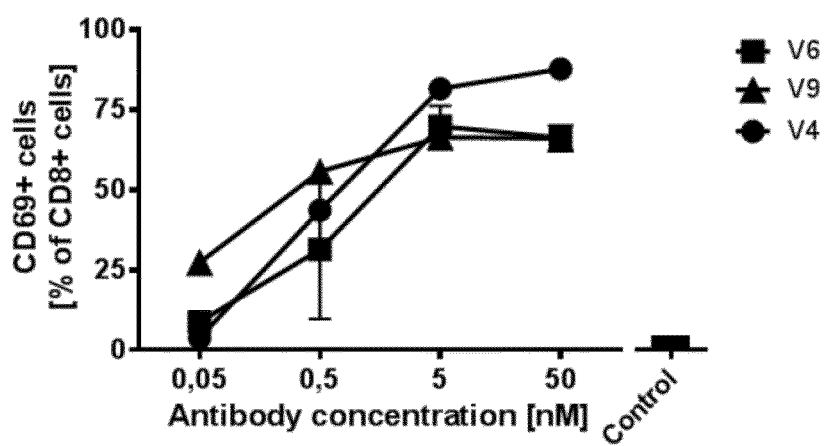
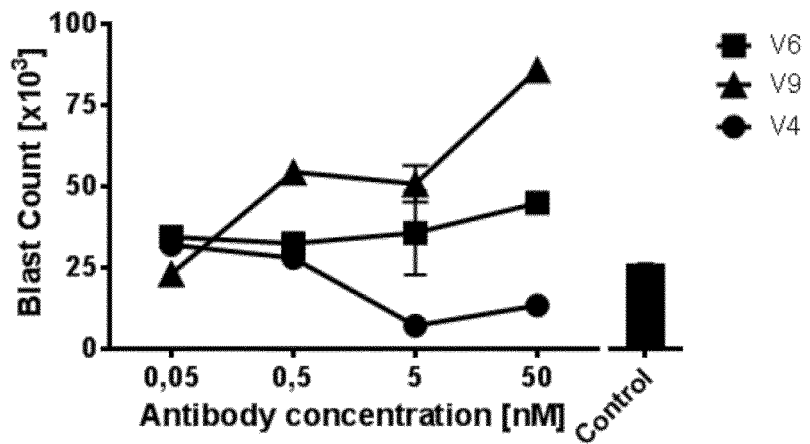

FIGURE 10
A
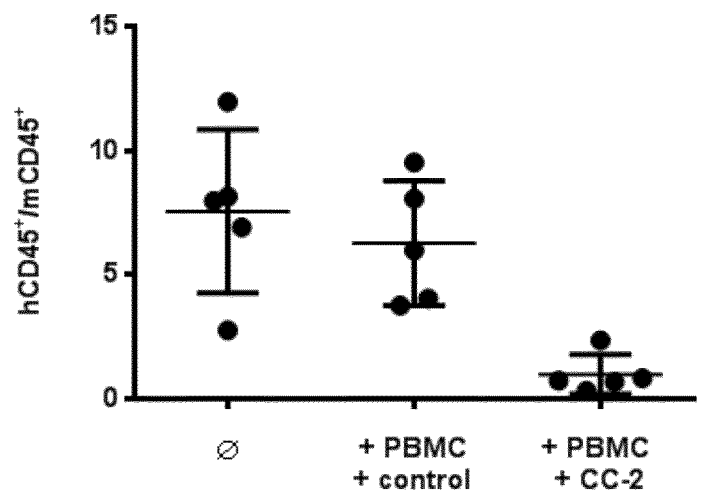
B
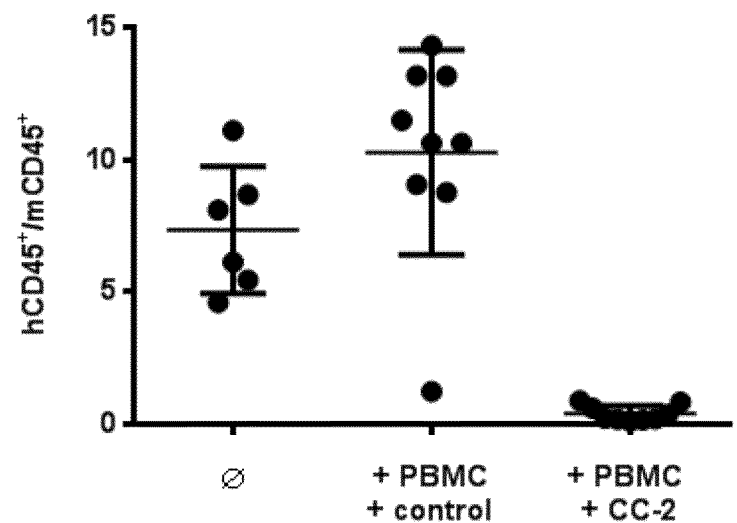

```
                        SEQUENCE LISTING

<160> NUMBER OF SEQ ID NOS: 79

<210> SEQ ID NO 1
    <211> LENGTH: 5
    <212> TYPE: PRT
    <213> ORGANISM: artificial
    <220> FEATURE:
    <223> OTHER INFORMATION: variant antibody sequence

<400> SEQUENCE: 1

Ser Tyr Trp Met His
    1               5

<210> SEQ ID NO 2
    <211> LENGTH: 17
    <212> TYPE: PRT
    <213> ORGANISM: artificial
    <220> FEATURE:
    <223> OTHER INFORMATION: variant antibody sequence

<400> SEQUENCE: 2

Glu Ile Asp Pro Ser Asp Ser Tyr Lys Asp Tyr Asn Gln Lys Phe Lys
    1               5                   10                  15

Asp

<210> SEQ ID NO 3
    <211> LENGTH: 9
    <212> TYPE: PRT
    <213> ORGANISM: artificial
    <220> FEATURE:
    <223> OTHER INFORMATION: variant antibody sequence
```

<400> SEQUENCE: 3

Ala Ile Thr Thr Thr Pro Phe Asp Phe
1               5

<210> SEQ ID NO 4
<211> LENGTH: 118
<212> TYPE: PRT
<213> ORGANISM: artificial
<220> FEATURE:
<223> OTHER INFORMATION: variant antibody sequence

<400> SEQUENCE: 4

Gln Val Gln Leu Gln Gln Pro Gly Ala Glu Leu Val Lys Pro Gly Ala
1               5                   10                  15

Ser Leu Lys Leu Ser Cys Lys Ser Ser Gly Tyr Thr Phe Thr Ser Tyr
            20                  25                  30

Trp Met His Trp Val Arg Gln Arg Pro Gly His Gly Leu Glu Trp Ile
        35                  40                  45

Gly Glu Ile Asp Pro Ser Asp Ser Tyr Lys Asp Tyr Asn Gln Lys Phe
    50                  55                  60

Lys Asp Lys Ala Thr Leu Thr Val Asp Arg Ser Ser Asn Thr Ala Tyr
65                  70                  75                  80

Met His Leu Ser Ser Leu Thr Ser Asp Asp Ser Ala Val Tyr Tyr Cys
                85                  90                  95

Ala Arg Ala Ile Thr Thr Thr Pro Phe Asp Phe Trp Gly Gln Gly Thr
            100                 105                 110

Thr Leu Thr Val Ser Ser
        115

<210> SEQ ID NO 5
<211> LENGTH: 11
<212> TYPE: PRT
<213> ORGANISM: artificial
<220> FEATURE:
<223> OTHER INFORMATION: variant antibody sequence

<400> SEQUENCE: 5

Arg Ala Ser Gln Ser Ile Ser Asn Asn Leu His
1               5                   10

<210> SEQ ID NO 6
<211> LENGTH: 7
<212> TYPE: PRT
<213> ORGANISM: artificial
<220> FEATURE:
<223> OTHER INFORMATION: variant antibody sequence

<400> SEQUENCE: 6

Tyr Ala Ser Gln Ser Ile Ser
1               5

<210> SEQ ID NO 7
<211> LENGTH: 9
<212> TYPE: PRT
<213> ORGANISM: artificial
<220> FEATURE:
<223> OTHER INFORMATION: variant antibody sequence

<400> SEQUENCE: 7

Gln Gln Ser Asn Thr Trp Pro Tyr Thr
1               5

<210> SEQ ID NO 8
<211> LENGTH: 107
<212> TYPE: PRT
<213> ORGANISM: artificial
<220> FEATURE:
<223> OTHER INFORMATION: variant antibody sequence

<400> SEQUENCE: 8

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Val Tyr Phe Cys Gln Gln Ser Asn Thr Trp Pro Tyr
                85                  90                  95

Thr Phe Gly Gly Gly Thr Lys Leu Glu Ile Lys
            100                 105

<210> SEQ ID NO 9
<211> LENGTH: 107
<212> TYPE: PRT
<213> ORGANISM: artificial
<220> FEATURE:
<223> OTHER INFORMATION: variant antibody sequence

<400> SEQUENCE: 9

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 10
<211> LENGTH: 98
<212> TYPE: PRT
<213> ORGANISM: artificial
<220> FEATURE:
<223> OTHER INFORMATION: variant antibody sequence

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
              35                  40                  45
Gly Val His Thr Phe Pro Ala Val Leu Gln Ser Ser Gly Leu Tyr Ser
             50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val

<210> SEQ ID NO 11
<211> LENGTH: 15
<212> TYPE: PRT
<213> ORGANISM: artificial
<220> FEATURE:
<223> OTHER INFORMATION: variant antibody sequence

<400> SEQUENCE: 11

Glu Pro Lys Ser Cys Asp Lys Thr His Thr Cys Pro Pro Cys Pro
 1               5                  10                  15

<210> SEQ ID NO 12
<211> LENGTH: 109
<212> TYPE: PRT
<213> ORGANISM: artificial
<220> FEATURE:
<223> OTHER INFORMATION: variant antibody sequence

<400> SEQUENCE: 12

Ala Pro Pro Val Ala Gly Pro Ser Val Phe Leu Phe Pro Pro Lys Pro
 1               5                  10                  15

Lys Asp Thr Leu Met Ile Ser Arg Thr Pro Glu Val Thr Cys Val Val
                 20                  25                  30

Val Gly Val Ser His Glu Asp Pro Glu Val Lys Phe Asn Trp Tyr Val
             35                  40                  45

Asp Gly Val Glu Val His Asn Ala Lys Thr Lys Pro Arg Glu Glu Gln
         50                  55                  60

Tyr Asn Ser Thr Tyr Arg Val Val Ser Val Leu Thr Val Leu His Gln
 65                  70                  75                  80

Asp Trp Leu Asn Gly Lys Glu Tyr Lys Cys Lys Val Ser Asn Lys Gln
                 85                  90                  95

Leu Pro Ser Pro Ile Glu Lys Thr Ile Ser Lys Ala Lys
            100                 105

<210> SEQ ID NO 13
<211> LENGTH: 109
<212> TYPE: PRT
<213> ORGANISM: artificial
<220> FEATURE:
<223> OTHER INFORMATION: variant antibody sequence

<400> SEQUENCE: 13

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Asp Ser Asp Gly Ser Phe
 65                  55                  60
```

```
Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys Ser Gly
            100                 105
```

<210> SEQ ID NO 14
<211> LENGTH: 244
<212> TYPE: PRT
<213> ORGANISM: artificial
<220> FEATURE:
<223> OTHER INFORMATION: variant antibody sequence

<400> SEQUENCE: 14

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Arg Asn Tyr
                 20                  25                  30

Leu Asn Trp Tyr Gln Gln Lys Pro Gly Lys Ala Pro Lys Leu Leu Ile
             35                  40                  45

Tyr Tyr Thr Ser Arg Leu Glu Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Gly Asn Thr Leu Pro Trp
                 85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val Glu
            115                 120                 125

Ser Gly Gly Gly Leu Val Gln Pro Gly Gly Ser Leu Arg Leu Ser Cys
130                 135                 140

Ala Ala Ser Gly Tyr Ser Phe Thr Gly Tyr Thr Met Asn Trp Val Arg
145                 150                 155                 160

Gln Ala Pro Gly Lys Gly Leu Glu Trp Val Ala Leu Ile Asn Pro Tyr
                165                 170                 175

Lys Gly Val Ser Thr Tyr Asn Gln Lys Phe Lys Asp Arg Phe Thr Ile
                180                 185                 190

Ser Val Asp Lys Ser Lys Asn Thr Ala Tyr Leu Gln Met Asn Ser Leu
            195                 200                 205

Arg Ala Glu Asp Thr Ala Val Tyr Tyr Cys Ala Arg Ser Gly Tyr Tyr
        210                 215                 220

Gly Asp Ser Asp Trp Tyr Phe Asp Val Trp Gly Gln Gly Thr Leu Val
225                 230                 235                 240

Thr Val Ser Ser
```

<210> SEQ ID NO 15
<211> LENGTH: 118
<212> TYPE: PRT
<213> ORGANISM: artificial
<220> FEATURE:
<223> OTHER INFORMATION: variant antibody sequence

<400> SEQUENCE: 15

```
Gln Val Gln Leu Val Gln Ser Gly Ala Glu Val Lys Lys Pro Gly Gly
  1               5                  10                  15
```

```
Ser Leu Arg Leu Ser Cys Ala Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Thr Asp Tyr Ala Gln Lys Phe
 50                  55                  60

Lys Asp Arg Val Thr Ile Ser Arg Asp Thr Ser Lys Asn Thr Leu Tyr
 65                  70                  75                  80

Leu Gln Leu Ser Ser Leu Arg Ala Glu Asp Thr Ala Val Tyr Tyr Cys
                85                  90                  95

Ala Arg Ala Ile Thr Thr Thr Pro Phe Asp Phe Trp Gly Gln Gly Thr
            100                 105                 110

Leu Val Thr Val Ser Ser
            115

<210> SEQ ID NO 16
<211> LENGTH: 107
<212> TYPE: PRT
<213> ORGANISM: artificial
<220> FEATURE:
<223> OTHER INFORMATION: variant antibody sequence

<400> SEQUENCE: 16

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Ala Ser Gln Ser Ala Ser Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys
            100                 105

<210> SEQ ID NO 17
<211> LENGTH: 118
<212> TYPE: PRT
<213> ORGANISM: artificial
<220> FEATURE:
<223> OTHER INFORMATION: variant antibody sequence

<400> SEQUENCE: 17

Gln Val Gln Leu Val Gln Ser Gly Ala Glu Val Lys Lys Pro Gly Gly
 1               5                  10                  15

Ser Leu Arg Leu Ser Cys Ala Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Thr Asp Tyr Ala Gln Lys Phe
 50                  55                  60

Lys Asp Arg Val Thr Ile Ser Arg Asp Thr Ser Lys Asn Thr Leu Tyr
 65                  70                  75                  80

Leu Gln Leu Ser Ser Leu Arg Ala Glu Asp Thr Ala Val Tyr Tyr Cys
                85                  90                  95
```

Ala Arg Ala Ile Thr Thr Thr Pro Phe Asp Phe Trp Gly Gln Gly Thr
            100                 105                 110

Leu Val Thr Val Ser Ser
        115

<210> SEQ ID NO 18
<211> LENGTH: 107
<212> TYPE: PRT
<213> ORGANISM: artificial
<220> FEATURE:
<223> OTHER INFORMATION: variant antibody sequence

<400> SEQUENCE: 18

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys
            100                 105

<210> SEQ ID NO 19
<211> LENGTH: 118
<212> TYPE: PRT
<213> ORGANISM: artificial
<220> FEATURE:
<223> OTHER INFORMATION: variant antibody sequence

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Lys Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Ile Thr Thr Thr Pro Phe Asp Phe Trp Gly Gln Gly Thr
            100                 105                 110

Thr Val Thr Val Ser Ser
        115

<210> SEQ ID NO 20
<211> LENGTH: 107
<212> TYPE: PRT
<213> ORGANISM: artificial
<220> FEATURE:
<223> OTHER INFORMATION: variant antibody sequence

<400> SEQUENCE: 20

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Ala Ser Gln Ser Ser Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys
            100                 105

<210> SEQ ID NO 21
<211> LENGTH: 118
<212> TYPE: PRT
<213> ORGANISM: artificial
<220> FEATURE:
<223> OTHER INFORMATION: variant antibody sequence

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Lys Asp Tyr Asn Gln Lys Phe
50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Ile Thr Thr Thr Pro Phe Asp Phe Trp Gly Gln Gly Thr
            100                 105                 110

Thr Val Thr Val Ser Ser
        115

<210> SEQ ID NO 22
<211> LENGTH: 107
<212> TYPE: PRT
<213> ORGANISM: artificial
<220> FEATURE:
<223> OTHER INFORMATION: variant antibody sequence

<400> SEQUENCE: 22

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
50                  55                  60

```
Ser Gly Ser Gly Thr Glu Phe Thr Leu Thr Ile Ser Ser Leu Gln Ser
 65                  70                  75                  80

Glu Asp Phe Ala Val Tyr Phe Cys Gln Gln Ser Asn Thr Trp Pro Tyr
                 85                  90                  95

Thr Phe Gly Gly Gly Thr Lys Leu Glu Ile Lys
                100                 105

<210> SEQ ID NO 23
<211> LENGTH: 118
<212> TYPE: PRT
<213> ORGANISM: artificial
<220> FEATURE:
<223> OTHER INFORMATION: variant antibody sequence

<400> SEQUENCE: 23

Gln Val Gln Leu Val Gln Ser Gly Ala Glu Val Lys Lys Pro Gly Gly
1               5                   10                  15

Ser Leu Arg Leu Ser Cys Ala Ala Ser Gly Tyr Thr Phe Thr Ser Tyr
                20                  25                  30

Trp Met His Trp Val Arg Gln Ala Pro Gly Gln Gly Leu Glu Trp Ile
            35                  40                  45

Gly Glu Ile Asp Pro Ser Asp Ser Tyr Lys Asp Tyr Asn Gln Lys Phe
    50                  55                  60

Lys Asp Arg Val Thr Ile Ser Arg Asp Thr Ser Lys Asn Thr Leu Tyr
 65                 70                  75                  80

Leu Gln Leu Ser Ser Leu Arg Ala Glu Asp Thr Ala Val Tyr Tyr Cys
                85                  90                  95

Ala Arg Ala Ile Thr Thr Thr Pro Phe Asp Phe Trp Gly Gln Gly Thr
                100                 105                 110

Leu Val Thr Val Ser Ser
            115

<210> SEQ ID NO 24
<211> LENGTH: 107
<212> TYPE: PRT
<213> ORGANISM: artificial
<220> FEATURE:
<223> OTHER INFORMATION: variant antibody sequence

<400> SEQUENCE: 24

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
                20                  25                  30

Leu His Trp Tyr Gln Gln Lys Pro Gly Gln Ala Pro Arg Leu Leu Ile
            35                  40                  45

Lys Tyr Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
 65                 70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys
                100                 105

<210> SEQ ID NO 25
<211> LENGTH: 244
<212> TYPE: PRT
```

<213> ORGANISM: artificial
<220> FEATURE:
<223> OTHER INFORMATION: variant antibody sequence

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Gly Gly Leu Val Gln Pro Gly Gly Ser Leu Arg Leu Ser Cys
130                 135                 140

Ala Ala Ser Gly Tyr Ser Phe Thr Gly Tyr Thr Met Asn Trp Val Arg
145                 150                 155                 160

Gln Ala Pro Gly Lys Gly Leu Glu Trp Val Ala Leu Ile Asn Pro Tyr
                165                 170                 175

Lys Gly Val Ser Thr Tyr Ala Asp Ser Phe Lys Gly Arg Phe Thr Ile
            180                 185                 190

Ser Val Asp Asp Ser Lys Asn Thr Ala Tyr Leu Gln Met Asn Ser Leu
        195                 200                 205

Arg Ala Glu Asp Thr Ala Val Tyr Tyr Cys Ala Arg Ser Gly Tyr Tyr
    210                 215                 220

Gly Asp Ser Asp Trp Tyr Phe Asp Val Trp Gly Gln Gly Thr Leu Val
225                 230                 235                 240

Thr Val Ser Ser

<210> SEQ ID NO 26
<211> LENGTH: 244
<212> TYPE: PRT
<213> ORGANISM: artificial
<220> FEATURE:
<223> OTHER INFORMATION: variant antibody sequence

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp

```
                    85                  90                  95
Thr Phe Gly Gln Gly Thr Lys Val Glu Ile Lys Gly Gly Gly Ser
                100                 105                 110

Gly Gly Gly Gly Ser Gly Gly Gly Ser Glu Val Gln Leu Val Glu
            115                 120                 125

Ser Gly Gly Gly Leu Val Gln Pro Gly Gly Ser Leu Arg Leu Ser Cys
        130                 135                 140

Ala Ala Ser Gly Tyr Ser Phe Thr Gly Tyr Thr Met Asn Trp Val Arg
145                 150                 155                 160

Gln Ala Pro Gly Lys Gly Leu Glu Trp Val Ala Leu Ile Asn Pro Tyr
                165                 170                 175

Lys Gly Val Ser Thr Tyr Asn Gln Lys Phe Lys Asp Arg Phe Thr Ile
                180                 185                 190

Ser Val Asp Asp Ser Lys Asn Thr Ala Tyr Leu Gln Met Asn Ser Leu
            195                 200                 205

Arg Ala Glu Asp Thr Ala Val Tyr Tyr Cys Ala Arg Ser Gly Tyr Tyr
    210                 215                 220

Gly Asp Ser Asp Trp Tyr Phe Asp Val Trp Gly Gln Gly Thr Leu Val
225                 230                 235                 240

Thr Val Ser Ser

<210> SEQ ID NO 27
<211> LENGTH: 244
<212> TYPE: PRT
<213> ORGANISM: artificial
<220> FEATURE:
<223> OTHER INFORMATION: variant antibody sequence

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
                20                  25                  30

Thr Met Asn Trp Val Arg Gln Ala Pro Gly Lys Gly Leu Glu Trp Val
            35                  40                  45

Ala Leu Ile Asn Pro Tyr Lys Gly Val Ser Thr Tyr Asn Gln Lys Phe
        50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
                100                 105                 110

Gly Gln Gly Thr Leu Val Thr Val Ser Ser Gly Gly Gly Gly Ser Gly
            115                 120                 125

Gly Gly Ser Gly Gly Gly Ser Asp Ile Gln Met Thr Gln Ser
        130                 135                 140

Pro Ser Ser Leu Ser Ala Ser Val Gly Asp Arg Val Thr Ile Thr Cys
145                 150                 155                 160

Arg Ala Ser Gln Asp Ile Arg Asn Tyr Leu Asn Trp Tyr Gln Gln Lys
                165                 170                 175

Pro Gly Lys Ala Pro Lys Leu Leu Ile Tyr Tyr Thr Ser Arg Leu Glu
            180                 185                 190

Ser Gly Val Pro Ser Arg Phe Ser Gly Ser Gly Ser Gly Thr Asp Tyr
        195                 200                 205
```

Thr Leu Thr Ile Ser Ser Leu Gln Pro Glu Asp Phe Ala Thr Tyr Tyr
            210                 215                 220

Cys Gln Gln Gly Asn Thr Leu Pro Trp Thr Phe Gly Gln Gly Thr Lys
225                 230                 235                 240

Val Glu Ile Lys

<210> SEQ ID NO 28
<211> LENGTH: 693
<212> TYPE: PRT
<213> ORGANISM: artificial
<220> FEATURE:
<223> OTHER INFORMATION: variant antibody sequence

<400> SEQUENCE: 28

Gln Val Gln Leu Val Gln Ser Gly Ala Glu Val Lys Lys Pro Gly Gly
1               5                   10                  15

Ser Leu Arg Leu Ser Cys Ala Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Thr Tyr Ala Gln Lys Phe
50                  55                  60

Lys Asp Arg Val Thr Ile Ser Arg Asp Thr Ser Lys Asn Thr Leu Tyr
65                  70                  75                  80

Leu Gln Leu Ser Ser Leu Arg Ala Glu Asp Thr Ala Val Tyr Tyr Cys
                85                  90                  95

Ala Arg Ala Ile Thr Thr Thr Pro Phe Asp Phe Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Gly Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

```
Cys Lys Val Ser Asn Lys Gln Leu Pro Ser Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys Ser
    435                 440                 445

Gly Asp Ile Gln Met Thr Gln Ser Pro Ser Ser Leu Ser Ala Ser Val
450                 455                 460

Gly Asp Arg Val Thr Ile Thr Cys Arg Ala Ser Gln Asp Ile Arg Asn
465                 470                 475                 480

Tyr Leu Asn Trp Tyr Gln Gln Lys Pro Gly Lys Ala Pro Lys Leu Leu
            485                 490                 495

Ile Tyr Tyr Thr Ser Arg Leu Glu Ser Gly Val Pro Ser Arg Phe Ser
        500                 505                 510

Gly Ser Gly Ser Gly Thr Asp Tyr Thr Leu Thr Ile Ser Ser Leu Gln
    515                 520                 525

Pro Glu Asp Phe Ala Thr Tyr Tyr Cys Gln Gln Gly Asn Thr Leu Pro
530                 535                 540

Trp Thr Phe Gly Gln Gly Thr Lys Val Glu Ile Lys Gly Gly Gly Gly
545                 550                 555                 560

Ser Gly Gly Gly Gly Ser Gly Gly Gly Ser Glu Val Gln Leu Val
                565                 570                 575

Glu Ser Gly Gly Gly Leu Val Gln Pro Gly Gly Ser Leu Arg Leu Ser
        580                 585                 590

Cys Ala Ala Ser Gly Tyr Ser Phe Thr Gly Tyr Thr Met Asn Trp Val
    595                 600                 605

Arg Gln Ala Pro Gly Lys Gly Leu Glu Trp Val Ala Leu Ile Asn Pro
610                 615                 620

Tyr Lys Gly Val Ser Thr Tyr Asn Gln Lys Phe Lys Asp Arg Phe Thr
625                 630                 635                 640

Ile Ser Val Asp Lys Ser Lys Asn Thr Ala Tyr Leu Gln Met Asn Ser
            645                 650                 655

Leu Arg Ala Glu Asp Thr Ala Val Tyr Tyr Cys Ala Arg Ser Gly Tyr
        660                 665                 670

Tyr Gly Asp Ser Asp Trp Tyr Phe Asp Val Trp Gly Gln Gly Thr Leu
    675                 680                 685

Val Thr Val Ser Ser
    690
```

<210> SEQ ID NO 29
<211> LENGTH: 214
<212> TYPE: PRT
<213> ORGANISM: artificial
<220> FEATURE:
<223> OTHER INFORMATION: variant antibody sequence

<400> SEQUENCE: 29

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Ala Ser Gln Ser Ala Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 30
<211> LENGTH: 693
<212> TYPE: PRT
<213> ORGANISM: artificial
<220> FEATURE:
<223> OTHER INFORMATION: variant antibody sequence

<400> SEQUENCE: 30

```
Gln Val Gln Leu Val Gln Ser Gly Ala Glu Val Lys Lys Pro Gly Gly
1               5                   10                  15

Ser Leu Arg Leu Ser Cys Ala Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Thr Asp Tyr Ala Gln Lys Phe
    50                  55                  60

Lys Asp Arg Val Thr Ile Ser Arg Asp Thr Ser Lys Asn Thr Leu Tyr
65                  70                  75                  80

Leu Gln Leu Ser Ser Leu Arg Ala Glu Asp Thr Ala Val Tyr Tyr Cys
                85                  90                  95

Ala Arg Ala Ile Thr Thr Thr Pro Phe Asp Phe Trp Gly Gln Gly Thr
            100                 105                 110

Leu Val Thr Val Ser Ser Ala Ser Thr Lys Gly Pro Ser Val Phe Pro
        115                 120                 125
```

```
Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Gly Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gln Leu Pro Ser Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Ser
        435                 440                 445

Gly Asp Ile Gln Met Thr Gln Ser Pro Ser Ser Leu Ser Ala Ser Val
        450                 455                 460

Gly Asp Arg Val Thr Ile Thr Cys Arg Ala Ser Gln Asp Ile Arg Asn
465                 470                 475                 480

Tyr Leu Asn Trp Tyr Gln Gln Lys Pro Gly Lys Ala Pro Lys Leu Leu
                485                 490                 495

Ile Tyr Tyr Thr Ser Arg Leu Glu Ser Gly Val Pro Ser Arg Phe Ser
                500                 505                 510

Gly Ser Gly Ser Gly Thr Asp Tyr Thr Leu Thr Ile Ser Ser Leu Gln
            515                 520                 525

Pro Glu Asp Phe Ala Thr Tyr Tyr Cys Gln Gln Gly Asn Thr Leu Pro
        530                 535                 540

Trp Thr Phe Gly Gln Gly Thr Lys Val Glu Ile Lys Gly Gly Gly Gly
```

```
                       545                 550                 555                 560
Ser Gly Gly Gly Ser Gly Gly Gly Ser Glu Val Gln Leu Val
                565                 570                 575

Glu Ser Gly Gly Gly Leu Val Gln Pro Gly Gly Ser Leu Arg Leu Ser
                580                 585                 590

Cys Ala Ala Ser Gly Tyr Ser Phe Thr Gly Tyr Thr Met Asn Trp Val
                595                 600                 605

Arg Gln Ala Pro Gly Lys Gly Leu Glu Trp Val Ala Leu Ile Asn Pro
            610                 615                 620

Tyr Lys Gly Val Ser Thr Tyr Asn Gln Lys Phe Lys Asp Arg Phe Thr
625                 630                 635                 640

Ile Ser Val Asp Lys Ser Lys Asn Thr Ala Tyr Leu Gln Met Asn Ser
                645                 650                 655

Leu Arg Ala Glu Asp Thr Ala Val Tyr Tyr Cys Ala Arg Ser Gly Tyr
                660                 665                 670

Tyr Gly Asp Ser Asp Trp Tyr Phe Asp Val Trp Gly Gln Gly Thr Leu
                675                 680                 685

Val Thr Val Ser Ser
                690

<210> SEQ ID NO 31
<211> LENGTH: 214
<212> TYPE: PRT
<213> ORGANISM: artificial
<220> FEATURE:
<223> OTHER INFORMATION: variant antibody sequence

<400> SEQUENCE: 31

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
                20                  25                  30

Leu His Trp Tyr Gln Gln Lys Pro Gly Gln Ala Pro Arg Leu Leu Ile
            35                  40                  45

Lys Tyr Ala Ser Gln Ser Ile Ser Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
```

<210> SEQ ID NO 32
<211> LENGTH: 693
<212> TYPE: PRT
<213> ORGANISM: artificial
<220> FEATURE:
<223> OTHER INFORMATION: variant antibody sequence

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Lys Asp Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Ile Thr Thr Thr Pro Phe Asp Phe Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Gly Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gln Leu Pro Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu

```
                355                 360                 365
Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Ser
        435                 440                 445

Gly Asp Ile Gln Met Thr Gln Ser Pro Ser Ser Leu Ser Ala Ser Val
    450                 455                 460

Gly Asp Arg Val Thr Ile Thr Cys Arg Ala Ser Gln Asp Ile Arg Asn
465                 470                 475                 480

Tyr Leu Asn Trp Tyr Gln Gln Lys Pro Gly Lys Ala Pro Lys Leu Leu
                485                 490                 495

Ile Tyr Tyr Thr Ser Arg Leu Glu Ser Gly Val Pro Ser Arg Phe Ser
            500                 505                 510

Gly Ser Gly Ser Gly Thr Asp Tyr Thr Leu Thr Ile Ser Ser Leu Gln
        515                 520                 525

Pro Glu Asp Phe Ala Thr Tyr Tyr Cys Gln Gln Gly Asn Thr Leu Pro
    530                 535                 540

Trp Thr Phe Gly Gln Gly Thr Lys Val Glu Ile Lys Gly Gly Gly Gly
545                 550                 555                 560

Ser Gly Gly Gly Gly Ser Gly Gly Gly Gly Ser Glu Val Gln Leu Val
                565                 570                 575

Glu Ser Gly Gly Gly Leu Val Gln Pro Gly Gly Ser Leu Arg Leu Ser
            580                 585                 590

Cys Ala Ala Ser Gly Tyr Ser Phe Thr Gly Tyr Thr Met Asn Trp Val
        595                 600                 605

Arg Gln Ala Pro Gly Lys Gly Leu Glu Trp Val Ala Leu Ile Asn Pro
    610                 615                 620

Tyr Lys Gly Val Ser Thr Tyr Asn Gln Lys Phe Lys Asp Arg Phe Thr
625                 630                 635                 640

Ile Ser Val Asp Lys Ser Lys Asn Thr Ala Tyr Leu Gln Met Asn Ser
                645                 650                 655

Leu Arg Ala Glu Asp Thr Ala Val Tyr Tyr Cys Ala Arg Ser Gly Tyr
            660                 665                 670

Tyr Gly Asp Ser Asp Trp Tyr Phe Asp Val Trp Gly Gln Gly Thr Leu
        675                 680                 685

Val Thr Val Ser Ser
    690

<210> SEQ ID NO 33
<211> LENGTH: 214
<212> TYPE: PRT
<213> ORGANISM: artificial
<220> FEATURE:
<223> OTHER INFORMATION: variant antibody sequence

<400> SEQUENCE: 33

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
```

```
                 20                  25                  30
Leu His Trp Tyr Gln Gln Lys Pro Gly Gln Ala Pro Arg Leu Leu Ile
             35                  40                  45

Tyr Tyr Ala Ser Gln Ser Ala Ser Gly Ile Pro Ala Arg Phe Ser Gly
         50                  55                  60

Ser Gly Ser Gly Thr Glu Phe Thr Leu Thr Ile Ser Ser Leu Gln Ser
 65                  70                  75                  80

Glu Asp Phe Ala Val Tyr Phe Cys Gln Gln Ser Asn Thr Trp Pro Tyr
                 85                  90                  95

Thr Phe Gly Gly Gly Thr Lys Leu Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                 165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu Cys
    210

<210> SEQ ID NO 34
<211> LENGTH: 693
<212> TYPE: PRT
<213> ORGANISM: artificial
<220> FEATURE:
<223> OTHER INFORMATION: variant antibody sequence

<400> SEQUENCE: 34

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Trp Met His Trp Val Arg Gln Ala Pro Gly Gln Gly Leu Glu Trp Ile
             35                  40                  45

Gly Glu Ile Asp Pro Ser Asp Ser Tyr Lys Asp Tyr Asn Gln Lys Phe
         50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ala Ile Thr Thr Thr Pro Phe Asp Phe Trp Gly Gln Gly Thr
             100                 105                 110

Thr Val Thr Val Ser Ser Ala Ser Thr Lys Gly Pro Ser Val Phe Pro
         115                 120                 125

Leu Ala Pro Ser Ser Lys Ser Thr Ser Gly Gly Thr Ala Ala Leu Gly
     130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
```

```
                165                 170                 175
Ser Ser Gly Leu Tyr Ser Leu Ser Ser Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Gly Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gln Leu Pro Ser Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys Ser
    435                 440                 445

Gly Asp Ile Gln Met Thr Gln Ser Pro Ser Ser Leu Ser Ala Ser Val
    450                 455                 460

Gly Asp Arg Val Thr Ile Thr Cys Arg Ala Ser Gln Asp Ile Arg Asn
465                 470                 475                 480

Tyr Leu Asn Trp Tyr Gln Gln Lys Pro Gly Lys Ala Pro Lys Leu Leu
                485                 490                 495

Ile Tyr Tyr Thr Ser Arg Leu Glu Ser Gly Val Pro Ser Arg Phe Ser
                500                 505                 510

Gly Ser Gly Ser Gly Thr Asp Tyr Thr Leu Thr Ile Ser Ser Leu Gln
                515                 520                 525

Pro Glu Asp Phe Ala Thr Tyr Tyr Cys Gln Gln Gly Asn Thr Leu Pro
    530                 535                 540

Trp Thr Phe Gly Gln Gly Thr Lys Val Glu Ile Lys Gly Gly Gly Gly
545                 550                 555                 560

Ser Gly Gly Gly Gly Ser Gly Gly Gly Ser Glu Val Gln Leu Val
                565                 570                 575

Glu Ser Gly Gly Gly Leu Val Gln Pro Gly Gly Ser Leu Arg Leu Ser
                580                 585                 590
```

```
Cys Ala Ala Ser Gly Tyr Ser Phe Thr Gly Tyr Thr Met Asn Trp Val
        595                 600                 605

Arg Gln Ala Pro Gly Lys Gly Leu Glu Trp Val Ala Leu Ile Asn Pro
    610                 615                 620

Tyr Lys Gly Val Ser Thr Tyr Asn Gln Lys Phe Lys Asp Arg Phe Thr
625                 630                 635                 640

Ile Ser Val Asp Lys Ser Lys Asn Thr Ala Tyr Leu Gln Met Asn Ser
                645                 650                 655

Leu Arg Ala Glu Asp Thr Ala Val Tyr Tyr Cys Ala Arg Ser Gly Tyr
            660                 665                 670

Tyr Gly Asp Ser Asp Trp Tyr Phe Asp Val Trp Gly Gln Gly Thr Leu
        675                 680                 685

Val Thr Val Ser Ser
        690

<210> SEQ ID NO 35
<211> LENGTH: 214
<212> TYPE: PRT
<213> ORGANISM: artificial
<220> FEATURE:
<223> OTHER INFORMATION: variant antibody sequence

<400> SEQUENCE: 35

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 36
<211> LENGTH: 693
<212> TYPE: PRT
<213> ORGANISM: artificial
```

```
<220> FEATURE:
<223> OTHER INFORMATION: variant antibody sequence

<400> SEQUENCE: 36

Gln Val Gln Leu Val Gln Ser Gly Ala Glu Val Lys Lys Pro Gly Gly
1               5                   10                  15

Ser Leu Arg Leu Ser Cys Ala Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Lys Asp Tyr Asn Gln Lys Phe
    50                  55                  60

Lys Asp Arg Val Thr Ile Ser Arg Asp Thr Ser Lys Asn Thr Leu Tyr
65                  70                  75                  80

Leu Gln Leu Ser Ser Leu Arg Ala Glu Asp Thr Ala Val Tyr Tyr Cys
                85                  90                  95

Ala Arg Ala Ile Thr Thr Thr Pro Phe Asp Phe Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Gly Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gln Leu Pro Ser Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Ser
        435                 440                 445

Gly Asp Ile Gln Met Thr Gln Ser Pro Ser Ser Leu Ser Ala Ser Val
    450                 455                 460

Gly Asp Arg Val Thr Ile Thr Cys Arg Ala Ser Gln Asp Ile Arg Asn
465                 470                 475                 480

Tyr Leu Asn Trp Tyr Gln Gln Lys Pro Gly Lys Ala Pro Lys Leu Leu
                485                 490                 495

Ile Tyr Tyr Thr Ser Arg Leu Glu Ser Gly Val Pro Ser Arg Phe Ser
            500                 505                 510

Gly Ser Gly Ser Gly Thr Asp Tyr Thr Leu Thr Ile Ser Ser Leu Gln
        515                 520                 525

Pro Glu Asp Phe Ala Thr Tyr Tyr Cys Gln Gln Gly Asn Thr Leu Pro
    530                 535                 540

Trp Thr Phe Gly Gln Gly Thr Lys Val Glu Ile Lys Gly Gly Gly Gly
545                 550                 555                 560

Ser Gly Gly Gly Gly Ser Gly Gly Gly Gly Ser Glu Val Gln Leu Val
                565                 570                 575

Glu Ser Gly Gly Gly Leu Val Gln Pro Gly Gly Ser Leu Arg Leu Ser
            580                 585                 590

Cys Ala Ala Ser Gly Tyr Ser Phe Thr Gly Tyr Thr Met Asn Trp Val
        595                 600                 605

Arg Gln Ala Pro Gly Lys Gly Leu Glu Trp Val Ala Leu Ile Asn Pro
    610                 615                 620

Tyr Lys Gly Val Ser Thr Tyr Asn Gln Lys Phe Lys Asp Arg Phe Thr
625                 630                 635                 640

Ile Ser Val Asp Lys Ser Lys Asn Thr Ala Tyr Leu Gln Met Asn Ser
                645                 650                 655

Leu Arg Ala Glu Asp Thr Ala Val Tyr Tyr Cys Ala Arg Ser Gly Tyr
            660                 665                 670

Tyr Gly Asp Ser Asp Trp Tyr Phe Asp Val Trp Gly Gln Gly Thr Leu
        675                 680                 685

Val Thr Val Ser Ser
    690

<210> SEQ ID NO 37
<211> LENGTH: 214
<212> TYPE: PRT
<213> ORGANISM: artificial
<220> FEATURE:
<223> OTHER INFORMATION: variant antibody sequence

<400> SEQUENCE: 37

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60
```

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 38
<211> LENGTH: 693
<212> TYPE: PRT
<213> ORGANISM: artificial
<220> FEATURE:
<223> OTHER INFORMATION: variant antibody sequence

<400> SEQUENCE: 38

Gln Val Gln Leu Val Gln Ser Gly Ala Glu Val Lys Lys Pro Gly Gly
1               5                   10                  15

Ser Leu Arg Leu Ser Cys Ala Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Thr Asp Tyr Ala Gln Lys Phe
    50                  55                  60

Lys Asp Arg Val Thr Ile Ser Arg Asp Thr Ser Lys Asn Thr Leu Tyr
65                  70                  75                  80

Leu Gln Leu Ser Ser Leu Arg Ala Glu Asp Thr Ala Val Tyr Tyr Cys
                85                  90                  95

Ala Arg Ala Ile Thr Thr Thr Pro Phe Asp Phe Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

```
Asn Thr Lys Val Asp Lys Lys Val Glu Pro Lys Ser Cys Asp Lys Thr
    210                 215                 220
His Thr Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
                260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Gln Leu Pro Ser Pro Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys Ser
            435                 440                 445
Gly Asp Ile Gln Met Thr Gln Ser Pro Ser Ser Leu Ser Ala Ser Val
450                 455                 460
Gly Asp Arg Val Thr Ile Thr Cys Arg Ala Ser Gln Asp Ile Arg Asn
465                 470                 475                 480
Tyr Leu Asn Trp Tyr Gln Gln Lys Pro Gly Lys Ala Pro Lys Leu Leu
                485                 490                 495
Ile Tyr Tyr Thr Ser Arg Leu Glu Ser Gly Val Pro Ser Arg Phe Ser
                500                 505                 510
Gly Ser Gly Ser Gly Thr Asp Tyr Thr Leu Thr Ile Ser Ser Leu Gln
            515                 520                 525
Pro Glu Asp Phe Ala Thr Tyr Tyr Cys Gln Gln Gly Asn Thr Leu Pro
530                 535                 540
Trp Thr Phe Gly Gln Gly Thr Lys Val Glu Ile Lys Gly Gly Gly Gly
545                 550                 555                 560
Ser Gly Gly Gly Gly Ser Gly Gly Gly Ser Glu Val Gln Leu Val
                565                 570                 575
Glu Ser Gly Gly Gly Leu Val Gln Pro Gly Gly Ser Leu Arg Leu Ser
            580                 585                 590
Cys Ala Ala Ser Gly Tyr Ser Phe Thr Gly Tyr Thr Met Asn Trp Val
            595                 600                 605
Arg Gln Ala Pro Gly Lys Gly Leu Glu Trp Val Ala Leu Ile Asn Pro
610                 615                 620
```

-continued

```
Tyr Lys Gly Val Ser Thr Tyr Ala Asp Ser Phe Lys Gly Arg Phe Thr
625                 630                 635                 640

Ile Ser Val Asp Asp Ser Lys Asn Thr Ala Tyr Leu Gln Met Asn Ser
            645                 650                 655

Leu Arg Ala Glu Asp Thr Ala Val Tyr Tyr Cys Ala Arg Ser Gly Tyr
        660                 665                 670

Tyr Gly Asp Ser Asp Trp Tyr Phe Asp Val Trp Gly Gln Gly Thr Leu
        675                 680                 685

Val Thr Val Ser Ser
        690
```

<210> SEQ ID NO 39
<211> LENGTH: 214
<212> TYPE: PRT
<213> ORGANISM: artificial
<220> FEATURE:
<223> OTHER INFORMATION: variant antibody sequence

<400> SEQUENCE: 39

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Ala Ser Gln Ser Ala Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 40
<211> LENGTH: 693
<212> TYPE: PRT
<213> ORGANISM: artificial
<220> FEATURE:
<223> OTHER INFORMATION: variant antibody sequence

<400> SEQUENCE: 40

```
Gln Val Gln Leu Val Gln Ser Gly Ala Glu Val Lys Lys Pro Gly Gly
1               5                   10                  15
```

```
Ser Leu Arg Leu Ser Cys Ala Ala Ser Gly Tyr Thr Phe Thr Ser Tyr
         20                  25                  30

Trp Met His Trp Val Arg Gln Ala Pro Gly Gln Gly Leu Glu Trp Ile
             35                  40                  45

Gly Glu Ile Asp Pro Ser Asp Ser Tyr Thr Asp Tyr Ala Gln Lys Phe
 50                  55                  60

Lys Asp Arg Val Thr Ile Ser Arg Asp Thr Ser Lys Asn Thr Leu Tyr
 65                  70                  75                  80

Leu Gln Leu Ser Ser Leu Arg Ala Glu Asp Thr Ala Val Tyr Tyr Cys
                 85                  90                  95

Ala Arg Ala Ile Thr Thr Thr Pro Phe Asp Phe Trp Gly Gln Gly Thr
             100                 105                 110

Leu Val Thr Val Ser Ser Ala Ser Thr Lys Gly Pro Ser Val Phe Pro
         115                 120                 125

Leu Ala Pro Ser Ser Lys Ser Thr Ser Gly Gly Thr Ala Ala Leu Gly
 130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                 165                 170                 175

Ser Ser Gly Leu Tyr Ser Leu Ser Ser Val Val Thr Val Pro Ser Ser
             180                 185                 190

Ser Leu Gly Thr Gln Thr Tyr Ile Cys Asn Val Asn His Lys Pro Ser
         195                 200                 205

Asn Thr Lys Val Asp Lys Lys Val Glu Pro Lys Ser Cys Asp Lys Thr
 210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                 245                 250                 255

Pro Glu Val Thr Cys Val Val Val Gly Val Ser His Glu Asp Pro Glu
             260                 265                 270

Val Lys Phe Asn Trp Tyr Val Asp Gly Val Glu Val His Asn Ala Lys
         275                 280                 285

Thr Lys Pro Arg Glu Glu Gln Tyr Asn Ser Thr Tyr Arg Val Val Ser
 290                 295                 300

Val Leu Thr Val Leu His Gln Asp Trp Leu Asn Gly Lys Glu Tyr Lys
305                 310                 315                 320

Cys Lys Val Ser Asn Lys Gln Leu Pro Ser Pro Ile Glu Lys Thr Ile
                 325                 330                 335

Ser Lys Ala Lys Gly Gln Pro Arg Glu Pro Gln Val Tyr Thr Leu Pro
             340                 345                 350

Pro Ser Arg Asp Glu Leu Thr Lys Asn Gln Val Ser Leu Thr Cys Leu
         355                 360                 365

Val Lys Gly Phe Tyr Pro Ser Asp Ile Ala Val Glu Trp Glu Ser Asn
 370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                 405                 410                 415

Trp Gln Gln Gly Asn Val Phe Ser Cys Ser Val Met His Glu Ala Leu
             420                 425                 430
```

-continued

His Asn His Tyr Thr Gln Lys Ser Leu Ser Leu Ser Pro Gly Lys Ser
                435                 440                 445

Gly Asp Ile Gln Met Thr Gln Ser Pro Ser Ser Leu Ser Ala Ser Val
        450                 455                 460

Gly Asp Arg Val Thr Ile Thr Cys Arg Ala Ser Gln Asp Ile Arg Asn
465                 470                 475                 480

Tyr Leu Asn Trp Tyr Gln Gln Lys Pro Gly Lys Ala Pro Lys Leu Leu
                485                 490                 495

Ile Tyr Tyr Thr Ser Arg Leu Glu Ser Gly Val Pro Ser Arg Phe Ser
            500                 505                 510

Gly Ser Gly Ser Gly Thr Asp Tyr Thr Leu Thr Ile Ser Ser Leu Gln
        515                 520                 525

Pro Glu Asp Phe Ala Thr Tyr Tyr Cys Gln Gln Gly Asn Thr Leu Pro
    530                 535                 540

Trp Thr Phe Gly Gln Gly Thr Lys Val Glu Ile Lys Gly Gly Gly Gly
545                 550                 555                 560

Ser Gly Gly Gly Gly Ser Gly Gly Gly Ser Glu Val Gln Leu Val
                565                 570                 575

Glu Ser Gly Gly Gly Leu Val Gln Pro Gly Gly Ser Leu Arg Leu Ser
            580                 585                 590

Cys Ala Ala Ser Gly Tyr Ser Phe Thr Gly Tyr Thr Met Asn Trp Val
        595                 600                 605

Arg Gln Ala Pro Gly Lys Gly Leu Glu Trp Val Ala Leu Ile Asn Pro
    610                 615                 620

Tyr Lys Gly Val Ser Thr Tyr Ala Asp Ser Phe Lys Gly Arg Phe Thr
625                 630                 635                 640

Ile Ser Val Asp Asp Ser Lys Asn Thr Ala Tyr Leu Gln Met Asn Ser
                645                 650                 655

Leu Arg Ala Glu Asp Thr Ala Val Tyr Tyr Cys Ala Arg Ser Gly Tyr
            660                 665                 670

Tyr Gly Asp Ser Asp Trp Tyr Phe Asp Val Trp Gly Gln Gly Thr Leu
        675                 680                 685

Val Thr Val Ser Ser
    690

<210> SEQ ID NO 41
<211> LENGTH: 214
<212> TYPE: PRT
<213> ORGANISM: artificial
<220> FEATURE:
<223> OTHER INFORMATION: variant antibody sequence

<400> SEQUENCE: 41

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

```
Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 42
<211> LENGTH: 693
<212> TYPE: PRT
<213> ORGANISM: artificial
<220> FEATURE:
<223> OTHER INFORMATION: variant antibody sequence

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Ile
            35                  40                  45

Gly Glu Ile Asp Pro Ser Asp Ser Tyr Lys Asp Tyr Asn Gln Lys Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Ile Thr Thr Thr Pro Phe Asp Phe Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Pro Val Ala Gly Pro Ser Val
225                 230                 235                 240
```

```
Phe Leu Phe Pro Pro Lys Pro Lys Asp Thr Leu Met Ile Ser Arg Thr
                    245                 250                 255

Pro Glu Val Thr Cys Val Val Val Gly Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gln Leu Pro Ser Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Ser
        435                 440                 445

Gly Asp Ile Gln Met Thr Gln Ser Pro Ser Ser Leu Ser Ala Ser Val
    450                 455                 460

Gly Asp Arg Val Thr Ile Thr Cys Arg Ala Ser Gln Asp Ile Arg Asn
465                 470                 475                 480

Tyr Leu Asn Trp Tyr Gln Gln Lys Pro Gly Lys Ala Pro Lys Leu Leu
                485                 490                 495

Ile Tyr Tyr Thr Ser Arg Leu Glu Ser Gly Val Pro Ser Arg Phe Ser
            500                 505                 510

Gly Ser Gly Ser Gly Thr Asp Tyr Thr Leu Thr Ile Ser Ser Leu Gln
        515                 520                 525

Pro Glu Asp Phe Ala Thr Tyr Tyr Cys Gln Gln Gly Asn Thr Leu Pro
    530                 535                 540

Trp Thr Phe Gly Gln Gly Thr Lys Val Glu Ile Lys Gly Gly Gly Gly
545                 550                 555                 560

Ser Gly Gly Gly Gly Ser Gly Gly Gly Gly Ser Glu Val Gln Leu Val
                565                 570                 575

Glu Ser Gly Gly Gly Leu Val Gln Pro Gly Gly Ser Leu Arg Leu Ser
            580                 585                 590

Cys Ala Ala Ser Gly Tyr Ser Phe Thr Gly Tyr Thr Met Asn Trp Val
        595                 600                 605

Arg Gln Ala Pro Gly Lys Gly Leu Glu Trp Val Ala Leu Ile Asn Pro
    610                 615                 620

Tyr Lys Gly Val Ser Thr Tyr Ala Asp Ser Phe Lys Gly Arg Phe Thr
625                 630                 635                 640

Ile Ser Val Asp Asp Ser Lys Asn Thr Ala Tyr Leu Gln Met Asn Ser
                645                 650                 655

Leu Arg Ala Glu Asp Thr Ala Val Tyr Tyr Cys Ala Arg Ser Gly Tyr
```

```
                    660                 665                 670
Tyr Gly Asp Ser Asp Trp Tyr Phe Asp Val Trp Gly Gln Gly Thr Leu
            675                 680                 685

Val Thr Val Ser Ser
        690

<210> SEQ ID NO 43
<211> LENGTH: 214
<212> TYPE: PRT
<213> ORGANISM: artificial
<220> FEATURE:
<223> OTHER INFORMATION: variant antibody sequence

<400> SEQUENCE: 43

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Ala Ser Gln Ser Ala Ser Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 44
<211> LENGTH: 693
<212> TYPE: PRT
<213> ORGANISM: artificial
<220> FEATURE:
<223> OTHER INFORMATION: variant antibody sequence

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45
```

```
Gly Glu Ile Asp Pro Ser Asp Ser Tyr Lys Asp Tyr Asn Gln Lys Phe
    50              55                  60
Lys Asp Arg Val Thr Met Thr Arg Asp Thr Ser Thr Ser Thr Val Tyr
 65              70                  75                  80
Met Glu Leu Ser Ser Leu Arg Ser Glu Asp Thr Ala Val Tyr Tyr Cys
                 85                  90                  95
Ala Arg Ala Ile Thr Thr Thr Pro Phe Asp Phe Trp Gly Gln Gly Thr
            100                 105                 110
Thr Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Gly Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gln Leu Pro Ser Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys Ser
            435                 440                 445
Gly Asp Ile Gln Met Thr Gln Ser Pro Ser Ser Leu Ser Ala Ser Val
    450                 455                 460
Gly Asp Arg Val Thr Ile Thr Cys Arg Ala Ser Gln Asp Ile Arg Asn
```

```
                    465                 470                 475                 480
Tyr Leu Asn Trp Tyr Gln Gln Lys Pro Gly Lys Ala Pro Lys Leu Leu
                485                 490                 495
Ile Tyr Tyr Thr Ser Arg Leu Glu Ser Gly Val Pro Ser Arg Phe Ser
                500                 505                 510
Gly Ser Gly Ser Gly Thr Asp Tyr Thr Leu Thr Ile Ser Ser Leu Gln
                515                 520                 525
Pro Glu Asp Phe Ala Thr Tyr Tyr Cys Gln Gln Gly Asn Thr Leu Pro
            530                 535                 540
Trp Thr Phe Gly Gln Gly Thr Lys Val Glu Ile Lys Gly Gly Gly Gly
545                 550                 555                 560
Ser Gly Gly Gly Gly Ser Gly Gly Gly Ser Glu Val Gln Leu Val
                565                 570                 575
Glu Ser Gly Gly Gly Leu Val Gln Pro Gly Gly Ser Leu Arg Leu Ser
            580                 585                 590
Cys Ala Ala Ser Gly Tyr Ser Phe Thr Gly Tyr Thr Met Asn Trp Val
            595                 600                 605
Arg Gln Ala Pro Gly Lys Gly Leu Glu Trp Val Ala Leu Ile Asn Pro
        610                 615                 620
Tyr Lys Gly Val Ser Thr Tyr Ala Asp Ser Phe Lys Gly Arg Phe Thr
625                 630                 635                 640
Ile Ser Val Asp Asp Ser Lys Asn Thr Ala Tyr Leu Gln Met Asn Ser
                645                 650                 655
Leu Arg Ala Glu Asp Thr Ala Val Tyr Tyr Cys Ala Arg Ser Gly Tyr
            660                 665                 670
Tyr Gly Asp Ser Asp Trp Tyr Phe Asp Val Trp Gly Gln Gly Thr Leu
        675                 680                 685
Val Thr Val Ser Ser
        690

<210> SEQ ID NO 45
<211> LENGTH: 214
<212> TYPE: PRT
<213> ORGANISM: artificial
<220> FEATURE:
<223> OTHER INFORMATION: variant antibody sequence

<400> SEQUENCE: 45

Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Ile Ser Asn Asn
            20                  25                  30
Leu His Trp Tyr Gln Gln Lys Pro Gly Gln Ala Pro Arg Leu Leu Ile
        35                  40                  45
Lys Tyr Ala Ser Gln Ser Ile Ser Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Phe Cys Gln Gln Ser Asn Thr Trp Pro Tyr
                85                  90                  95
Thr Phe Gly Gly Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
```

```
            130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 46
<211> LENGTH: 693
<212> TYPE: PRT
<213> ORGANISM: artificial
<220> FEATURE:
<223> OTHER INFORMATION: variant antibody sequence

<400> SEQUENCE: 46

Gln Val Gln Leu Val Gln Ser Gly Ala Glu Val Lys Lys Pro Gly Gly
1               5                   10                  15

Ser Leu Arg Leu Ser Cys Ala Ala Ser Gly Tyr Thr Phe Thr Ser Tyr
                20                  25                  30

Trp Met His Trp Val Arg Gln Ala Pro Gly Gln Gly Leu Glu Trp Ile
                35                  40                  45

Gly Glu Ile Asp Pro Ser Asp Ser Tyr Lys Asp Tyr Asn Gln Lys Phe
    50                  55                  60

Lys Asp Arg Val Thr Ile Ser Arg Asp Thr Ser Lys Asn Thr Leu Tyr
65                  70                  75                  80

Leu Gln Leu Ser Ser Leu Arg Ala Glu Asp Thr Ala Val Tyr Tyr Cys
                85                  90                  95

Ala Arg Ala Ile Thr Thr Thr Pro Phe Asp Phe Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Gly Val Ser His Glu Asp Pro Glu
                260                 265                 270

Val Lys Phe Asn Trp Tyr Val Asp Gly Val Glu Val His Asn Ala Lys
```

```
            275                 280                 285
Thr Lys Pro Arg Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Gln Leu Pro Ser Pro Ile Glu Lys Thr Ile
                    325                 330                 335
Ser Lys Ala Lys Gly Gln Pro Arg Glu Pro Gln Val Tyr Thr Leu Pro
                340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                    405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly Lys Ser
            435                 440                 445
Gly Asp Ile Gln Met Thr Gln Ser Pro Ser Ser Leu Ser Ala Ser Val
450                 455                 460
Gly Asp Arg Val Thr Ile Thr Cys Arg Ala Ser Gln Asp Ile Arg Asn
465                 470                 475                 480
Tyr Leu Asn Trp Tyr Gln Gln Lys Pro Gly Lys Ala Pro Lys Leu Leu
                    485                 490                 495
Ile Tyr Tyr Thr Ser Arg Leu Glu Ser Gly Val Pro Ser Arg Phe Ser
                500                 505                 510
Gly Ser Gly Ser Gly Thr Asp Tyr Thr Leu Thr Ile Ser Ser Leu Gln
            515                 520                 525
Pro Glu Asp Phe Ala Thr Tyr Tyr Cys Gln Gln Gly Asn Thr Leu Pro
530                 535                 540
Trp Thr Phe Gly Gln Gly Thr Lys Val Glu Ile Lys Gly Gly Gly Gly
545                 550                 555                 560
Ser Gly Gly Gly Gly Ser Gly Gly Gly Ser Glu Val Gln Leu Val
                    565                 570                 575
Glu Ser Gly Gly Gly Leu Val Gln Pro Gly Gly Ser Leu Arg Leu Ser
                580                 585                 590
Cys Ala Ala Ser Gly Tyr Ser Phe Thr Gly Tyr Thr Met Asn Trp Val
            595                 600                 605
Arg Gln Ala Pro Gly Lys Gly Leu Glu Trp Val Ala Leu Ile Asn Pro
610                 615                 620
Tyr Lys Gly Val Ser Thr Tyr Ala Asp Ser Phe Lys Gly Arg Phe Thr
625                 630                 635                 640
Ile Ser Val Asp Asp Ser Lys Asn Thr Ala Tyr Leu Gln Met Asn Ser
                    645                 650                 655
Leu Arg Ala Glu Asp Thr Ala Val Tyr Tyr Cys Ala Arg Ser Gly Tyr
                660                 665                 670
Tyr Gly Asp Ser Asp Trp Tyr Phe Asp Val Trp Gly Gln Gly Thr Leu
            675                 680                 685
Val Thr Val Ser Ser
            690
```

<210> SEQ ID NO 47
<211> LENGTH: 214
<212> TYPE: PRT
<213> ORGANISM: artificial
<220> FEATURE:
<223> OTHER INFORMATION: variant antibody sequence

<400> SEQUENCE: 47

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 48
<211> LENGTH: 693
<212> TYPE: PRT
<213> ORGANISM: artificial
<220> FEATURE:
<223> OTHER INFORMATION: variant antibody sequence

<400> SEQUENCE: 48

Gln Val Gln Leu Val Gln Ser Gly Ala Glu Val Lys Lys Pro Gly Gly
1               5                   10                  15

Ser Leu Arg Leu Ser Cys Ala Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Thr Asp Tyr Ala Gln Lys Phe
    50                  55                  60

Lys Asp Arg Val Thr Ile Ser Arg Asp Thr Ser Lys Asn Thr Leu Tyr
65                  70                  75                  80

Leu Gln Leu Ser Ser Leu Arg Ala Glu Asp Thr Ala Val Tyr Tyr Cys

-continued

```
                85                  90                  95
Ala Arg Ala Ile Thr Thr Thr Pro Phe Asp Phe Trp Gly Gln Gly Thr
                100                 105                 110
Leu Val Thr Val Ser Ser Ala Ser Thr Lys Gly Pro Ser Val Phe Pro
                115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Lys Val Glu Pro Lys Ser Cys Asp Lys Thr
        210                 215                 220
His Thr Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Gly Val Ser His Glu Asp Pro Glu
                260                 265                 270
Val Lys Phe Asn Trp Tyr Val Asp Gly Val Glu Val His Asn Ala Lys
                275                 280                 285
Thr Lys Pro Arg Glu Glu Gln Tyr Asn Ser Thr Tyr Arg Val Val Ser
        290                 295                 300
Val Leu Thr Val Leu His Gln Asp Trp Leu Asn Gly Lys Glu Tyr Lys
305                 310                 315                 320
Cys Lys Val Ser Asn Lys Gln Leu Pro Ser Pro Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Arg Asp Glu Leu Thr Lys Asn Gln Val Ser Leu Thr Cys Leu
                355                 360                 365
Val Lys Gly Phe Tyr Pro Ser Asp Ile Ala Val Glu Trp Glu Ser Asn
        370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly Lys Ser
                435                 440                 445
Gly Asp Ile Gln Met Thr Gln Ser Pro Ser Ser Leu Ser Ala Ser Val
        450                 455                 460
Gly Asp Arg Val Thr Ile Thr Cys Arg Ala Ser Gln Asp Ile Arg Asn
465                 470                 475                 480
Tyr Leu Asn Trp Tyr Gln Gln Lys Pro Gly Lys Ala Pro Lys Leu Leu
                485                 490                 495
Ile Tyr Tyr Thr Ser Arg Leu Glu Ser Gly Val Pro Ser Arg Phe Ser
                500                 505                 510
```

Gly Ser Gly Ser Gly Thr Asp Tyr Thr Leu Thr Ile Ser Ser Leu Gln
            515                 520                 525

Pro Glu Asp Phe Ala Thr Tyr Tyr Cys Gln Gln Gly Asn Thr Leu Pro
    530                 535                 540

Trp Thr Phe Gly Gln Gly Thr Lys Val Glu Ile Lys Gly Gly Gly Gly
545                 550                 555                 560

Ser Gly Gly Gly Ser Gly Gly Gly Ser Glu Val Gln Leu Val
                565                 570                 575

Glu Ser Gly Gly Gly Leu Val Gln Pro Gly Gly Ser Leu Arg Leu Ser
            580                 585                 590

Cys Ala Ala Ser Gly Tyr Ser Phe Thr Gly Tyr Thr Met Asn Trp Val
            595                 600                 605

Arg Gln Ala Pro Gly Lys Gly Leu Glu Trp Val Ala Leu Ile Asn Pro
    610                 615                 620

Tyr Lys Gly Val Ser Thr Tyr Asn Gln Lys Phe Lys Asp Arg Phe Thr
625                 630                 635                 640

Ile Ser Val Asp Asp Ser Lys Asn Thr Ala Tyr Leu Gln Met Asn Ser
                645                 650                 655

Leu Arg Ala Glu Asp Thr Ala Val Tyr Tyr Cys Ala Arg Ser Gly Tyr
            660                 665                 670

Tyr Gly Asp Ser Asp Trp Tyr Phe Asp Val Trp Gly Gln Gly Thr Leu
            675                 680                 685

Val Thr Val Ser Ser
            690

<210> SEQ ID NO 49
<211> LENGTH: 214
<212> TYPE: PRT
<213> ORGANISM: artificial
<220> FEATURE:
<223> OTHER INFORMATION: variant antibody sequence

<400> SEQUENCE: 49

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Ala Ser Gln Ser Ala Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 50
<211> LENGTH: 693
<212> TYPE: PRT
<213> ORGANISM: artificial
<220> FEATURE:
<223> OTHER INFORMATION: variant antibody sequence

<400> SEQUENCE: 50

Gln Val Gln Leu Val Gln Ser Gly Ala Glu Val Lys Lys Pro Gly Gly
1               5                   10                  15

Ser Leu Arg Leu Ser Cys Ala Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Thr Asp Tyr Ala Gln Lys Phe
    50                  55                  60

Lys Asp Arg Val Thr Ile Ser Arg Asp Thr Ser Lys Asn Thr Leu Tyr
65                  70                  75                  80

Leu Gln Leu Ser Ser Leu Arg Ala Glu Asp Thr Ala Val Tyr Tyr Cys
            85                  90                  95

Ala Arg Ala Ile Thr Thr Thr Pro Phe Asp Phe Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Pro Ala Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Gly Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Gln Leu Pro Ser Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Ser
            435                 440                 445

Gly Asp Ile Gln Met Thr Gln Ser Pro Ser Ser Leu Ser Ala Ser Val
450                 455                 460

Gly Asp Arg Val Thr Ile Thr Cys Arg Ala Ser Gln Asp Ile Arg Asn
465                 470                 475                 480

Tyr Leu Asn Trp Tyr Gln Gln Lys Pro Gly Lys Ala Pro Lys Leu Leu
                485                 490                 495

Ile Tyr Tyr Thr Ser Arg Leu Glu Ser Gly Val Pro Ser Arg Phe Ser
            500                 505                 510

Gly Ser Gly Ser Gly Thr Asp Tyr Thr Leu Thr Ile Ser Ser Leu Gln
            515                 520                 525

Pro Glu Asp Phe Ala Thr Tyr Tyr Cys Gln Gln Gly Asn Thr Leu Pro
            530                 535                 540

Trp Thr Phe Gly Gln Gly Thr Lys Val Glu Ile Lys Gly Gly Gly Gly
545                 550                 555                 560

Ser Gly Gly Gly Gly Ser Gly Gly Gly Ser Glu Val Gln Leu Val
                565                 570                 575

Glu Ser Gly Gly Gly Leu Val Gln Pro Gly Gly Ser Leu Arg Leu Ser
            580                 585                 590

Cys Ala Ala Ser Gly Tyr Ser Phe Thr Gly Tyr Thr Met Asn Trp Val
            595                 600                 605

Arg Gln Ala Pro Gly Lys Gly Leu Glu Trp Val Ala Leu Ile Asn Pro
610                 615                 620

Tyr Lys Gly Val Ser Thr Tyr Asn Gln Lys Phe Lys Asp Arg Phe Thr
625                 630                 635                 640

Ile Ser Val Asp Asp Ser Lys Asn Thr Ala Tyr Leu Gln Met Asn Ser
                645                 650                 655

Leu Arg Ala Glu Asp Thr Ala Val Tyr Tyr Cys Ala Arg Ser Gly Tyr
            660                 665                 670

Tyr Gly Asp Ser Asp Trp Tyr Phe Asp Val Trp Gly Gln Gly Thr Leu
            675                 680                 685

Val Thr Val Ser Ser
    690

<210> SEQ ID NO 51
<211> LENGTH: 214
<212> TYPE: PRT
<213> ORGANISM: artificial
<220> FEATURE:
```

<223> OTHER INFORMATION: variant antibody sequence

<400> SEQUENCE: 51

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 52
<211> LENGTH: 693
<212> TYPE: PRT
<213> ORGANISM: artificial
<220> FEATURE:
<223> OTHER INFORMATION: variant antibody sequence

<400> SEQUENCE: 52

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Lys Asp Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Ile Thr Thr Thr Pro Phe Asp Phe Trp Gly Gln Gly Thr
            100                 105                 110

Thr Val Thr Val Ser Ser Ala Ser Thr Lys Gly Pro Ser Val Phe Pro
        115                 120                 125
```

```
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
            195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Gly Val Ser His Glu Asp Pro Glu
                260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gln Leu Pro Ser Pro Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly Lys Ser
            435                 440                 445
Gly Asp Ile Gln Met Thr Gln Ser Pro Ser Ser Leu Ser Ala Ser Val
    450                 455                 460
Gly Asp Arg Val Thr Ile Thr Cys Arg Ala Ser Gln Asp Ile Arg Asn
465                 470                 475                 480
Tyr Leu Asn Trp Tyr Gln Gln Lys Pro Gly Lys Ala Pro Lys Leu Leu
                485                 490                 495
Ile Tyr Tyr Thr Ser Arg Leu Glu Ser Gly Val Pro Ser Arg Phe Ser
                500                 505                 510
Gly Ser Gly Ser Gly Thr Asp Tyr Thr Leu Thr Ile Ser Ser Leu Gln
            515                 520                 525
Pro Glu Asp Phe Ala Thr Tyr Tyr Cys Gln Gln Gly Asn Thr Leu Pro
    530                 535                 540
```

```
Trp Thr Phe Gly Gln Gly Thr Lys Val Glu Ile Lys Gly Gly Gly
545                 550                 555                 560

Ser Gly Gly Gly Ser Gly Gly Gly Ser Glu Val Gln Leu Val
                565                 570                 575

Glu Ser Gly Gly Gly Leu Val Gln Pro Gly Gly Ser Leu Arg Leu Ser
            580                 585                 590

Cys Ala Ala Ser Gly Tyr Ser Phe Thr Gly Tyr Thr Met Asn Trp Val
        595                 600                 605

Arg Gln Ala Pro Gly Lys Gly Leu Glu Trp Val Ala Leu Ile Asn Pro
        610                 615                 620

Tyr Lys Gly Val Ser Thr Tyr Asn Gln Lys Phe Lys Asp Arg Phe Thr
625                 630                 635                 640

Ile Ser Val Asp Asp Ser Lys Asn Thr Ala Tyr Leu Gln Met Asn Ser
                645                 650                 655

Leu Arg Ala Glu Asp Thr Ala Val Tyr Tyr Cys Ala Arg Ser Gly Tyr
            660                 665                 670

Tyr Gly Asp Ser Asp Trp Tyr Phe Asp Val Trp Gly Gln Gly Thr Leu
        675                 680                 685

Val Thr Val Ser Ser
    690
```

<210> SEQ ID NO 53
<211> LENGTH: 214
<212> TYPE: PRT
<213> ORGANISM: artificial
<220> FEATURE:
<223> OTHER INFORMATION: variant antibody sequence

<400> SEQUENCE: 53

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Ala Ser Gln Ser Ala Ser Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
            85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205
```

```
Phe Asn Arg Gly Glu Cys
    210

<210> SEQ ID NO 54
<211> LENGTH: 693
<212> TYPE: PRT
<213> ORGANISM: artificial
<220> FEATURE:
<223> OTHER INFORMATION: variant antibody sequence

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Ile
            35                  40                  45

Gly Glu Ile Asp Pro Ser Asp Ser Tyr Lys Asp Tyr Asn Gln Lys Phe
        50                  55                  60

Lys Asp Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Ile Thr Thr Thr Pro Phe Asp Phe Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Gly Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gln Leu Pro Ser Pro Ile Glu Lys Thr Ile
                325                 330                 335

Ser Lys Ala Lys Gly Gln Pro Arg Glu Pro Gln Val Tyr Thr Leu Pro
            340                 345                 350
```

```
Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys Ser
            435                 440                 445

Gly Asp Ile Gln Met Thr Gln Ser Pro Ser Ser Leu Ser Ala Ser Val
            450                 455                 460

Gly Asp Arg Val Thr Ile Thr Cys Arg Ala Ser Gln Asp Ile Arg Asn
465                 470                 475                 480

Tyr Leu Asn Trp Tyr Gln Gln Lys Pro Gly Lys Ala Pro Lys Leu Leu
                485                 490                 495

Ile Tyr Tyr Thr Ser Arg Leu Glu Ser Gly Val Pro Ser Arg Phe Ser
            500                 505                 510

Gly Ser Gly Ser Gly Thr Asp Tyr Thr Leu Thr Ile Ser Ser Leu Gln
            515                 520                 525

Pro Glu Asp Phe Ala Thr Tyr Tyr Cys Gln Gln Gly Asn Thr Leu Pro
            530                 535                 540

Trp Thr Phe Gly Gln Gly Thr Lys Val Glu Ile Lys Gly Gly Gly Gly
545                 550                 555                 560

Ser Gly Gly Gly Gly Ser Gly Gly Gly Gly Ser Glu Val Gln Leu Val
                565                 570                 575

Glu Ser Gly Gly Gly Leu Val Gln Pro Gly Gly Ser Leu Arg Leu Ser
            580                 585                 590

Cys Ala Ala Ser Gly Tyr Ser Phe Thr Gly Tyr Thr Met Asn Trp Val
            595                 600                 605

Arg Gln Ala Pro Gly Lys Gly Leu Glu Trp Val Ala Leu Ile Asn Pro
610                 615                 620

Tyr Lys Gly Val Ser Thr Tyr Asn Gln Lys Phe Lys Asp Arg Phe Thr
625                 630                 635                 640

Ile Ser Val Asp Asp Ser Lys Asn Thr Ala Tyr Leu Gln Met Asn Ser
                645                 650                 655

Leu Arg Ala Glu Asp Thr Ala Val Tyr Tyr Cys Ala Arg Ser Gly Tyr
            660                 665                 670

Tyr Gly Asp Ser Asp Trp Tyr Phe Asp Val Trp Gly Gln Gly Thr Leu
            675                 680                 685

Val Thr Val Ser Ser
            690

<210> SEQ ID NO 55
<211> LENGTH: 214
<212> TYPE: PRT
<213> ORGANISM: artificial
<220> FEATURE:
<223> OTHER INFORMATION: variant antibody sequence

<400> SEQUENCE: 55

Glu Ile Val Met Thr Gln Ser Pro Ala Thr Leu Ser Val Ser Pro Gly
1               5                   10                  15
```

-continued

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
            35                  40                  45

Lys Tyr Ala Ser Gln Ser Ile Ser Gly Ile Pro Ala Arg Phe Ser Gly
50                      55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 56
<211> LENGTH: 693
<212> TYPE: PRT
<213> ORGANISM: artificial
<220> FEATURE:
<223> OTHER INFORMATION: variant antibody sequence

<400> SEQUENCE: 56

Gln Val Gln Leu Val Gln Ser Gly Ala Glu Val Lys Lys Pro Gly Gly
1               5                   10                  15

Ser Leu Arg Leu Ser Cys Ala Ala Ser Gly Tyr Thr Phe Thr Ser Tyr
            20                  25                  30

Trp Met His Trp Val Arg Gln Ala Pro Gly Gln Gly Leu Glu Trp Ile
            35                  40                  45

Gly Glu Ile Asp Pro Ser Ser Tyr Lys Asp Tyr Asn Gln Lys Phe
        50                  55                  60

Lys Asp Arg Val Thr Ile Ser Arg Asp Thr Ser Lys Asn Thr Leu Tyr
65                  70                  75                  80

Leu Gln Leu Ser Ser Leu Arg Ala Glu Asp Thr Ala Val Tyr Tyr Cys
                85                  90                  95

Ala Arg Ala Ile Thr Thr Thr Pro Phe Asp Phe Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Val Ala Gly Pro Ser Val
225             230                 235                 240

Phe Leu Phe Pro Pro Lys Pro Lys Asp Thr Leu Met Ile Ser Arg Thr
            245                 250                 255

Pro Glu Val Thr Cys Val Val Val Gly Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305             310                 315                 320

Cys Lys Val Ser Asn Lys Gln Leu Pro Ser Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370             375                 380

Gly Gln Pro Glu Asn Asn Tyr Lys Thr Thr Pro Pro Val Leu Asp Ser
385             390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Ser
            435                 440                 445

Gly Asp Ile Gln Met Thr Gln Ser Pro Ser Ser Leu Ser Ala Ser Val
            450                 455                 460

Gly Asp Arg Val Thr Ile Thr Cys Arg Ala Ser Gln Asp Ile Arg Asn
465             470                 475                 480

Tyr Leu Asn Trp Tyr Gln Gln Lys Pro Gly Lys Ala Pro Lys Leu Leu
            485                 490                 495

Ile Tyr Tyr Thr Ser Arg Leu Glu Ser Gly Val Pro Ser Arg Phe Ser
            500                 505                 510

Gly Ser Gly Ser Gly Thr Asp Tyr Thr Leu Thr Ile Ser Ser Leu Gln
            515                 520                 525

Pro Glu Asp Phe Ala Thr Tyr Tyr Cys Gln Gln Gly Asn Thr Leu Pro
            530                 535                 540

Trp Thr Phe Gly Gln Gly Thr Lys Val Glu Ile Lys Gly Gly Gly Gly
545             550                 555                 560

Ser Gly Gly Gly Gly Ser Gly Gly Gly Ser Glu Val Gln Leu Val
            565                 570                 575

Glu Ser Gly Gly Gly Leu Val Gln Pro Gly Gly Ser Leu Arg Leu Ser

```
                580             585             590
Cys Ala Ala Ser Gly Tyr Ser Phe Thr Gly Tyr Thr Met Asn Trp Val
            595             600             605

Arg Gln Ala Pro Gly Lys Gly Leu Glu Trp Val Ala Leu Ile Asn Pro
    610             615             620

Tyr Lys Gly Val Ser Thr Tyr Asn Gln Lys Phe Lys Asp Arg Phe Thr
625             630             635             640

Ile Ser Val Asp Asp Ser Lys Asn Thr Ala Tyr Leu Gln Met Asn Ser
            645             650             655

Leu Arg Ala Glu Asp Thr Ala Val Tyr Tyr Cys Ala Arg Ser Gly Tyr
        660             665             670

Tyr Gly Asp Ser Asp Trp Tyr Phe Asp Val Trp Gly Gln Gly Thr Leu
    675             680             685

Val Thr Val Ser Ser
    690

<210> SEQ ID NO 57
<211> LENGTH: 214
<212> TYPE: PRT
<213> ORGANISM: artificial
<220> FEATURE:
<223> OTHER INFORMATION: variant antibody sequence

<400> SEQUENCE: 57

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 58
<211> LENGTH: 693
<212> TYPE: PRT
```

```
<213> ORGANISM: artificial
<220> FEATURE:
<223> OTHER INFORMATION: variant antibody sequence

<400> SEQUENCE: 58

Gln Val Gln Leu Val Gln Ser Gly Ala Glu Val Lys Lys Pro Gly Gly
1               5                   10                  15

Ser Leu Arg Leu Ser Cys Ala Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Thr Tyr Ala Gln Lys Phe
    50                  55                  60

Lys Asp Arg Val Thr Ile Ser Arg Asp Thr Ser Lys Asn Thr Leu Tyr
65                  70                  75                  80

Leu Gln Leu Ser Ser Leu Arg Ala Glu Asp Thr Ala Val Tyr Tyr Cys
                85                  90                  95

Ala Arg Ala Ile Thr Thr Thr Pro Phe Asp Phe Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Gly Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gln Leu Pro Ser Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
```

```
                385                 390                 395                 400
Asp Gly Ser Phe Phe Leu Tyr Ser Lys Leu Thr Val Asp Lys Ser Arg
                    405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Ser
        435                 440                 445

Gly Glu Val Gln Leu Val Glu Ser Gly Gly Leu Val Gln Pro Gly
    450                 455                 460

Gly Ser Leu Arg Leu Ser Cys Ala Ala Ser Gly Tyr Ser Phe Thr Gly
465                 470                 475                 480

Tyr Thr Met Asn Trp Val Arg Gln Ala Pro Gly Lys Gly Leu Glu Trp
                485                 490                 495

Val Ala Leu Ile Asn Pro Tyr Lys Gly Val Ser Thr Tyr Asn Gln Lys
            500                 505                 510

Phe Lys Asp Arg Phe Thr Ile Ser Val Asp Lys Ser Lys Asn Thr Ala
        515                 520                 525

Tyr Leu Gln Met Asn Ser Leu Arg Ala Glu Asp Thr Ala Val Tyr Tyr
    530                 535                 540

Cys Ala Arg Ser Gly Tyr Tyr Gly Asp Ser Asp Trp Tyr Phe Asp Val
545                 550                 555                 560

Trp Gly Gln Gly Thr Leu Val Thr Val Ser Ser Gly Gly Gly Gly Ser
                565                 570                 575

Gly Gly Gly Gly Ser Gly Gly Gly Gly Ser Asp Ile Gln Met Thr Gln
            580                 585                 590

Ser Pro Ser Ser Leu Ser Ala Ser Val Gly Asp Arg Val Thr Ile Thr
        595                 600                 605

Cys Arg Ala Ser Gln Asp Ile Arg Asn Tyr Leu Asn Trp Tyr Gln Gln
    610                 615                 620

Lys Pro Gly Lys Ala Pro Lys Leu Leu Ile Tyr Tyr Thr Ser Arg Leu
625                 630                 635                 640

Glu Ser Gly Val Pro Ser Arg Phe Ser Gly Ser Gly Ser Gly Thr Asp
                645                 650                 655

Tyr Thr Leu Thr Ile Ser Ser Leu Gln Pro Glu Asp Phe Ala Thr Tyr
            660                 665                 670

Tyr Cys Gln Gln Gly Asn Thr Leu Pro Trp Thr Phe Gly Gln Gly Thr
        675                 680                 685

Lys Val Glu Ile Lys
    690

<210> SEQ ID NO 59
<211> LENGTH: 214
<212> TYPE: PRT
<213> ORGANISM: artificial
<220> FEATURE:
<223> OTHER INFORMATION: variant antibody sequence

<400> SEQUENCE: 59

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Ala Ser Gln Ser Ala Ser Gly Ile Pro Ala Arg Phe Ser Gly
```

```
                 50                   55                  60
Ser Gly Ser Gly Thr Glu Phe Thr Leu Thr Ile Ser Ser Leu Gln Ser
 65                  70                  75                  80

Glu Asp Phe Ala Val Tyr Phe Cys Gln Gln Ser Asn Thr Trp Pro Tyr
                     85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 60
<211> LENGTH: 693
<212> TYPE: PRT
<213> ORGANISM: artificial
<220> FEATURE:
<223> OTHER INFORMATION: variant antibody sequence

<400> SEQUENCE: 60

Gln Val Gln Leu Val Gln Ser Gly Ala Glu Val Lys Lys Pro Gly Gly
 1                   5                  10                  15

Ser Leu Arg Leu Ser Cys Ala Ala Ser Gly Tyr Thr Phe Thr Ser Tyr
                 20                  25                  30

Trp Met His Trp Val Arg Gln Ala Pro Gly Gln Gly Leu Glu Trp Ile
             35                  40                  45

Gly Glu Ile Asp Pro Ser Asp Ser Tyr Thr Tyr Ala Gln Lys Phe
 50                  55                  60

Lys Asp Arg Val Thr Ile Ser Arg Asp Thr Ser Lys Asn Thr Leu Tyr
 65                  70                  75                  80

Leu Gln Leu Ser Ser Leu Arg Ala Glu Asp Thr Ala Val Tyr Tyr Cys
                 85                  90                  95

Ala Arg Ala Ile Thr Thr Thr Pro Phe Asp Phe Trp Gly Gln Gly Thr
                100                 105                 110

Leu Val Thr Val Ser Ser Ala Ser Thr Lys Gly Pro Ser Val Phe Pro
             115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
             180                 185                 190

Ser Leu Gly Thr Gln Thr Tyr Ile Cys Asn Val Asn His Lys Pro Ser
```

```
            195                 200                 205
Asn Thr Lys Val Asp Lys Lys Val Glu Pro Lys Ser Cys Asp Lys Thr
210                 215                 220

His Thr Cys Pro Pro Cys Pro Ala Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gln Leu Pro Ser Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys Ser
            435                 440                 445

Gly Glu Val Gln Leu Val Glu Ser Gly Gly Gly Leu Val Gln Pro Gly
450                 455                 460

Gly Ser Leu Arg Leu Ser Cys Ala Ala Ser Gly Tyr Ser Phe Thr Gly
465                 470                 475                 480

Tyr Thr Met Asn Trp Val Arg Gln Ala Pro Gly Lys Gly Leu Glu Trp
                485                 490                 495

Val Ala Leu Ile Asn Pro Tyr Lys Gly Val Ser Thr Tyr Asn Gln Lys
                500                 505                 510

Phe Lys Asp Arg Phe Thr Ile Ser Val Asp Lys Ser Lys Asn Thr Ala
            515                 520                 525

Tyr Leu Gln Met Asn Ser Leu Arg Ala Glu Asp Thr Ala Val Tyr Tyr
        530                 535                 540

Cys Ala Arg Ser Gly Tyr Tyr Gly Asp Ser Asp Trp Tyr Phe Asp Val
545                 550                 555                 560

Trp Gly Gln Gly Thr Leu Val Thr Val Ser Ser Gly Gly Gly Gly Ser
                565                 570                 575

Gly Gly Gly Gly Ser Gly Gly Gly Ser Asp Ile Gln Met Thr Gln
                580                 585                 590

Ser Pro Ser Ser Leu Ser Ala Ser Val Gly Asp Arg Val Thr Ile Thr
            595                 600                 605

Cys Arg Ala Ser Gln Asp Ile Arg Asn Tyr Leu Asn Trp Tyr Gln Gln
610                 615                 620
```

```
Lys Pro Gly Lys Ala Pro Lys Leu Leu Ile Tyr Tyr Thr Ser Arg Leu
625                 630                 635                 640

Glu Ser Gly Val Pro Ser Arg Phe Ser Gly Ser Gly Ser Gly Thr Asp
                645                 650                 655

Tyr Thr Leu Thr Ile Ser Ser Leu Gln Pro Glu Asp Phe Ala Thr Tyr
            660                 665                 670

Tyr Cys Gln Gln Gly Asn Thr Leu Pro Trp Thr Phe Gly Gln Gly Thr
        675                 680                 685

Lys Val Glu Ile Lys
    690

<210> SEQ ID NO 61
<211> LENGTH: 214
<212> TYPE: PRT
<213> ORGANISM: artificial
<220> FEATURE:
<223> OTHER INFORMATION: variant antibody sequence

<400> SEQUENCE: 61

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
                20                  25                  30

Leu His Trp Tyr Gln Gln Lys Pro Gly Gln Ala Pro Arg Leu Leu Ile
            35                  40                  45

Lys Tyr Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 62
<211> LENGTH: 693
<212> TYPE: PRT
<213> ORGANISM: artificial
<220> FEATURE:
<223> OTHER INFORMATION: variant antibody sequence

<400> SEQUENCE: 62

Gln Val Gln Leu Val Gln Ser Gly Ala Glu Val Lys Lys Pro Gly Ala
```

-continued

```
1               5                   10                  15
Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Lys Asp Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Ile Thr Thr Thr Pro Phe Asp Phe Trp Gly Gln Gly Thr
                100                 105                 110

Thr Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Gly Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gln Leu Pro Ser Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430
```

His Asn His Tyr Thr Gln Lys Ser Leu Ser Leu Ser Pro Gly Lys Ser
            435                 440                 445

Gly Glu Val Gln Leu Val Glu Ser Gly Gly Gly Leu Val Gln Pro Gly
    450                 455                 460

Gly Ser Leu Arg Leu Ser Cys Ala Ala Ser Gly Tyr Ser Phe Thr Gly
465                 470                 475                 480

Tyr Thr Met Asn Trp Val Arg Gln Ala Pro Gly Lys Gly Leu Glu Trp
                485                 490                 495

Val Ala Leu Ile Asn Pro Tyr Lys Gly Val Ser Thr Tyr Asn Gln Lys
            500                 505                 510

Phe Lys Asp Arg Phe Thr Ile Ser Val Asp Lys Ser Lys Asn Thr Ala
            515                 520                 525

Tyr Leu Gln Met Asn Ser Leu Arg Ala Glu Asp Thr Ala Val Tyr Tyr
            530                 535                 540

Cys Ala Arg Ser Gly Tyr Tyr Gly Asp Ser Asp Trp Tyr Phe Asp Val
545                 550                 555                 560

Trp Gly Gln Gly Thr Leu Val Thr Val Ser Ser Gly Gly Gly Gly Ser
                565                 570                 575

Gly Gly Gly Gly Ser Gly Gly Gly Ser Asp Ile Gln Met Thr Gln
            580                 585                 590

Ser Pro Ser Ser Leu Ser Ala Ser Val Gly Asp Arg Val Thr Ile Thr
            595                 600                 605

Cys Arg Ala Ser Gln Asp Ile Arg Asn Tyr Leu Asn Trp Tyr Gln Gln
    610                 615                 620

Lys Pro Gly Lys Ala Pro Lys Leu Leu Ile Tyr Tyr Thr Ser Arg Leu
625                 630                 635                 640

Glu Ser Gly Val Pro Ser Arg Phe Ser Gly Ser Gly Ser Gly Thr Asp
                645                 650                 655

Tyr Thr Leu Thr Ile Ser Ser Leu Gln Pro Glu Asp Phe Ala Thr Tyr
            660                 665                 670

Tyr Cys Gln Gln Gly Asn Thr Leu Pro Trp Thr Phe Gly Gln Gly Thr
            675                 680                 685

Lys Val Glu Ile Lys
    690

<210> SEQ ID NO 63
<211> LENGTH: 214
<212> TYPE: PRT
<213> ORGANISM: artificial
<220> FEATURE:
<223> OTHER INFORMATION: variant antibody sequence

<400> SEQUENCE: 63

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Ala Ser Gln Ser Ala Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

```
Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 64
<211> LENGTH: 693
<212> TYPE: PRT
<213> ORGANISM: artificial
<220> FEATURE:
<223> OTHER INFORMATION: variant antibody sequence

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
            35                  40                  45

Gly Glu Ile Asp Pro Ser Asp Ser Tyr Lys Asp Tyr Asn Gln Lys Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Ile Thr Thr Thr Pro Phe Asp Phe Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                    165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Pro Val Ala Gly Pro Ser Val
225                 230                 235                 240
```

-continued

```
Phe Leu Phe Pro Pro Lys Pro Lys Asp Thr Leu Met Ile Ser Arg Thr
            245                 250                 255

Pro Glu Val Thr Cys Val Val Val Gly Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gln Leu Pro Ser Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Ser
            435                 440                 445

Gly Glu Val Gln Leu Val Glu Ser Gly Gly Gly Leu Val Gln Pro Gly
450                 455                 460

Gly Ser Leu Arg Leu Ser Cys Ala Ala Ser Gly Tyr Ser Phe Thr Gly
465                 470                 475                 480

Tyr Thr Met Asn Trp Val Arg Gln Ala Pro Gly Lys Gly Leu Glu Trp
                485                 490                 495

Val Ala Leu Ile Asn Pro Tyr Lys Gly Val Ser Thr Tyr Asn Gln Lys
            500                 505                 510

Phe Lys Asp Arg Phe Thr Ile Ser Val Asp Lys Ser Lys Asn Thr Ala
            515                 520                 525

Tyr Leu Gln Met Asn Ser Leu Arg Ala Glu Asp Thr Ala Val Tyr Tyr
            530                 535                 540

Cys Ala Arg Ser Gly Tyr Tyr Gly Asp Ser Asp Trp Tyr Phe Asp Val
545                 550                 555                 560

Trp Gly Gln Gly Thr Leu Val Thr Val Ser Ser Gly Gly Gly Gly Ser
                565                 570                 575

Gly Gly Gly Gly Ser Gly Gly Gly Ser Asp Ile Gln Met Thr Gln
            580                 585                 590

Ser Pro Ser Ser Leu Ser Ala Ser Val Gly Asp Arg Val Thr Ile Thr
            595                 600                 605

Cys Arg Ala Ser Gln Asp Ile Arg Asn Tyr Leu Asn Trp Tyr Gln Gln
610                 615                 620

Lys Pro Gly Lys Ala Pro Lys Leu Leu Ile Tyr Tyr Thr Ser Arg Leu
625                 630                 635                 640

Glu Ser Gly Val Pro Ser Arg Phe Ser Gly Ser Gly Ser Gly Thr Asp
                645                 650                 655
```

```
Tyr Thr Leu Thr Ile Ser Ser Leu Gln Pro Glu Asp Phe Ala Thr Tyr
            660                 665                 670

Tyr Cys Gln Gln Gly Asn Thr Leu Pro Trp Thr Phe Gly Gln Gly Thr
            675                 680                 685

Lys Val Glu Ile Lys
        690

<210> SEQ ID NO 65
<211> LENGTH: 214
<212> TYPE: PRT
<213> ORGANISM: artificial
<220> FEATURE:
<223> OTHER INFORMATION: variant antibody sequence

<400> SEQUENCE: 65

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 66
<211> LENGTH: 693
<212> TYPE: PRT
<213> ORGANISM: artificial
<220> FEATURE:
<223> OTHER INFORMATION: variant antibody sequence

<400> SEQUENCE: 66

Gln Val Gln Leu Val Gln Ser Gly Ala Glu Val Lys Lys Pro Gly Gly
1               5                   10                  15

Ser Leu Arg Leu Ser Cys Ala Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45
```

```
Gly Glu Ile Asp Pro Ser Asp Ser Tyr Lys Asp Tyr Asn Gln Lys Phe
    50                  55                  60

Lys Asp Arg Val Thr Ile Ser Arg Asp Thr Ser Lys Asn Thr Leu Tyr
65                  70                  75                  80

Leu Gln Leu Ser Ser Leu Arg Ala Glu Asp Thr Ala Val Tyr Tyr Cys
                85                  90                  95

Ala Arg Ala Ile Thr Thr Thr Pro Phe Asp Phe Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Gly Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gln Leu Pro Ser Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Ser
        435                 440                 445

Gly Glu Val Gln Leu Val Glu Ser Gly Gly Leu Val Gln Pro Gly
    450                 455                 460
```

```
Gly Ser Leu Arg Leu Ser Cys Ala Ala Ser Gly Tyr Ser Phe Thr Gly
465                 470                 475                 480

Tyr Thr Met Asn Trp Val Arg Gln Ala Pro Gly Lys Gly Leu Glu Trp
                485                 490                 495

Val Ala Leu Ile Asn Pro Tyr Lys Gly Val Ser Thr Tyr Asn Gln Lys
            500                 505                 510

Phe Lys Asp Arg Phe Thr Ile Ser Val Asp Lys Ser Lys Asn Thr Ala
        515                 520                 525

Tyr Leu Gln Met Asn Ser Leu Arg Ala Glu Asp Thr Ala Val Tyr Tyr
    530                 535                 540

Cys Ala Arg Ser Gly Tyr Tyr Gly Asp Ser Asp Trp Tyr Phe Asp Val
545                 550                 555                 560

Trp Gly Gln Gly Thr Leu Val Thr Val Ser Ser Gly Gly Gly Gly Ser
                565                 570                 575

Gly Gly Gly Gly Ser Gly Gly Gly Ser Asp Ile Gln Met Thr Gln
                580                 585                 590

Ser Pro Ser Ser Leu Ser Ala Ser Val Gly Asp Arg Val Thr Ile Thr
            595                 600                 605

Cys Arg Ala Ser Gln Asp Ile Arg Asn Tyr Leu Asn Trp Tyr Gln Gln
610                 615                 620

Lys Pro Gly Lys Ala Pro Lys Leu Leu Ile Tyr Tyr Thr Ser Arg Leu
625                 630                 635                 640

Glu Ser Gly Val Pro Ser Arg Phe Ser Gly Ser Gly Ser Gly Thr Asp
                645                 650                 655

Tyr Thr Leu Thr Ile Ser Ser Leu Gln Pro Glu Asp Phe Ala Thr Tyr
        660                 665                 670

Tyr Cys Gln Gln Gly Asn Thr Leu Pro Trp Thr Phe Gly Gln Gly Thr
            675                 680                 685

Lys Val Glu Ile Lys
            690

<210> SEQ ID NO 67
<211> LENGTH: 214
<212> TYPE: PRT
<213> ORGANISM: artificial
<220> FEATURE:
<223> OTHER INFORMATION: variant antibody sequence

<400> SEQUENCE: 67

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
    210
```

<210> SEQ ID NO 68
<211> LENGTH: 693
<212> TYPE: PRT
<213> ORGANISM: artificial
<220> FEATURE:
<223> OTHER INFORMATION: variant antibody sequence

<400> SEQUENCE: 68

```
Gln Val Gln Leu Gln Gln Pro Gly Ala Glu Leu Val Lys Pro Gly Ala
1               5                   10                  15

Ser Leu Lys Leu Ser Cys Lys Ser Ser Gly Tyr Thr Phe Thr Ser Tyr
            20                  25                  30

Trp Met His Trp Val Arg Gln Arg Pro Gly His Gly Leu Glu Trp Ile
        35                  40                  45

Gly Glu Ile Asp Pro Ser Asp Ser Tyr Lys Asp Tyr Asn Gln Lys Phe
50                  55                  60

Lys Asp Lys Ala Thr Leu Thr Val Asp Arg Ser Ser Asn Thr Ala Tyr
65                  70                  75                  80

Met His Leu Ser Ser Leu Thr Ser Asp Ser Ala Val Tyr Tyr Cys
                85                  90                  95

Ala Arg Ala Ile Thr Thr Thr Pro Phe Asp Phe Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Gly Val Ser His Glu Asp Pro Glu
            260                 265                 270
```

```
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Gln Leu Pro Ser Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys Ser
            435                 440                 445
Gly Asp Ile Gln Met Thr Gln Ser Pro Ser Ser Leu Ser Ala Ser Val
            450                 455                 460
Gly Asp Arg Val Thr Ile Thr Cys Arg Ala Ser Gln Asp Ile Arg Asn
465                 470                 475                 480
Tyr Leu Asn Trp Tyr Gln Gln Lys Pro Gly Lys Ala Pro Lys Leu Leu
                485                 490                 495
Ile Tyr Tyr Thr Ser Arg Leu Glu Ser Gly Val Pro Ser Arg Phe Ser
            500                 505                 510
Gly Ser Gly Ser Gly Thr Asp Tyr Thr Leu Thr Ile Ser Ser Leu Gln
            515                 520                 525
Pro Glu Asp Phe Ala Thr Tyr Tyr Cys Gln Gln Gly Asn Thr Leu Pro
530                 535                 540
Trp Thr Phe Gly Gln Gly Thr Lys Val Glu Ile Lys Gly Gly Gly Gly
545                 550                 555                 560
Ser Gly Gly Gly Gly Ser Gly Gly Gly Ser Glu Val Gln Leu Val
                565                 570                 575
Glu Ser Gly Gly Gly Leu Val Gln Pro Gly Gly Ser Leu Arg Leu Ser
            580                 585                 590
Cys Ala Ala Ser Gly Tyr Ser Phe Thr Gly Tyr Thr Met Asn Trp Val
            595                 600                 605
Arg Gln Ala Pro Gly Lys Gly Leu Glu Trp Val Ala Leu Ile Asn Pro
610                 615                 620
Tyr Lys Gly Val Ser Thr Tyr Asn Gln Lys Phe Lys Asp Arg Phe Thr
625                 630                 635                 640
Ile Ser Val Asp Lys Ser Lys Asn Thr Ala Tyr Leu Gln Met Asn Ser
                645                 650                 655
Leu Arg Ala Glu Asp Thr Ala Val Tyr Tyr Cys Ala Arg Ser Gly Tyr
            660                 665                 670
Tyr Gly Asp Ser Asp Trp Tyr Phe Asp Val Trp Gly Gln Gly Thr Leu
            675                 680                 685
Val Thr Val Ser Ser
```

-continued

```
                690

<210> SEQ ID NO 69
<211> LENGTH: 214
<212> TYPE: PRT
<213> ORGANISM: artificial
<220> FEATURE:
<223> OTHER INFORMATION: variant antibody sequence

<400> SEQUENCE: 69

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 70
<211> LENGTH: 693
<212> TYPE: PRT
<213> ORGANISM: artificial
<220> FEATURE:
<223> OTHER INFORMATION: variant antibody sequence

<400> SEQUENCE: 70

Gln Val Gln Leu Gln Gln Pro Gly Ala Glu Leu Val Lys Pro Gly Ala
1               5                   10                  15

Ser Leu Lys Leu Ser Cys Lys Ser Gly Tyr Thr Phe Thr Ser Tyr
            20                  25                  30

Trp Met His Trp Val Arg Gln Arg Pro Gly His Gly Leu Glu Trp Ile
        35                  40                  45

Gly Glu Ile Asp Pro Ser Asp Ser Tyr Lys Asp Tyr Asn Gln Lys Phe
    50                  55                  60

Lys Asp Lys Ala Thr Leu Thr Val Asp Arg Ser Ser Asn Thr Ala Tyr
65                  70                  75                  80
```

```
Met His Leu Ser Ser Leu Thr Ser Asp Asp Ser Ala Val Tyr Tyr Cys
             85                  90                  95

Ala Arg Ala Ile Thr Thr Thr Pro Phe Asp Phe Trp Gly Gln Gly Thr
        100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Gly Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gln Leu Pro Ser Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Ser
        435                 440                 445

Gly Asp Ile Gln Met Thr Gln Ser Pro Ser Ser Leu Ser Ala Ser Val
    450                 455                 460

Gly Asp Arg Val Thr Ile Thr Cys Arg Ala Ser Gln Asp Ile Arg Asn
465                 470                 475                 480

Tyr Leu Asn Trp Tyr Gln Gln Lys Pro Gly Lys Ala Pro Lys Leu Leu
                485                 490                 495

Ile Tyr Tyr Thr Ser Arg Leu Glu Ser Gly Val Pro Ser Arg Phe Ser
```

```
                500             505             510
Gly Ser Gly Ser Gly Thr Asp Tyr Thr Leu Thr Ile Ser Ser Leu Gln
            515                 520                 525

Pro Glu Asp Phe Ala Thr Tyr Tyr Cys Gln Gln Gly Asn Thr Leu Pro
        530                 535                 540

Trp Thr Phe Gly Gln Gly Thr Lys Val Glu Ile Lys Gly Gly Gly Gly
545                 550                 555                 560

Ser Gly Gly Gly Ser Gly Gly Gly Ser Glu Val Gln Leu Val
                565                 570                 575

Glu Ser Gly Gly Gly Leu Val Gln Pro Gly Gly Ser Leu Arg Leu Ser
                580                 585                 590

Cys Ala Ala Ser Gly Tyr Ser Phe Thr Gly Tyr Thr Met Asn Trp Val
            595                 600                 605

Arg Gln Ala Pro Gly Lys Gly Leu Glu Trp Val Ala Leu Ile Asn Pro
        610                 615                 620

Tyr Lys Gly Val Ser Thr Tyr Ala Asp Ser Phe Lys Gly Arg Phe Thr
625                 630                 635                 640

Ile Ser Val Asp Asp Ser Lys Asn Thr Ala Tyr Leu Gln Met Asn Ser
                645                 650                 655

Leu Arg Ala Glu Asp Thr Ala Val Tyr Tyr Cys Ala Arg Ser Gly Tyr
            660                 665                 670

Tyr Gly Asp Ser Asp Trp Tyr Phe Asp Val Trp Gly Gln Gly Thr Leu
        675                 680                 685

Val Thr Val Ser Ser
        690

<210> SEQ ID NO 71
<211> LENGTH: 214
<212> TYPE: PRT
<213> ORGANISM: artificial
<220> FEATURE:
<223> OTHER INFORMATION: variant antibody sequence

<400> SEQUENCE: 71

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 72
<211> LENGTH: 693
<212> TYPE: PRT
<213> ORGANISM: artificial
<220> FEATURE:
<223> OTHER INFORMATION: variant antibody sequence

<400> SEQUENCE: 72

Gln Val Gln Leu Gln Gln Pro Gly Ala Glu Leu Val Lys Pro Gly Ala
1               5                   10                  15

Ser Leu Lys Leu Ser Cys Lys Ser Ser Gly Tyr Thr Phe Thr Ser Tyr
            20                  25                  30

Trp Met His Trp Val Arg Gln Arg Pro Gly His Gly Leu Glu Trp Ile
        35                  40                  45

Gly Glu Ile Asp Pro Ser Asp Ser Tyr Lys Asp Tyr Asn Gln Lys Phe
    50                  55                  60

Lys Asp Lys Ala Thr Leu Thr Val Asp Arg Ser Ser Asn Thr Ala Tyr
65                  70                  75                  80

Met His Leu Ser Ser Leu Thr Ser Asp Asp Ser Ala Val Tyr Tyr Cys
                85                  90                  95

Ala Arg Ala Ile Thr Thr Thr Pro Phe Asp Phe Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Gly Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys

```
            305                 310                 315                 320
Cys Lys Val Ser Asn Lys Gln Leu Pro Ser Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys Ser
                435                 440                 445

Gly Asp Ile Gln Met Thr Gln Ser Pro Ser Ser Leu Ser Ala Ser Val
                450                 455                 460

Gly Asp Arg Val Thr Ile Thr Cys Arg Ala Ser Gln Asp Ile Arg Asn
465                 470                 475                 480

Tyr Leu Asn Trp Tyr Gln Gln Lys Pro Gly Lys Ala Pro Lys Leu Leu
                485                 490                 495

Ile Tyr Tyr Thr Ser Arg Leu Glu Ser Gly Val Pro Ser Arg Phe Ser
                500                 505                 510

Gly Ser Gly Ser Gly Thr Asp Tyr Thr Leu Thr Ile Ser Ser Leu Gln
                515                 520                 525

Pro Glu Asp Phe Ala Thr Tyr Tyr Cys Gln Gln Gly Asn Thr Leu Pro
                530                 535                 540

Trp Thr Phe Gly Gln Gly Thr Lys Val Glu Ile Lys Gly Gly Gly Gly
545                 550                 555                 560

Ser Gly Gly Gly Gly Ser Gly Gly Gly Gly Ser Glu Val Gln Leu Val
                565                 570                 575

Glu Ser Gly Gly Gly Leu Val Gln Pro Gly Gly Ser Leu Arg Leu Ser
                580                 585                 590

Cys Ala Ala Ser Gly Tyr Ser Phe Thr Gly Tyr Thr Met Asn Trp Val
                595                 600                 605

Arg Gln Ala Pro Gly Lys Gly Leu Glu Trp Val Ala Leu Ile Asn Pro
                610                 615                 620

Tyr Lys Gly Val Ser Thr Tyr Asn Gln Lys Phe Lys Asp Arg Phe Thr
625                 630                 635                 640

Ile Ser Val Asp Asp Ser Lys Asn Thr Ala Tyr Leu Gln Met Asn Ser
                645                 650                 655

Leu Arg Ala Glu Asp Thr Ala Val Tyr Tyr Cys Ala Arg Ser Gly Tyr
                660                 665                 670

Tyr Gly Asp Ser Asp Trp Tyr Phe Asp Val Trp Gly Gln Gly Thr Leu
                675                 680                 685

Val Thr Val Ser Ser
                690

<210> SEQ ID NO 73
<211> LENGTH: 214
<212> TYPE: PRT
<213> ORGANISM: artificial
```

<220> FEATURE:
<223> OTHER INFORMATION: variant antibody sequence

<400> SEQUENCE: 73

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Thr Asp Phe Thr Leu Ser Ile Asn Ser Val Glu Thr
65                  70                  75                  80

Glu Asp Phe Gly Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 74
<211> LENGTH: 693
<212> TYPE: PRT
<213> ORGANISM: artificial
<220> FEATURE:
<223> OTHER INFORMATION: variant antibody sequence

<400> SEQUENCE: 74

Gln Val Gln Leu Gln Gln Pro Gly Ala Glu Leu Val Lys Pro Gly Ala
1               5                   10                  15

Ser Leu Lys Leu Ser Cys Lys Ser Ser Gly Tyr Thr Phe Thr Ser Tyr
                20                  25                  30

Trp Met His Trp Val Arg Gln Arg Pro Gly His Gly Leu Glu Trp Ile
            35                  40                  45

Gly Glu Ile Asp Pro Ser Asp Ser Tyr Lys Asp Tyr Asn Gln Lys Phe
        50                  55                  60

Lys Asp Lys Ala Thr Leu Thr Val Asp Arg Ser Ser Asn Thr Ala Tyr
65                  70                  75                  80

Met His Leu Ser Ser Leu Thr Ser Asp Asp Ser Ala Val Tyr Tyr Cys
                85                  90                  95

Ala Arg Ala Ile Thr Thr Thr Pro Phe Asp Phe Trp Gly Gln Gly Thr
            100                 105                 110

Thr Leu Thr Val Ser Ser Ala Ser Thr Lys Gly Pro Ser Val Phe Pro

```
              115                 120                 125
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Gly Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gln Leu Pro Ser Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Ser
        435                 440                 445

Gly Glu Val Gln Leu Val Glu Ser Gly Gly Gly Leu Val Gln Pro Gly
    450                 455                 460

Gly Ser Leu Arg Leu Ser Cys Ala Ala Ser Gly Tyr Ser Phe Thr Gly
465                 470                 475                 480

Tyr Thr Met Asn Trp Val Arg Gln Ala Pro Gly Lys Gly Leu Glu Trp
                485                 490                 495

Val Ala Leu Ile Asn Pro Tyr Lys Gly Val Ser Thr Tyr Asn Gln Lys
            500                 505                 510

Phe Lys Asp Arg Phe Thr Ile Ser Val Asp Lys Ser Lys Asn Thr Ala
        515                 520                 525

Tyr Leu Gln Met Asn Ser Leu Arg Ala Glu Asp Thr Ala Val Tyr Tyr
    530                 535                 540
```

```
Cys Ala Arg Ser Gly Tyr Tyr Gly Asp Ser Asp Trp Tyr Phe Asp Val
545                 550                 555                 560

Trp Gly Gln Gly Thr Leu Val Thr Val Ser Ser Gly Gly Gly Gly Ser
            565                 570                 575

Gly Gly Gly Gly Ser Gly Gly Gly Ser Asp Ile Gln Met Thr Gln
        580                 585                 590

Ser Pro Ser Ser Leu Ser Ala Ser Val Gly Asp Arg Val Thr Ile Thr
        595                 600                 605

Cys Arg Ala Ser Gln Asp Ile Arg Asn Tyr Leu Asn Trp Tyr Gln Gln
    610                 615                 620

Lys Pro Gly Lys Ala Pro Lys Leu Leu Ile Tyr Tyr Thr Ser Arg Leu
625                 630                 635                 640

Glu Ser Gly Val Pro Ser Arg Phe Ser Gly Ser Gly Ser Gly Thr Asp
                645                 650                 655

Tyr Thr Leu Thr Ile Ser Ser Leu Gln Pro Glu Asp Phe Ala Thr Tyr
            660                 665                 670

Tyr Cys Gln Gln Gly Asn Thr Leu Pro Trp Thr Phe Gly Gln Gly Thr
        675                 680                 685

Lys Val Glu Ile Lys
    690
```

<210> SEQ ID NO 75
<211> LENGTH: 214
<212> TYPE: PRT
<213> ORGANISM: artificial
<220> FEATURE:
<223> OTHER INFORMATION: variant antibody sequence

<400> SEQUENCE: 75

```
Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Thr Asp Phe Thr Leu Ser Ile Asn Ser Val Glu Thr
65                  70                  75                  80

Glu Asp Phe Gly Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210

<210> SEQ ID NO 76
<211> LENGTH: 118
<212> TYPE: PRT
<213> ORGANISM: artificial
<220> FEATURE:
<223> OTHER INFORMATION: variant antibody sequence

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Glu Ile Asp Pro Ser Asp Ser Tyr Lys Asp Tyr Asn Gln Lys Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Ile Thr Thr Thr Pro Phe Asp Phe Trp Gly Gln Gly Thr
            100                 105                 110

Thr Val Thr Val Ser Ser
        115

<210> SEQ ID NO 77
<211> LENGTH: 107
<212> TYPE: PRT
<213> ORGANISM: artificial
<220> FEATURE:
<223> OTHER INFORMATION: variant antibody sequence

<400> SEQUENCE: 77

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
                20                  25                  30

Leu His Trp Tyr Gln Gln Lys Pro Gly Gln Ala Pro Arg Leu Leu Ile
            35                  40                  45

Tyr Tyr Ala Ser Gln Ser Ile Ser Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Thr Trp Pro Tyr
                85                  90                  95

Thr Phe Gly Gly Gly Thr Lys Leu Glu Ile Lys
            100                 105

<210> SEQ ID NO 78
<211> LENGTH: 693
<212> TYPE: PRT
<213> ORGANISM: artificial
<220> FEATURE:
<223> OTHER INFORMATION: variant antibody sequence

<400> SEQUENCE: 78
```

-continued

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
            35                  40                  45

Gly Glu Ile Asp Pro Ser Asp Ser Tyr Lys Asp Tyr Asn Gln Lys Phe
     50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Ala Ile Thr Thr Thr Pro Phe Asp Phe Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
     130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Gly Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gln Leu Pro Ser Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
```

-continued

```
                420                 425                 430
His Asn His Tyr Thr Gln Lys Ser Leu Ser Leu Ser Pro Gly Lys Ser
            435                 440                 445

Gly Asp Ile Gln Met Thr Gln Ser Pro Ser Ser Leu Ser Ala Ser Val
    450                 455                 460

Gly Asp Arg Val Thr Ile Thr Cys Arg Ala Ser Gln Asp Ile Arg Asn
465                 470                 475                 480

Tyr Leu Asn Trp Tyr Gln Gln Lys Pro Gly Lys Ala Pro Lys Leu Leu
                485                 490                 495

Ile Tyr Tyr Thr Ser Arg Leu Glu Ser Gly Val Pro Ser Arg Phe Ser
            500                 505                 510

Gly Ser Gly Ser Gly Thr Asp Tyr Thr Leu Thr Ile Ser Ser Leu Gln
        515                 520                 525

Pro Glu Asp Phe Ala Thr Tyr Tyr Cys Gln Gln Gly Asn Thr Leu Pro
    530                 535                 540

Trp Thr Phe Gly Gln Gly Thr Lys Val Glu Ile Lys Gly Gly Gly Gly
545                 550                 555                 560

Ser Gly Gly Gly Gly Ser Gly Gly Gly Gly Ser Glu Val Gln Leu Val
                565                 570                 575

Glu Ser Gly Gly Gly Leu Val Gln Pro Gly Gly Ser Leu Arg Leu Ser
            580                 585                 590

Cys Ala Ala Ser Gly Tyr Ser Phe Thr Gly Tyr Thr Met Asn Trp Val
            595                 600                 605

Arg Gln Ala Pro Gly Lys Gly Leu Glu Trp Val Ala Leu Ile Asn Pro
    610                 615                 620

Tyr Lys Gly Val Ser Thr Tyr Asn Gln Lys Phe Lys Asp Arg Phe Thr
625                 630                 635                 640

Ile Ser Val Asp Lys Ser Lys Asn Thr Ala Tyr Leu Gln Met Asn Ser
                645                 650                 655

Leu Arg Ala Glu Asp Thr Ala Val Tyr Tyr Cys Ala Arg Ser Gly Tyr
            660                 665                 670

Tyr Gly Asp Ser Asp Trp Tyr Phe Asp Val Trp Gly Gln Gly Thr Leu
        675                 680                 685

Val Thr Val Ser Ser
    690

<210> SEQ ID NO 79
<211> LENGTH: 214
<212> TYPE: PRT
<213> ORGANISM: artificial
<220> FEATURE:
<223> OTHER INFORMATION: variant antibody sequence

<400> SEQUENCE: 79

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Thr Trp Pro Tyr
```

-continued

```
                85                   90                   95
Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

ANTI-FLT₃ ANTIGEN BINDING PROTEINS

CROSS-REFERENCE TO RELATED APPLICATIONS

This application is a U.S. National Phase Application of International Application No. PCT/EP2019/074268 filed Sep. 11, 2019, which claims foreign priority to Application No. EP19189566.3 filed Aug. 1, 2019 and Application No. EP18193889.5 filed Sep. 11, 2018, which are incorporated herein by reference in their entirety.

FIELD OF THE INVENTION

The present invention provides novel human fms related tyrosine kinase 3 (FLT3) antigen binding proteins, such as antibodies, having improved FLT3 binding affinity, and/or anti-tumor activity. The FLT3 antibodies of the invention were generated by mutation of a parent FLT3 antibody and tested in in vitro in binding assays as well as in vivo in a mouse tumor model and in human patient tumor samples. The antibodies of the invention are provided as monospecific constructs or in a bispecific FLT3×CD3 antibody format and show excellent target affinity and/or tumor cell killing. The present invention also relates methods for producing the antigen binding proteins of the invention as well as nucleic acids encoding them, vectors for and host cells for their expression. The invention further relates to methods of treating or diagnosing a disease such as leukemia using an FLT3 antigen binding protein (ABP) of the invention.

DESCRIPTION

Scientific work starting in the 1980ies has established that bispecific antibodies directed to a tumor associated antigen (TAA) and the T cell receptor (TCR)/CD3-complex are capable of activating T cells resulting in the lysis of TAA expressing tumor cells by the activated T cells (Staerz et al. Nature 1985, 314:628-631; Perez et al. Nature 1985, 316: 354-356; Jung et al. Proc Natl Acad Sci USA 1986, 83:4479-4483). Since CD3-antibodies, bound to Fc receptors (FcRs) via their Fc-part, are exceedingly efficient in inducing T cell activation and cytokine release as unwanted side effects, it is of paramount importance to construct Fc-depleted or -attenuated bispecific TAA×CD3-antibodies in order to prevent FcR binding and to allow for a target cell restricted—rather than FcR-mediated activation of T cells (Jung et al. Immunol Today 1988; 9:257-260; Jung et al. Eur J Immunol 1991; 21:2431-2435).

The production of bispecific antibodies meeting this critical prerequisite in industrial quality and quantity remains a formidable challenge. Recently, a recombinant, bispecific single chain (bssc) antibody with CD19×CD3-specificity, termed Blinatumomab, has demonstrated considerable efficiency in the treatment of patients with ALL (Bargou et al. Science 2008, 321:974-977) and has received approval under a break through designation by the FDA. Notably, the drug is applied as continuous 24 hr infusion over several weeks due to its low serum half-life and rather high toxicity: safely applicable doses are approx. 30 µg per patient and day which is 10.000 times lower than those used for treatment with established monospecific antitumor antibodies (Adams and Weiner. Nat Biotechnol 2005, 23:1147-57). The resulting serum concentrations of the drug are below 1 ng/ml (Topp et al. J Clin Oncol 2011; 29:2493-2498). This severe dose limitation, also observed in earlier clinical trials with different bispecific antibodies (Kroesen et al. Br J Cancer 1994; 70:652-661; Tibben et al. Int J Cancer 1996; 66:477-483), is due to off-target T cell activation resulting in systemic cytokine release. Obviously, this phenomenon prevents an optimal therapeutic activity of bispecific antibodies stimulating the TCR/CD3 complex.

In principle, dose limiting off-target T cell activation and the resulting toxicity problem may be caused by two different mechanisms. T cell activation is not—as it should be—target cell restricted, that is, even a monovalent CD3 effector binding site within a bispecific antibody construct is capable of inducing some T cell activation in the absence of target cells to which the antibody binds with its targeting moiety. This represents off-target activation in a strict sense, since cells carrying a target antigen are not required to induce the phenomenon. We have noticed that this phenomenon varies considerably if different CD3 antibodies in different formats are used and if certain stimulating bystander cells (SBCs), such as lymphoma cells (SKW6.4) or endothelial cells (HUVECs) are added that provide co-stimuli for T cell activation. Thus, one should select a CD3 moiety inducing minimal "off-target" T cell activation for the construction of bispecific antibodies.

The TAA targeted by the bispecific antibody is not entirely tumor specific resulting in antibody mediated T cell activation due to binding to normal, TAA expressing cells. In a strict sense this is no off target activation, since it is induced by antigen expressing target cells albeit the "wrong ones", that is, normal rather than malignant cells. Blinatumomab, the bispecific CD19×CD3-antibody mentioned above, certainly faces this problem since its target antigen CD19 is expressed on normal B lymphocytes. Obviously, the specificity of the targeting antigen for malignant tissue is critical to prevent off-target T cell activation of this kind. Fms-like tyrosine kinase 3 (FLT3) is a hematopoietic Class III receptor tyrosine kinase protein that shares homology with other Class III family members including stem cell factor receptor (c-KIT), macrophage colony-stimulating factor receptor (FMS) and platelet-derived growth factor receptor (PDGFR). Upon binding with the FLT3 ligand, FLT3 receptor undergoes homodimerization thereby enabling autophosphorylation of specific tyrosine residues in the juxtamembrane domain and downstream activation via PI3K Akt, MAPK and STAT5 pathways. FLT3 thus plays a crucial role as a signaling component in controlling proliferation, survival and differentiation of normal hematopoietic cells.

Human FLT3 is expressed in CD34+CD38− hematopoietic stem cells (HSC) as well as in a subset of dendritic precursor cells. FLT3 expression can also be detected in multipotent progenitor cells like the CD34+CD38+CD45RA−CD123$^{low}$ Common Myeloid Progenitor (CMP), the CD34+CD38+CD45RA+CD123$^{low}$ Granulocyte Monocyte Progenitors (GMP), and CD34+CD38+CD10+CD19− Common Lymphoid Progenitor cells (CLP). Interestingly, FLT3 expression is almost absent in the CD34+CD38−CD45RA−CD123− Megakaryocyte Erythrocyte Progenitor cells (MEP). FLT3 expression is thus confined mainly to the early myeloid and lymphoid progenitor cells with some expression in the more mature monocytic lineage cells. In acute myeloid leukemia (AML) and acute lymphocytic leukemia (ALL), FLT3 is expressed at very high levels. FLT3 is also expressed in chronic myeloid leukemia (CML) in blast crisis but not in chronic phase. Overall, FLT3 is expressed in approximately 98% of pre-B ALL patients and in about 90% of AML patients.

Between 15% and 34% of AML patients show FLT3/ITD mutations, with the lower frequency in children and higher frequency in older adults. Both adult and pediatric AML patients with FLT3/ITD mutations have very poor prognosis (Rombouts W J, Blokland I, Löwenberg B, Ploemacher RELeukemia. 2000 April; 14(4):675-83.), and therefore FLT3 is a promising target for AML but also ALL therapy. Mutated FLT3 is constitutively activated, and FLT3 signals through pathways that include ras/MAP kinase, STAT5, and PI3 kinase/AKT, contributing to blocks in apoptosis and differentiation and stimulating proliferation. FLT3 can be targeted via an antibody approach for therapy of both AML and ALL. Antibodies that bind to FLT3 and inhibit FL binding to the receptor have been developed. The Imclone antibody, IMC-EB10 was evaluated in relapsed AML patients in a Phase I study, however, the study was terminated due to lack of efficacy (ClinicalTrials.gov Identifier: NCT00887926). There thus remains a pressing need to evaluate second generation monoclonal antibodies including bispecific antibodies for treatment of AML.

In addition to T cell activation induced by genuinely monomeric CD3 stimulation, a recent paper suggests an alternative mechanism for off-target activation involving the targeting part of a bispecific antibody; if this part consists of a single chain fragment that induces clustering of the effector part of the bispecific antibody on the T cell surface, tonic signaling may be induced resulting in T cell exhaustion (Long et al. Nat Med 2015; 6:581), that is barely detectable by conventional, short term in vitro assays but severely affects in vivo efficiency. These observations have been made using T cells transfected with a chimeric antigen receptor (CAR T cells). Chimeric T cell receptors comprise single chain antibodies as targeting moieties. It is highly likely that the results of Long et al. (2015) likewise apply to bispecific antibodies with such a targeting part, since these reagents, once bound to a T cell, are functionally equivalent to a T cell transfected with the corresponding CAR. It is well known in the field that most single chain antibodies have the tendency to form multimers and aggregates (Worn et al. J Mol Biol 2001, 305:989-1010), and thus it is not surprising that all but one of the CARs tested by Long et al. (2015) showed the phenomenon of clustering and tonic CD3 signaling albeit to a variable degree (Long et al. 2015). The problem outlined here calls for a bispecific format that prevents multimerization of—and clustering by the targeting part.

Most bispecific formats suffer from a very low serum half-life (1-3 hrs) due to reduced molecular weight and lack of CH3 domains. Thus, the prototypical Blinatumomab antibody is applied by continuous 24 hr i.v. infusion over several weeks. The use of whole IgG-based formats with increased serum half-life, such as the IgGsc depicted in FIG. 1, has been considered unsuitable because the possibly increased off-target activation induced by the bivalent C-terminal CD3 binding moiety.

Based on the above, there is a need in the art for improved ABPs targeting FLT3 that address at least one of the problems outlined above.

BRIEF DESCRIPTION OF THE INVENTION

Generally, and by way of brief description, the main aspects of the present invention can be described as follows:

In a first aspect, the invention pertains to an An Antigen Binding Protein (ABP) capable of binding to human fms related tyrosine kinase 3 (FLT3), comprising:

(i) one, preferably two, heavy chain variable domain(s) comprising the CDRH1 region set forth in SEQ ID NO: 01 (SYWMH), the CDRH2 region set forth in SEQ ID NO: 02 (EIDPSDSYKDYNQKFKD), and the CDRH3 region set forth in SEQ ID NO: 03 (AITTTPFDF), or wherein in each case independently the CDRH1, CDRH2 and/or CDRH3 comprise a sequence having no more than three or two, preferably no more than one amino acid substitution(s), deletion(s) or insertion(s) compared to SEQ ID NO: 01, SEQ ID NO: 02, or SEQ ID NO: 03, respectively; and (ii) one, preferably two, light chain variable domain(s) comprising the CDRL1 region set forth in SEQ ID NO: 05 (RASQSISNNLH), the CDRL2 region set forth in SEQ ID NO: 06 (YASQSIS), and the CDRL3 region set forth in SEQ ID NO: 07 (QQSNTWPYT) or wherein in each case independently CDRL1, CDRL2 and/or CDRL3 comprise a sequence having no more than three or two, preferably no more than one amino acid substitution(s), deletion(s) or insertion(s) compared to SEQ ID NO: 05, SEQ ID NO: 06, or SEQ ID NO: 07, respectively;

characterized in that, said one, preferably two, heavy chain variable domain(s) and said one, preferably two, light chain variable domain(s), each comprise an antibody framework region having at least a portion of a human antibody consensus framework sequence.

In a second aspect, the invention pertains to an antigen binding protein (ABP) or an antigen-binding fragment thereof, capable of binding to fms related tyrosine kinase 3 (FLT3) and that is able to compete with the binding of an ABP of the first aspect to FLT3.

In a third aspect, the invention pertains to a bispecific antigen binding protein (ABP) which comprises a first antigen binding domain capable of binding to the human fms like tyrosine kinase 3 (FLT3) antigen, and a second antigen binding domain capable of binding to the human cluster of differentiation 3 (CD3) antigen, wherein the bispecific ABP:

a. binds to FLT3 with an $EC_{50}$ of lower than 10 nM as determined by analyzing the binding of the bispecific ABP to FLT3 positive cells by flow cytometry using a fluorescent activated cell sorting (FACS) device; and b. binds to CD3 with an $EC_{50}$ of lower than 200 nM as determined by analyzing the binding of the bispecific ABP to CD3 positive cells by flow cytometry using a fluorescent activated cell sorting (FACS) device.

In a fourth aspect, the invention pertains to an isolated nucleic acid comprising a sequence encoding for an ABP, or for an antigen binding fragment or a monomer, such as a heavy or light chain, of an ABP, of the first or second aspect, or encoding for a bispecific ABP according to the third aspect.

In a fifth aspect, the invention pertains to a nucleic acid construct (NAC) comprising a nucleic acid of the fourth aspect and one or more additional sequence features permitting the expression of the encoded antigen binding protein (ABP) or bispecific ABP, or a component of said ABP or bispecific ABP (such as an antibody heavy chain or light chain) in a cell.

In a sixth aspect, the invention pertains to a recombinant host cell comprising a nucleic acid of the fourth aspect or a nucleic acid construct (NAC) according to the second aspect.

In a seventh aspect, the invention pertains to a pharmaceutical composition comprising: (i) an antigen binding protein (ABP) or bispecific ABP of the first to third aspect, or (ii) a nucleic acid of the fourth aspect or a NAC according the fifth, or (iii) a recombinant host cell according to the sixth aspect, and a pharmaceutically acceptable carrier, stabiliser and/or excipient.

In an eighth aspect, the invention pertains to a component for use in medicine, wherein the component is selected from the list consisting of: (i) an antigen binding protein (ABP) or bispecific ABP of the first to third aspect, or (ii) a nucleic acid of the fourth aspect or a NAC according the fifth, or (iii) a recombinant host cell according to the sixth aspect and a pharmaceutical composition according of the seventh aspect.

In a ninth aspect, the invention pertains to a method of enhancing a cell-mediated immune response to a human cell that expresses human FLT3, comprising contacting said cell with an antigen binding protein (ABP) of the first or second aspect, or a bispecific ABP according to the third aspect, or a nucleic acid encoding said ABP or bispecific ABP according to the fourth aspect, in the presence of an immune cell, such as a T-cell or natural killer (NK) cell, thereby enhancing a cell-mediated immune response against said human cell.

In a tenth aspect, the invention pertains to a method for the prevention and/or treatment of a proliferative disorder in a subject, comprising the administration of a therapeutically effective amount of a component recited in the eighth aspect to the subject; and wherein the proliferative disorder is characterized by an expression of human fms like tyrosine kinase 3 (FLT3) in cells associated with the proliferative disorder.

DETAILED DESCRIPTION OF THE INVENTION

In the following, the elements of the invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine two or more of the explicitly described embodiments or which combine the one or more of the explicitly described embodiments with any number of the disclosed and/or preferred elements. Furthermore, any permutations and combinations of all described elements in this application should be considered disclosed by the description of the present application unless the context indicates otherwise.

In the first aspect, the invention pertains to present invention provides an antigen binding protein (ABP) capable of binding to human fms related tyrosine kinase 3 (FLT3), comprising: (i) a heavy chain variable domain comprising the CDRH1 region set forth in SEQ ID NO: 01 (SYWMH), the CDRH2 region set forth in SEQ ID NO: 02 (EIDPSDSYKDYNQKFKD), and the CDRH3 region set forth in SEQ ID NO: 03 (AITITPFDF), or wherein in each case independently the CDRH1, CDRH2 and/or CDRH3 comprise a sequence having no more than three or two, preferably no more than one amino acid substitution(s), deletion(s) or insertion(s) compared to SEQ ID NO: 01, SEQ ID NO: 02, or SEQ ID NO: 03, respectively; or comprising a CDRH1, CDRH2 or CDRH3 sequence having at least 75% sequence identity or at least 80%, preferably 90% sequence identity with SEQ ID NO: 01, SEQ ID NO: 02, or SEQ ID NO: 03; and (ii) a light chain variable domain comprising the CDRL1 region set forth in SEQ ID NO: 05 (RASQSISNNLH), the CDRL2 region set forth in SEQ ID NO: 06 (YASQSIS), and the CDRL3 region set forth in SEQ ID NO: 07 (QQSNTWPYT) or wherein in each case independently CDRL1, CDRL2 and/or CDRL3 comprise a sequence having no more than three or two, preferably no more than one amino acid substitution(s), deletion(s) or insertion(s) compared to SEQ ID NO: 05, SEQ ID NO: 06, or SEQ ID NO: 07, respectively; or comprising a CDRL1, CDRL2 or CDRL3 sequence having at least 75% sequence identity or at least 80% sequence identity with SEQ ID NO: 05, SEQ ID NO: 06, or SEQ ID NO: 07, characterized in that, said heavy chain variable region and said light chain variable region each comprise human variable region framework sequences. Preferably said heavy chain variable domain(s) and said light chain variable domain(s), each comprise an antibody framework region having at least a portion of a human antibody consensus framework sequence.

The present invention also provides novel and highly affine and effective antibody constructs derived from a humanized version of the anti-FLT3 antibody 4G8 (a mouse anti FLT3 antibody fully disclosed in WO 2011/076922), which has been herein for the first time humanized by CDR grafting, meaning the CDR regions of the murine antibody 4G8 are inserted into the framework region of a heavy chain and a light chain of a human antibody. However, the humanized 4G8 antibody was then extensively changed in format, constant and variable regions to obtain the ABP of the invention. In principle any variable human light chain and/or variable heavy chain can serve as scaffold for the CDR grafting. In one illustrative example of a humanized antibody of the invention, the CDR regions of the light chain of the antibody 4G8 (that means the CDR loops of SEQ ID NO: 5 to SEQ ID NO: 7) can be inserted into (the variable domain) of the human κ light sequence IGKV3-15*1 that is deposited in the IMGT/LIGM-database under accession number M23090, see also Ichiyoshi Y., Zhou M., Casali P. A human anti-insulin IgG autoantibody apparently arises through clonal selection from an insulin-specific 'germ-line' natural antibody template. Analysis by V gene segment reassortment and site-directed mutagenesis' J. Immunol. 154(1):226-238 (1995). In another illustrative example of a humanized antibody of the invention, the CDR regions of the heavy chain of the antibody 4G8 (that means the CDR loops of SEQ ID NO: 1 to SEQ ID NO: 3) can be included into the (variable domains) of the heavy chain sequence IGHV1-46*03 which is deposited in the IMGT/LIGM-database under accession number L06612 (See also Watson C. T., et al. Complete haplotype sequence of the human immunoglobulin heavy-chain variable, diversity, and joining genes and characterization of allelic and copy-number variation. Am. J. Hum. Genet. 92(4):530-546 (2013).

The term "antigen binding protein" or "ABP" as used herein means a protein that specifically binds to a target antigen, such as to one or more epitope(s) displayed by or present on a target antigen. The antigen of the ABPs of the invention is FLT3, or in case of bispecific molecules FLT3 and CD3. Typically, an antigen binding protein is an antibody (or a fragment thereof), preferably a bispecific antibody; however other forms of antigen binding protein are also envisioned by the invention. For example, the ABP may be another (non-antibody) receptor protein derived from small and robust non-immunoglobulin "scaffolds", such as those equipped with binding functions for example by using methods of combinatorial protein design (Gebauer & Skerra, 2009; Curr Opin Chem Biol, 13:245). Particular examples of such non-antibody ABPs include: Affibody molecules based on the Z domain of Protein A (Nygren, 2008; FEBS J 275:2668); Affilins based on gamma-B crystalline and/or ubiquitin (Ebersbach et al, 2007; J Mo Biol, 372:172); Affimers based on cystatin (Johnson et al, 2012; Anal Chem 84:6553); Affitins based on Sac7d from *Sulfolobus acidcaldarius* (Krehenbrink et al, 2008; J Mol Biol 383:1058); Alphabodies based on a triple helix coiled coil (Desmet et al, 2014; Nature Comms 5:5237); Anticalins based on lipocalins (Skerra, 2008; FEBS J 275:2677); Avimers based on A domains of various membrane receptors (Silverman et al, 2005; Nat Biotechnol 23:1556); DARPins based on an ankyrin repeat motif (Strumpp et al, 2008; Drug Discov Today, 13:695); Fynomers based on an SH3 domain of Fyn (Grabulovski et al, 2007; J Biol Chem 282:3196); Kunitz domain peptides based on Kunitz domains of various protease inhibitors (Nixon et al, Curr opin Drug Discov Devel, 9:261) and Centyrins and Monobodies based on a 10th type III domain of fibronectin (Diem et al., 2014; Protein Eng Des Sel 27:419 doi: 10.1093/protein/gzu016; Koide & Koide, 2007; Methods Mol Biol 352:95). In the context of an ABP of the present invention, the ABP is provided preferably in a bispecific format comprising antigen binding domains for human FLT3 and human CD3.

The term "complementarity determining region" (or "CDR" or "hypervariable region"), as used herein, refers broadly to one or more of the hyper-variable or complementarily determining regions (CDRs) found in the variable regions of light or heavy chains of an antibody. See, for example: "IMGT", Lefranc et al, 20003, Dev Comp Immunol 27:55; Honegger & Plückthun, 2001, J Mol Biol 309: 657, Abhinandan & Martin, 2008, Mol Immunol 45:3832, Kabat, et al. (1987): Sequences of Proteins of Immunological Interest National Institutes of Health, Bethesda, Md. These expressions include the hypervariable regions as defined by Kabat et al (1983) Sequences of Proteins of Immunological Interest, US Dept of Health and Human Services, or the hypervariable loops in 3-dimensional structures of antibodies (Chothia and Lesk, 1987; J Mol Biol 196:901). The CDRs in each chain are held in close proximity by framework regions and, with the CDRs from the other chain, contribute to the formation of the antigen-binding site. Within the CDRs there are selected amino acids that have been described as the selectivity determining regions (SDRs) which represent the critical contact residues used by the CDR in the antibody-antigen interaction. (Kashmiri, 2005; Methods 36:25).

The term "antibody" generally refers to a proteinaceous binding molecule that is based on an immunoglobulin. Typical examples of such an antibody are derivatives or functional fragments of an immunoglobulin which retain the binding specificity. Techniques for the production of antibodies and antibody fragments are well known in the art. The term "antibody" also includes immunoglobulins (Ig's) of different classes (i.e. IgA, IgG, IgM, IgD and IgE) and subclasses (such as IgG1, lgG2 etc.). As also mentioned above, illustrative examples of an antibody derivative or molecule include Fab fragments, F(ab')2, Fv fragments, single-chain Fv fragments (scFv), diabodies or domain antibodies (Holt L J et al., Trends Biotechnol. 21(11), 2003, 484-490). The definition of the term "antibody" thus also includes embodiments such as chimeric, single chain and humanized antibodies.

An "ABP" as used herein may carry one or more domains that have a sequence with at least about 60%, at least about 70%, at least about 75%, at least about 80%, at least about 85%, at least about 90%, at least about 92%, at least about 95%, at least about 96%, at least about 97%, at least about 98% or at least about 99% sequence identity with a corresponding naturally occurring domain of an immunoglobulin M, an immunoglobulin G, an immunoglobulin A, an immunoglobulin D or an immunoglobulin E. It is noted in this regard, the term "about" or "approximately" as used herein means within a deviation of 20%, such as within a deviation of 10% or within 5% of a given value or range.

"Percent (%) sequence identity" as used in the present invention means the percentage of pair-wise identical residues—following homology alignment of a sequence of a polypeptide of the present invention with a sequence in question—with respect to the number of residues in the longer of these two sequences. Alignment for purposes of determining percent amino acid sequence identity can be achieved in various ways that are within the skill in the art, for instance, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared. The same is true for nucleotide sequences disclosed herein.

An "immunoglobulin" when used herein, is typically a tetrameric glycosylated protein composed of two light (L) chains of approximately 25 kDa each and two heavy (H) chains of approximately 50 kDa each. Two types of light chain, termed lambda and kappa, may be found in immunoglobulins. Depending on the amino acid sequence of the constant domain of heavy chains, immunoglobulins can be assigned to five major classes: A, D, E, G, and M, and several of these may be further divided into subclasses (isotypes), e.g., IgG1, lgG2, IgG3, IgG4, IgA1, and IgA2. An IgM immunoglobulin consists of 5 of the basic heterotetramer unit along with an additional polypeptide called a J chain, and contains 10 antigen binding sites, while IgA immunoglobulins contain from 2-5 of the basic 4-chain units which can polymerize to form polyvalent assemblages in combination with the J chain. In the case of IgGs, the 4-chain unit is generally about 150,000 Daltons.

In the IgG class of immunoglobulins, there are several immunoglobulin domains in the heavy chain. By "immunoglobulin (Ig) domain" herein is meant a region of an immunoglobulin having a distinct tertiary structure. In the context of IgG antibodies, the IgG isotypes each have three CH regions: "CH1" refers to positions 118-220, "CH2" refers to positions 237-340, and "CH3" refers to positions 341-447 according to the EU index as in Kabat et al. By "hinge" or "hinge region" or "antibody hinge region" or "immunoglobulin hinge region" or "H" herein is meant the flexible polypeptide comprising the amino acids between the first and second constant domains of an antibody. Structurally, the IgG CH1 domain ends at EU position 220, and the IgG CH2 domain begins at residue EU position 237. Thus, for IgG the hinge is herein defined to include positions 221 (D221 in IgG1) to 236 (G236 in IgG1), wherein the numbering is according to the EU index as in Kabat et al. The constant heavy chain, as defined herein, refers to the N-terminus of the CH1 domain to the C-terminus of the CH3 domain, thus comprising positions 118-447, wherein numbering is according to the EU index.

The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable regions", "HVR," or "HV," or "complementarity determining regions" (CDRs). The more conserved (i.e., non-hypervariable) portions of the variable domains are called the "framework" regions (FR). The variable domains of naturally occurring heavy and light chains each include four FR regions, largely adopting a β-sheet configuration, connected by three hypervariable regions, which form loops connecting, and in some cases forming part of, the β-sheet structure. The hypervariable regions in each chain are held together in close proximity by the FR and, with the hypervariable regions from the other chain, contribute to the formation of the antigen-binding site (see Kabat et al., see below). Generally, naturally occurring immunoglobulins include six CDRs (see below); three in the VH (CDRH1, CDRH2, CDRH3), and three in the VL (CDRL1, CDRL2, CDRL3). In naturally occurring immunoglobulins, CDRH3 and CDRL3 display the most extensive diversity of the six CDRs, and CDRH3 in particular is believed to play a unique role in conferring fine specificity to immunoglobulins. The constant domains are not directly involved in antigen binding, but exhibit various effector functions, such as, for example, antibody-dependent, cell-mediated cytotoxicity and complement activation.

The terms "VH" (also referred to as VH) and "VL" (also referred to as VL) are used herein to refer to the heavy chain variable domain and light chain variable domain respectively of an immunoglobulin. An immunoglobulin light or heavy chain variable region consists of a "framework" region interrupted by three hypervariable regions. Thus, the term "hypervariable region" refers to the amino acid residues of an antibody which are responsible for antigen binding. The hypervariable region includes amino acid residues from a "Complementarity Determining Region" or "CDR". There are three heavy chains and three light chain CDRs (or CDR regions) in the variable portion of an immunoglobulin. Thus, "CDRs" as used herein refers to all three heavy chain CDRs (CDRH1, CDRH2 and CDRH3), or all three light chain CDRs (CDRL1, CDRL2 and CDRL3) or both all heavy and all light chain CDRs, if appropriate. Three CDRs make up the binding character of a light chain variable region and three make up the binding character of a heavy chain variable region. CDRs determine the antigen specificity of an immunoglobulin molecule and are separated by amino acid sequences that include scaffolding or framework regions. The exact definitional CDR boundaries and lengths are subject to different classification and numbering systems. The structure and protein folding of the antibody may mean that other residues are considered part of the antigen binding region and would be understood to be so by a skilled person. CDRs provide the majority of contact residues for the binding of the immunoglobulin to the antigen or epitope.

CDR3 is typically the greatest source of molecular diversity within the antibody-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988. One of skill in the art will recognize that each subunit structure, e.g., a CH, VH, CL, VL, CDR, FR structure, includes active fragments, e.g., the portion of the VH, VL, or CDR subunit binds to the antigen, i.e., the antigen-binding fragment, or, e.g., the portion of the CH subunit that binds to and/or activates, e.g., an Fc receptor and/or complement. The CDRs typically refer to the Kabat CDRs, as described in Sequences of Proteins of immunological Interest, US Department of Health and Human Services (1991), eds. Kabat et al. Another standard for characterizing the antigen binding site is to refer to the hypervariable loops as described by Chothia. See, e.g., Chothia, et al. (1992; J. MoI. Biol. 227:799-817; and Tomlinson et al. (1995) EMBO J. 14:4628-4638. Still another standard is the AbM definition used by Oxford Molecular's AbM antibody modelling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). Embodiments described with respect to Kabat CDRs can alternatively be implemented using similar described relationships with respect to Chothia hypervariable loops or to the AbM-defined loops.

The corresponding immunoglobulin mu heavy chain, gamma heavy chain, alpha heavy chain, delta heavy chain, epsilon heavy chain, lambda light chain or kappa light chain may be of any species, such as a mammalian species, including a rodent species, an amphibian, e.g. of the subclass Lissamphibia that includes e.g. frogs, toads, salamanders or newts or an invertebrate species. Examples of mammals include, but are not limited to, a rat, a mouse, a rabbit, a guinea pig, a squirrel, a hamster, a hedgehog, a platypus, an American pika, an armadillo, a dog, a lemur, a goat, a pig, a cow, an opossum, a horse, a bat, a woodchuck, an orang-utan, a rhesus monkey, a woolly monkey, a macaque, a chimpanzee, a tamarin (*Saguinus oedipus*), a marmoset or a human.

As mentioned herein an immunoglobulin is typically a glycoprotein that includes at least two heavy (H) chains and two light (L) chains linked by disulfide bonds, or an antigen binding portion thereof. Each heavy chain has a heavy chain variable region (abbreviated herein as VH) and a heavy chain constant region. In some embodiments the heavy chain constant region includes three domains, CH1, CH2 and CH3. Each light chain has a light chain variable region (abbreviated herein as VL) and a light chain constant region. The light chain constant region includes one domain, CL. The VH and VL regions can be further subdivided into regions of hypervariability, termed complementarity determining regions (CDR), interspersed with regions that are more conserved, termed framework regions (FR). The CDRs contain most of the residues responsible for specific interactions of the antibody with the antigen. Each VH and VL has three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an epitope of an antigen.

"Framework Region" or "FR" residues are those variable domain residues other than the hypervariable region. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

The terms "Fab", "Fab region", "Fab portion" or "Fab fragment" are understood to define a polypeptide that includes a VH, a CH1, a VL, and a CL immunoglobulin domain. Fab may refer to this region in isolation, or this region in the context of an ABP, as well as a full length immunoglobulin or immunoglobulin fragment. Typically a Fab region contains an entire light chain of an antibody. A Fab region can be taken to define "an arm" of an immunoglobulin molecule. It contains the epitope-binding portion of that Ig. The Fab region of a naturally occurring immunoglobulin can be obtained as a proteolytic fragment by a papain-digestion. A "F(ab')2 portion" is the proteolytic fragment of a pepsin-digested immunoglobulin. A "Fab' portion" is the product resulting from reducing the disulfide bonds of an F(ab')2 portion. As used herein the terms "Fab", "Fab region", "Fab portion" or "Fab fragment" may further include a hinge region that defines the C-terminal end of the antibody arm. This hinge region corresponds to the hinge region found C-terminally of the CH1 domain within a full-length immunoglobulin at which the arms of the ABP can be taken to define a Y. The term hinge region is used in the art because an immunoglobulin has some flexibility at this region. A "Fab heavy chain" as used herein is understood as that portion or polypeptide of the Fab fragment that comprises a VH and a CH1, whereas a "Fab light chain" as used herein is understood as that portion or polypeptide of the Fab fragment that comprises a VL, and a CL.

The term "Fc region" or "Fc fragment" is used herein to define a C-terminal region of an immunoglobulin heavy chain, including native-sequence Fc regions and variant Fc regions. The Fc part mediates the effector function of antibodies, e.g. the activation of the complement system and of Fc-receptor bearing immune effector cells, such as NK cells. In human IgG molecules, the Fc region is generated by papain cleavage N-terminal to Cys226. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the ABP, or by recombinantly engineering the nucleic acid encoding a heavy chain of the ABP. Native-sequence Fc regions include mammalian, e.g. human or murine, IgG1, IgG2 (IgG2A, IgG2B), IgG3 and IgG4. The Fc region contains two or three constant domains, depending on the class of the antibody. In embodiments where the immunoglobulin is an IgG the Fc region has a CH2 and a CH3 domain.

The term "single-chain variable fragment" (scFv) is used herein to define an antibody fragment, in which the variable regions of the heavy (VH) and light chains (VL) of a immunoglobulin are fused together, by a short linker peptide of ten to about 25 amino acids. The linker is usually rich in glycine for flexibility, as well as serine or threonine for solubility, and can either connect the N-terminus of the VH with the C-terminus of the VL, or connect the N-terminus of the VL with the C-terminus of the VH. The scFv fragment retains a specific antigen binding site but lacks constant domains of immunoglobulins.

The term "epitope", also known as the "antigenic determinant", refers to the portion of an antigen to which an antibody or T-cell receptor specifically binds, thereby forming a complex. Thus, the term "epitope" includes any molecule or protein determinant capable of specific binding to an immunoglobulin or T-cell receptor. The binding site(s) (paratope) of an ABP described herein may specifically bind to/interact with conformational or continuous epitopes, which are unique for the target structure. Epitopic determinants usually consist of chemically active surface groupings of molecules such as amino acids or sugar side chains and usually have specific three dimensional structural characteristics, as well as specific charge characteristics. In some embodiments, epitope determinants include chemically active surface groupings of molecules such as amino acids, sugar side chains, phosphoryl, or sulfonyl, and, in certain embodiments, may have specific three-dimensional structural characteristics, and/or specific charge characteristics. With regard to polypeptide antigens a conformational or discontinuous epitope is characterized by the presence of two or more discrete amino acid residues, separated in the primary sequence, but assembling to a consistent structure on the surface of the molecule when the polypeptide folds into the native protein/antigen (SeIa, M., Science (1969) 166, 1365-1374; Laver, W. G., et al. Cell (1990) 61, 553-556). The two or more discrete amino acid residues contributing to the epitope may be present on separate sections of one or more polypeptide chain(s). These residues come together on the surface of the molecule when the polypeptide chain(s) fold(s) into a three-dimensional structure to constitute the epitope. In contrast, a continuous or linear epitope consists of two or more discrete amino acid residues, which are present in a single linear segment of a polypeptide chain.

The term "specific" in this context, or "specifically binding", also used as "directed to", means in accordance with this invention that the antibody or immune receptor fragment is capable of specifically interacting with and/or binding to a specific antigen or ligand or a set of specific antigens or ligands but does not essentially bind to other antigens or ligands. Such binding may be exemplified by the specificity of a "lock-and-key-principle". Antibodies are said to "bind to the same epitope" if the antibodies cross-compete so that only one antibody can bind to the epitope at a given point of time, i.e. one antibody prevents the binding or modulating effect of the other.

The term "isolated ABP" as used herein refers to an ABP that has been identified and separated and/or recovered from a component of its natural environment. Contaminant components of its natural environment are matter that would interfere with diagnostic or therapeutic uses for the antibody, and may include enzymes, hormones, and other proteinaceous or nonproteinaceous solutes. In some embodiments the ABP is purified to greater than 95% by weight of antibody as determined by the Lowry method, such as more than 99% by weight. In some embodiments the antibody is purified to homogeneity as judged by SDS-PAGE under reducing or nonreducing conditions using Coomassie blue or, preferably, silver stain. An isolated ABP may in some embodiments be present within recombinant cells with one or more component(s) of the antibody's natural environment not being present. Typically an isolated antibody is prepared by at least one purification step.

A (recombinant) ABP of the invention that binds to FLT3 and/or FLT3-expressing cancer cells as described herein may be used in any suitable recombinant antibody format, for example as an Fv fragment, a scFv, a univalent antibody lacking a hinge region, a minibody, a Fab fragment, a Fab' fragment, a F(ab')2 fragment. A recombinant ABP of the invention may also comprise constant domains (regions) such a human IgG constant region, a CH1 domain (as Fab fragments do) and/or an entire Fc region. Alternatively, an ABP of the invention may also be a full length (whole) antibody, preferably in a bispecific format.

There are a number of possible mechanisms by which antibodies mediate cellular effects, including anti-proliferation via blockage of needed growth pathways, intracellular signaling leading to apoptosis, enhanced down regulation and/or turnover of receptors, complement-dependent cytotoxicity (CDC), antibody-dependent cell-mediated cytotoxicity (ADCC), antibody-dependent cell-mediated phagocytosis (ADCP) and promotion of an adaptive immune response (Cragg et al, 1999, Curr Opin Immunol 11 541-547, Glennie et al, 2000, Immunol Today 21 403-410). Antibody efficacy may be due to a combination of these mechanisms, and their relative importance in clinical therapy for oncology appears to be cancer dependent.

The importance of FcγR-mediated effector functions for the activity of some antibodies has been demonstrated in mice (Clynes et al, 1998, Proc Natl Acad Sci USA 95 652-656, Clynes et al, 2000, Nat Med 6 443-446,), and from observed correlations between clinical efficacy in humans and their allotype of high (V158) or low (F158) affinity polymorphic forms of FcγRIIIa (Cartron et al, 2002, Blood 99 754-758, Weng & Levy, 2003, Journal of Clinical Oncology, 21 3940-3947). Together these data suggest that an antibody that is optimized for binding to certain FcγRs may better mediate effector functions, and thereby destroy target cells more effectively in patients. Thus a promising means for enhancing the anti-tumor potency of antibodies is via enhancement of their ability to mediate cytotoxic effector functions such as ADCC, ADCP, and CDC Additionally, antibodies can mediate anti-tumor mechanism via growth inhibitory or apoptotic signaling that may occur when an antibody binds to its target on tumor cells. Such signaling may be potentiated when antibodies are presented to tumor cells bound to immune cells via FcγR. Therefore, increased affinity of antibodies to FcγRs may result in enhanced antiproliferative effects.

Some success has been achieved at modifying antibodies with selectively enhanced binding to FcγRs to provide enhanced effector function. Antibody engineering for optimized effector function has been achieved using amino acid modifications (see for example US patent application US 2004-0132101 or US patent application 2006-0024298.

An ABP of the invention is capable of binding to human FLT3. The term "fms related tyrosine kinase 3" or "FLT3" are used interchangeably herein, and include variants, isoforms and species homologs of human FLT3. Human FLT3 protein has the UniProt accession number P36888 (version of 9 Sep. 2018). The gene for human FLT3 is located on chromosome 13 and has the HGNC accession of HGNC: 3765 (www.genenames.org—HGNC version of Sep. 9, 2018). Human FLT 3 is also known under the names CD135, FLK2, STK1. However, antibodies of the invention may, in certain preferred cases, not cross-react with FLT3 from species other than human.

To determine the epitope, standard epitope mapping methods known in the art may be used. For example, fragments (peptides) of FLT3 (e.g. synthetic peptides) that bind the antibody can be used to determine whether a candidate antibody or antigen-binding fragment thereof binds the same epitope. For linear epitopes, overlapping peptides of a defined length (e.g., 8 or more amino acids) are synthesized. The peptides can be offset by 1 amino acid, such that a series of peptides covering every 8 amino acid fragment of the FLT3 protein sequence are prepared. Fewer peptides can be prepared by using larger offsets, e.g., 2 or 3 amino acids. In addition, longer peptides (e.g., 9-, 10- or 11-mers) can be synthesized. Binding of peptides to antibodies or antigen-binding fragments can be determined using standard methodologies including surface plasmon resonance (BIACORE) and ELISA assays. For examination of conformational epitopes, larger FLT3 fragments can be used. Other methods that use mass spectrometry to define conformational epitopes have been described and can be (see, e.g., Baerga-Ortiz et al., Protein Science 11:1300-1308, 2002 and references cited therein). Still other methods for epitope determination are provided in standard laboratory reference works, such as Unit 6.8 ("Phage Display Selection and Analysis of B-cell Epitopes") and Unit 9.8 ("Identification of Antigenic Determinants Using Synthetic Peptide Combinatorial Libraries") of Current Protocols in Immunology, Coligan et al., eds., John Wiley & Sons. Epitopes can be confirmed by introducing point mutations or deletions into a known epitope, and then testing binding with one or more antibodies or antigen-binding fragments to determine which mutations reduce binding of the antibodies or antigen-binding fragments.

The ABPs of the invention in some preferred embodiments comprise in their first antigen binding domain a heavy chain variable region comprising human framework regions of the allele IGHV1-46, preferably IGHV1-46*3. Within the light chains the ABPs of the invention comprise variable regions having a framework of IGKV3D-15*01. In some embodiments the antibody of the invention is a fully grafted humanized antibody, which is denoted V0-V6 and comprises the heavy- and light chain variable domain sequences of SEQ ID NO: 76 and 77 respectively. However, it is one achievement of the present invention to provide mutated variants of a humanized anti-FLT3 antibody with improved binding affinity, avidity and/or activity for the recruitment and activation of T-cells and T cell mediated anti-tumor cytotoxicity. Therefore, in accordance with the present invention it is preferred that the ABP of the invention in the FLT3 specific first antigen binding domain, the ABP comprises the heavy chain variable regions with mutation(s) at one or more positions selected from 16, 18, 19, 20, 22, 48, 57, 60, 69, 70, 75, 76, 78, 80, 81, 87, and 108, according to the Kabat numbering. Most preferably the mutations are any one or any combination, or all of, K16G, V18L, K19R, V20L, K22A, M48I, K57T, N60A, M69I, T70S, T75K, S76N, V78L, M80L, E81Q, S87A, and T108L, according to the Kabat numbering. In addition the ABP of the invention may further comprise in its FLT3 specific first antigen binding domain a variable light chain sequence having one or more mutations selected from 49, 87, and 55, preferably Y49K, I55A, and Y87F, wherein the numbering is according to the Kabat system. In some embodiments a ABP of the invention in its first antigen binding domain may include the heavy chain variable sequence mutations, and preferably as only mutations, K16G, V18L, K19R, V20L, K22A, K57T, N60A, M69I, T70S, T75K, S76N, V78L, M80L, E81Q, S87A, and T108L, and the light chain variable sequence mutation I55A, or no mutation in the variable light chain region. Or the ABP of the invention may include K16G, V18L, K19R, V20L, K22A, M69I, T70S, T75K, S76N, V78L, M80L, E81Q, S87A, T108L, preferably as only mutations, and no mutation in the light chain variable sequence. Another example pertains to an ABP which comprises in no mutation in the anti-FLT3 binding domain heavy chain variable sequence, and the I55A mutation in the corresponding light chain variable sequence. Further preferred are ABPs of the invention comprising in the anti-FLT3 first antigen binding domain a heavy chain variable sequence with a mutation at position 48, preferably 48I, and in the corresponding light chain variable sequence the mutations 49K and 87F. The numbering according to the Kabat system.

Yet another embodiment of the invention pertains to ABPs comprising in their first antigen binding domain directed at FLT3 an antibody heavy chain variable region and an antibody light chain variable region, wherein the heavy chain variable region comprises the amino acid sequence having a sequence identity of at least 70%, 80%, 90%, 95%, 96%, 97%, 98%, or 99%, preferably 100%, to an amino acid sequence selected from SEQ ID NO: 15, 17, 19, 21, 23 or 76, or, in each case independently, optionally with no more than ten, nine, eight, seven, six, five, four, preferably no more than three, two or one, amino acid substitution(s), insertion(s) or deletion(s) compared to these sequences; and/or wherein the light chain variable region comprises the amino acid sequence having a sequence identity of at least 70%, 80%, 90%, 95%, 96%, 97%, 98%, or 99%, preferably 100%, to the amino acid sequence selected from SEQ ID NO: 16, 18, 20, 22, 24 or 77, or, in each case independently, optionally with no more than ten, nine, eight, seven, six, five, four, preferably no more than three, two or one, amino acid substitution(s), insertion(s) or deletion(s) compared to these sequences. Wherein such amino acid substitutions are preferably conservative substitutions. Most preferably the light and the heavy chain are in these ABPs paired in accordance with the herein disclosed antibodies in table below. In addition, Preferred ABPs according to the invention include in the heavy chain variable region the amino acid positions 16, 18, 19, 20, 22, 48, 57, 60, 69, 70, 75, 76, 78, 80, 81, 87, and 108 as provided in any one of SEQ ID NO: 15, 17, 19, 21 or 23; and/or include in the light chain variable region the amino acid positions 49, 55, and 87 as provided in any one of SEQ ID NO: 16, 18, 20, 22 or 24; wherein the numbering is according to the Kabat system.

In some embodiments of the invention the heavy chain variable region of the ABP comprises an amino acid sequence having a sequence identity of at least 85%, at least 90%, or at least 95% to the amino acid sequence set forth in SEQ ID NO: 21, and the light chain variable region comprises an amino acid sequence having a sequence identity of at least 95% to the amino acid sequence set forth in SEQ ID NO: 22.

In some embodiments of the invention the heavy chain variable region comprises an amino acid sequence having a sequence identity of at least 85%, at least 90%, or at least 95% to the amino acid sequence set forth in SEQ ID NO: 76, and the light chain variable region comprises an amino acid sequence having a sequence identity of at least 95% to the amino acid sequence set forth in SEQ ID NO: 77.

In some particular embodiments of the invention, the ABP is preferred wherein the heavy chain variable region comprises 48I, and wherein the light chain variable region comprises 87F, wherein the numbering is according to the Kabat system. Even more preferred is an ABP of the invention wherein the light chain variable region further comprises 49K, wherein the numbering is according to the Kabat system.

ABPs of the invention are, as explained herein, preferably bispecific molecules wherein said second antigen binding domain binds to CD3, preferably wherein said second antigen binding domain is fused to the heavy chain of the first antibody binding domain. It is preferred that the second antigen binding domain comprises an scFv fragment comprising an amino acid sequence having at least 70%, 80%, 90%, 95%, 96%, 97%, 98%, or 99%, preferably 100%, sequence identity to, or, in each case independently, optionally with no more than ten, nine, eight, seven, six, five, four, preferably no more than three, two or one, amino acid substitution(s), insertion(s) or deletion(s) compared to, a sequence selected from SEQ ID NO: 14, 25, 26 and 27.

An ABP in accordance with the invention in some embodiments may be an ABP comprising at least one antibody heavy chain having an amino acid sequence with at least 70%, 80%, 90%, 95%, 96%, 97%, 98%, or 99%, preferably 100%, sequence identity to, or having no more than twenty, fifteen, ten, nine, eight, seven, six, four, preferably three or two, preferably no more than one amino acid substitution(s), deletion(s) or insertion(s) compared to, a sequence selected from selected from SEQ ID NO: 28, 30, 32, 34, 36, 38, 40, 42, 44, 46, 48, 50, 52, 54, 56, 58, 60, 62, 64, 66, 68, 70, 72, 74 and 78; and/or comprising at least one antibody light chain having an amino acid sequence with at least 70%, 80%, 90%, 95%, 96%, 97%, 98%, or 99%, preferably 100%, sequence identity to, or having no more than twenty, fifteen, ten, nine, eight, seven, six, four, preferably three or two, preferably no more than one amino acid substitution(s), deletion(s) or insertion(s) compared to, a sequence selected from selected from SEQ ID NO: 29, 31, 33, 35, 37, 39, 41, 43, 45, 47, 49, 51, 53, 55, 57, 59, 61, 63, 65, 67, 69, 71, 73, 75 and 79. In preferred embodiments an ABP of the invention is an ABP as described in this paragraph, with the provision that the light and the heavy chain are paired as indicated for the herein disclosed antibodies in table 1 below.

The ABP of the invention is preferably an ABP comprising one, preferably two, antibody heavy chains and one, preferably two, antibody light chains, each comprising an amino acid sequence with at least 70%, 80%, 90%, 95%, 96%, 97%, 98%, or 99%, preferably 100%, sequence identity to, or having no more than twenty, fifteen, ten, nine, eight, seven, six, four, preferably three or two, preferably no more than one amino acid substitution(s), deletion(s) or insertion(s) compared to:

a. a sequence selected from SEQ ID NO: 28 for the heavy chain and SEQ ID NO: 29 for the light chain (antibody V1-V6);

b. a sequence selected from SEQ ID NO: 30 for the heavy chain and SEQ ID NO: 31 for the light chain (antibody V2-V6);

c. a sequence selected from SEQ ID NO: 32 for the heavy chain and SEQ ID NO: 33 for the light chain (antibody V3-V6);

d. a sequence selected from SEQ ID NO: 34 for the heavy chain and SEQ ID NO: 35 for the light chain (antibody V4-V6);

e. a sequence selected from SEQ ID NO: 36 for the heavy chain and SEQ ID NO: 37 for the light chain (antibody V5-V6);

f. a sequence selected from SEQ ID NO: 38 for the heavy chain and SEQ ID NO: 39 for the light chain (antibody V1-V7);

g. a sequence selected from SEQ ID NO: 40 for the heavy chain and SEQ ID NO: 41 for the light chain (antibody V2-V7);

h. a sequence selected from SEQ ID NO: 42 for the heavy chain and SEQ ID NO: 43 for the light chain (antibody V3-V7);

i. a sequence selected from SEQ ID NO: 44 for the heavy chain and SEQ ID NO: 45 for the light chain (antibody V4-V7);

j. a sequence selected from SEQ ID NO: 46 for the heavy chain and SEQ ID NO: 47 for the light chain (antibody V5-V7);

k. a sequence selected from SEQ ID NO: 48 for the heavy chain and SEQ ID NO: 49 for the light chain (antibody V1-V8);

l. a sequence selected from SEQ ID NO: 50 for the heavy chain and SEQ ID NO: 51 for the light chain (antibody V2-V8);

m. a sequence selected from SEQ ID NO: 52 for the heavy chain and SEQ ID NO: 53 for the light chain (antibody V3-V8);
n. a sequence selected from SEQ ID NO: 54 for the heavy chain and SEQ ID NO: 55 for the light chain (antibody V4-V8);
o. a sequence selected from SEQ ID NO: 56 for the heavy chain and SEQ ID NO: 57 for the light chain (antibody V5-V8);
p. a sequence selected from SEQ ID NO: 58 for the heavy chain and SEQ ID NO: 59 for the light chain (antibody V1-V9);
q. a sequence selected from SEQ ID NO: 60 for the heavy chain and SEQ ID NO: 61 for the light chain (antibody V2-V9);
r. a sequence selected from SEQ ID NO: 62 for the heavy chain and SEQ ID NO: 63 for the light chain (antibody V3-V9);
s. a sequence selected from SEQ ID NO: 64 for the heavy chain and SEQ ID NO: 65 for the light chain (antibody V4-V9);
t. a sequence selected from SEQ ID NO: 66 for the heavy chain and SEQ ID NO: 67 for the light chain (antibody V5-V9);
u. a sequence selected from SEQ ID NO: 68 for the heavy chain and SEQ ID NO: 69 for the light chain (antibody V6-V6);
v. a sequence selected from SEQ ID NO: 70 for the heavy chain and SEQ ID NO: 71 for the light chain (antibody V6-V7);
w. a sequence selected from SEQ ID NO: 72 for the heavy chain and SEQ ID NO: 73 for the light chain (antibody V6-V8);
x. a sequence selected from SEQ ID NO: 74 for the heavy chain and SEQ ID NO: 75 for the light chain (antibody V6-V9).
y. a sequence selected from SEQ ID NO: 78 for the heavy chain and SEQ ID NO: 79 for the light chain (antibody V0-V6).

Throughout the present disclosure the preferred antibody variable chain variants are referred to with the denomination "Vx" or "Vx-Vy". The phrase "Vx", where x may be o, 1, 2, 3, 4, 5, 6, 7, 8, or 9, denotes the variable region variant disclosed in the present invention according to table 1, or the example section, in particular as described in example 3. In particular, the humanized 4G8 FLT3 antigen binding domain is detonated as Variant 0 or V0. The terms V0, V1, V2, V3, V4, V5, and V6 may refer to variable region variants of the FLT3 binding site of the antibodies of the invention. On the other hand the terms V6, V7, V8, and V9 refer to certain variants of the CD3 binding site of the antibodies (the bispecifics) of the invention. The term "Vx-Vy" is used herein to describe the preferred bispecific FLT3×CD3 ABPs of the invention wherein Vx denotes the anti FLT3 binding site variant and Vy denotes the anti-CD3 binding site variant. In this context Vx may be one of V0, V1, V2, V3, V4, V5, and V6; whereas Vy may be one of V6, V7 V8 or V9. It is understood that V6 may be used both in context of an anti-FLT3 binding site variant or an anti-CD3 binding site variant of the invention. The use will be apparent from the context. The sequence of the variants and the overall construct nomenclature becomes also apparent from table 1 below.

The heavy and light chains of the above ABP (a.) to (y.) are preferably paired with each other. Preferred ABP of the invention are selected in accordance to their ability to induce T-cell mediated killing and/or growth inhibition of leukemic cancer cells, for example according to the data provided in the example section of this disclosure. For example certain constructs such as V5-V9 show the highest combined FLT3 and CD3 affinity. While each construct comprising either the CD3 or FLT3 antigen binding domain of V5-V9 is a preferred ABP in this regard, some applications may require such a strong FLT3/CD3 binder. However, also antibodies having a slightly reduced affinity, but therefore better tolerability (humanization) or biological activity (anti-cancer activity) are also included as preferred constructs of the invention. Therefore, the above depicted ABPs a. to x. are all preferred, in particular all humanized variants not comprising the FLT3 (first) antigen binding domain of V6-V6.

Another aspect of the invention then pertains to a bispecific antigen binding protein (ABP) which comprises a first antigen binding domain capable of binding to the human fms like tyrosine kinase 3 (FLT3) antigen, and a second antigen binding domain binding to the human cluster of differentiation 3 (CD3) antigen. The bispecific ABP as described for this aspect may in preferred embodiments comprise any one of or a combination of the embodiments of the ABP described herein before. The ABP as described herein before may in all its embodiments be a bispecific ABP as described herein in the following.

In certain embodiments it is preferred that the bispecific ABP, binds to FLT3 with an EC50 of lower than 10 nM, preferably lower than 9 nM, more preferably lower than 8 nM, more preferably lower than 7 nM, more preferably lower than 6 nM, or lower than 5.5 nM. Alternatively or additionally the bispecific ABP of the invention binds FLT3 with an EC50 of higher than 0.5 nM, more preferably higher than 1 nM, more preferably higher than 1.3 nM, more preferably higher than 2 nM, more preferably higher than 3 nM, or 4 nM, or higher than 4.5 nM. Further alternatively or additionally, the bispecific ABP according to the invention binds to FLT3 with an EC50 of lower than 10 nM and higher than 0.5 nM, more preferably of lower than 9 nM and higher than 1 nM, preferably of lower than 8 nM and higher than 1.3 nM, preferably of lower than 7 nM and higher than 3 nM, preferably of lower than 6 nM and higher than 4 nM, preferably of lower than 5.5 nM and higher than 4.5 nM. The EC50 of the binding of the bispecific ABP to FLT3 is as determined by analyzing the binding of the bispecific ABP to FLT3 positive cells by flow cytometry using a fluorescent activated cell sorting (FACS) device; preferably wherein the FLt3 positive cells are B cell precursor leukemia cells, preferably NALM-16 cells (as deposited under ACC 680 at the DSMZ); and/or preferably wherein the binding is detected using a fluorescent labeled secondary antibody; and/or wherein the bispecific ABP is incubated with the FLT3 positive cells for about 30 min before flow cytometry. In this embodiment the invention pertains to antibodies for which it was surprisingly discovered that a certain preferred binding affinity to the target antigen binding molecule might translate into an improved therapeutic effect. In this respect as shown in the examples, certain antibodies although having a lower affinity to FLT3 compared to other antibodies have a significantly improved effect in mediating cytotoxicity. In some preferred aspects and embodiments, antibodies falling with such an affinity "window" as disclosed herein are preferred.

In addition or alternatively, the bispecific ABP of the invention binds FLT3 with an kD of less than 50 µM, more preferably of less than 20 µM, more preferably less than 10 µM, more preferably less than 5 µM, more preferably less than 1 µM; and/or binds FLT3 with an kD of more than 50 nM, more preferably of more than 100 nM, more preferably of more than 160 nM, more preferably of more than 200 NM, more preferably of more than 300 nM. Most preferably the bispecific ABP of the invention binds FLT3 in a certain preferred ranger, such as with an kD of less than 50 µM and more than 50 nM, more preferably of less than 20 µM and more than 100 nM, more preferably less than 10 µM and more than 160 nM, more preferably less than 5 µM and more than 200 nM, more preferably less than 1 µm and more than 300 nM; wherein the kD is as measured by surface plasmon resonance, for example in a BIAcore Affinity Assay, such as provided in the example section.

In another embodiment the bispecific ABP in accordance with the invention binds to CD3 with an EC50 of lower than 200 nM, preferably lower than 90 nM, more preferably lower than 50 nM, more preferably lower than 20 nM, more preferably lower than 15 nM, and/or binds to CD3 with an EC50 of higher than 1 nM, preferably higher than 2 nM, more preferably higher than 4.1 nM, more preferably higher than 6 nM, more preferably higher than 8 nM; and/or in some embodiments certain ranges of affinity for the CD3 binding are preferred, such as an ABP that binds to CD3 with an EC50 of lower than 200 nM and higher than 1 nM, preferably lower than 200 nM and higher than 2 nM, more preferably lower than 90 nM and higher than 4.1 nM, more preferably lower than 20 nM and higher than 6 nM, more preferably lower than 15 nM and higher than 8 nM. The EC50 of the binding of the bispecific ABP to CD3 is as determined by analyzing the binding of the bispecific ABP to CD3 positive cells by flow cytometry using a fluorescent activated cell sorting (FACS) device; preferably wherein the CD3 positive cells are T cell leukemia cells, preferably Jurkat cells (as deposited under ACC 282 at the DSMZ); and/or preferably wherein the binding is detected using a fluorescent labeled secondary antibody; and/or wherein the bispecific ABP is incubated with the CD3 positive cells for about 30 min before flow cytometry.

Alternatively or additionally, in some embodiments, the ABP of the invention are characterized by their ability to kill, or inhibit proliferation of, cancer cells expressing human FLT3, such as ALL or AML cells. Hence, preferred in context of the invention is a bispecific ABP as described herein which inhibits proliferation and/or viability of leukemic blood mononuclear cells of a patient suffering from acute leukemia in an in-vitro assay compared to an unrelated control to equal or less than 50%, more preferably to equal or less than 40%, more preferably to equal or less than 30%, most preferably to equal or less than 25%. Such preferred bispecific ABP of the invention are exemplified in V3-V6, V3-V8, V3-V9, V4-V6, V4-V8, V4-V9, V5-V6, V5-V8, and V5-V9, and their herein disclosed variants.

Further, some embodiments of the invention pertain to ABPs that compete with an ABP of the invention, for binding to FLT3, e.g. to competitively inhibit binding of an inventive antibody to FLT3. To determine competitive inhibition, a variety of assays known to one of ordinary skill in the art can be employed. For example, cross-competition assays can be used to determine if an antibody or antigen-binding fragment thereof competitively inhibits binding to FLT3 by another antibody or antigen-binding fragment thereof. These include cell-based methods employing flow cytometry or solid phase binding analysis. Other assays that evaluate the ability of antibodies or antigen-binding fragments thereof to cross-compete for FLT3 molecules that are not expressed on the surface of cells, in solid phase or in solution phase, also can be used.

An ABP according to the invention may have two chains, a shorter chain, which may in some embodiments be a light chain, and a main chain, which may in some embodiments also be addressed as the heavy chain. The ABP is usually a dimer of these two chains.

An ABP of the invention may preferably be a bispecific ABP. The bispecific ABP may comprise (i) a variable region comprising a heavy chain variable domain and a light chain variable domain as defined in any one of the preceding claims, wherein said variable region comprises a first antigen binding domain capable of binding to human FLT3 and (ii) a heavy chain variable region and a light chain variable region of an ABP comprising a second antigen binding domain. It is understood that the binding site for FLT3 is preferably a binding site of a FLT3-binding antibody of the invention described herein.

A "bispecific" or "bifunctional" ABP is an ABP that has two different epitope/antigen binding domains (or "sites"), and accordingly has binding specificities for two different target epitopes. These two epitopes may be epitopes of the same antigen or, as preferred in the present invention, of different antigens, such as the different antigens FLT3 and CD3.

A "bispecific ABP", may be an ABP that binds one antigen or epitope with one of two or more binding arms, defined by a first pair of heavy and light chain or of main and shorter/smaller chain, and binds a different antigen or epitope on a second arm, defined by a second pair of heavy and light chain or of main and smaller chain. Such an embodiment of a bispecific ABP has two distinct antigen binding arms, in both specificity and CDR sequences. Typically, a bispecific ABP is monovalent for each antigen it binds to, that is, it binds with only one arm to the respective antigen or epitope. However, bispecific antibodies can also be dimerized or multimerized, which is preferred in context of the present invention. For example, in the dimeric IgGsc format as described herein, the antibody may have two binding sites for each antigen (FIG. 1). A bispecific antibody may be a hybrid ABP, which may have a first binding region that is defined by a first light chain variable region and a first heavy chain variable region, and a second binding region that is defined by a second light chain variable region and a second heavy chain variable region. It is envisioned by the invention that one of these binding regions may be defined by a heavy/light chain pair. In the context of the present invention the bispecific ABP may have a first binding site, defined by variable regions of a main chain and a smaller chain, and a second, different binding site defined by a variable region of a scFv fragment that is included in the main chain of the ABP.

Methods of making a bispecific ABP are known in the art, e.g. chemical conjugation of two different monoclonal antibodies or for example, also chemical conjugation of two antibody fragments, for example, of two Fab fragments. Alternatively, bispecific ABPs are made by quadroma technology, that is by fusion of the hybridomas producing the parental antibodies. Because of the random assortment of H and L chains, a potential mixture of ten different antibody structures are produced of which only one has the desired binding specificity.

The bispecific ABP of the invention can act as a monoclonal antibody (mAb) with respect to each target. In some embodiments the antibody is chimeric, humanized or fully human. A bispecific ABP may for example be a bispecific tandem single chain Fv, a bispecific Fab2, or a bispecific diabody.

On the basis of the domains included in an ABP of the invention the bispecific ABP of the invention may comprise a Fab fragment, which may generally include a hinge region, a CH2 domain and a single chain Fv fragment. Such bispecific ABPs are termed "Fabsc"-ABPs and have been described for the first time in International patent application WO 2013/092001. More specifically, a "Fabsc" format ABP as used here typically refers to a bispecific ABP of the invention having a Fab fragment, which generally includes a hinge region, which is at the C-terminus of the Fab fragment linked to the N-terminus of a CH2 domain, of which the C-terminus is in turn linked to the N-terminus of a scFv fragment. Such a "Fabsc" does not or does not essentially comprise a CH3 domain. In this context, "not comprising" or "not essentially comprising" means that the ABP does not comprise a full length CH3 domain. It preferably means that the ABP comprises 10 or less, preferably 5 or less, preferably 3 or even less amino acids of the CH3 domain. An illustrative example for a Fabsc format ABP is shown in FIG. 1A, another illustrative example for a Fabsc format ABP is show in FIG. 12. In illustrative embodiments (cf. also FIG. 1A in this respect, an Fabsc ABP of the invention may comprise a CH2 domain that lacks is ability to dimerize by the disulphide bonds that are formed by the cysteine residue at sequence position 226 of the hinge region and/or the cysteine residue at sequence position 229 of one of the hinge domains, according to the Kabat numbering [EU-Index]. Thus, in these embodiments, the cysteine residues at sequence position 226 and/or sequence position 229 is either removed or replaced, for example, by a serine residue. In addition, or alternatively, an "Fabsc" ABP of the invention may also have an "Fc-attenuated" CH2 domain (that includes the hinge region). This "Fc-attenuation" is achieved by deleting and/or substituting (mutating) at least one of selected amino acid residues in the CH2 domain that are able to mediate binding to an Fc-receptor. In illustrative embodiments, the at least one amino acid residue of the hinge region or the CH2 domain that is able to mediate binding to Fc receptors and that is lacking or mutated, is selected from the group consisting of sequence position 228, 230, 231, 232, 233, 234, 235, 236, 237, 238, 265, 297, 327, and 330 (numbering of sequence positions according to the EU-index). In an illustrative example, such an Fc-attenuated ABP may contain at least one mutation selected from the group consisting of a deletion of amino acid 228, a deletion of amino acid 229, a deletion of amino acid 230, a deletion of amino acid 231, a deletion of amino acid 232, a deletion of amino acid 233, a substitution Glu233→Pro, a substitution Leu234→Val, a deletion of amino acid 234, a substitution Leu235→Ala, a deletion of amino acid 235, a deletion of amino acid 236, a deletion of amino acid 237, a deletion of amino acid 238, a substitution Asp265→Gly, a substitution Asn297→Gln, a substitution Ala327→Gln, and a substitution Ala330→Ser (numbering of sequence positions according to the EU-index, see in respect, for example, also FIG. 10 and FIG. 1P of International patent application WO 2013/092001). In the case of bispecific antibodies that activate T cells, e.g. against tumor cells, Fc-attenuation may be desired to prevent binding of the antibodies to Fc-receptor carrying cells which may lead to undesirable off-target activation of T cells.

In accordance with the publication of Coloma and Morrison (Nat Biotechnol 15:159-63, 1997), a bispecific ABP of the invention may also have a CH3 domain, generally arranged C-terminally of the CH2 domain. Such a molecule is also referred to herein as an "IgGsc" format ABP and means a bispecific ABP of the invention having a Fab fragment, which generally includes a hinge region, which is at the C-terminus of the Fab fragment typically linked to the N-terminus of a CH2 domain, of which the C-terminus is in turn typically linked to the N-terminus of a CH3 domain, of which the C-terminus is in turn typically linked to the N-terminus of a scFv fragment. An illustrative example of an IgGsc format ABP is shown in FIG. 1. Such bispecific ABP format is preferred in context of the present invention.

The antibody formats Fabsc and IgGsc have both in common that the N-terminal targeting part consists of "physiological" Fab- or Fab2 regions, respectively, thereby avoiding the use of single chain moieties in this part of the molecule. If these formats are to be used for target cell restricted T cell activation, attenuation of Fc receptor (FcR) binding may be employed (if wanted or required) to prevent FcR mediated activation. This can be achieved e.g. by introduction of defined and well-known mutations in the CH2 domain of the molecule as described in above and also in International patent application WO 2013/092001 and in Armour et al. Eur J Immunol 1999; 29:2613. Accordingly, also an IgGsc ABP of the invention may have a CH2 domain (including the hinge region) in which at least one amino acid residue of the hinge region or the CH2 domain that is able to mediate binding to Fc receptors is lacking or mutated. As explained above, this residue in the CH2 and hinge region, respectively, may be selected from the group consisting of sequence position 228, 230, 231, 232, 233, 234, 235, 236, 237, 238, 265, 297, 327, and 330 (numbering of sequence positions according to the EU-index). However, due to the presence of the CH3 domain in the IgGsc molecule, two individual molecules will (spontaneously) homodimerize via the CH3 domain to form a tetravalent molecule (see again FIG. 1B in this respect). Thus, it is not necessary to delete or mutate the cysteine residues at sequence position 226 and/or sequence position 229 of the hinge region. Thus, such a tetrameric IgGsc ABP of the invention may have a cysteine residue at sequence position 226 and/or at sequence position 229 of one of the respective hinge domain, in line with the Kabat numbering [EU-Index].

In line with the above disclosure of the bispecific ABPs that contain a set of CDR regions that mediate FLT3 binding and/or binding to leukemic cancer cells, the ABP of the present invention may comprise a second binding site that specifically binds to a receptor on an immune cell such as a T cell or an NK cells. This receptor present on the immune cell may be a receptor that is capable of activating the immune cell or of stimulating an immune response of the immune cell. The evoked immune response may preferably be a cytotoxic immune response. Such a suitable receptor may, for example, be CD3, the antigen specific T cell receptor (TCR), CD28, CD16, NKG2D, Ox40, 4-1 BB, CD2, CD5, programmed cell death protein 1 (PD-1) and CD95. Particularly preferred is an ABP in which the second binding site binds to CD3, TCR or CD16. Most preferred is an ABP, in which the second binding site specifically binds to CD3. One preferred ABP comprises a second binding site that corresponds to the antigen binding site of the anti-CD3 antibody OKT3. The amino acid sequence of the variable domain of the heavy chain and of the variable domain of the light chain of the antibody OKT3 are, for example, also described in Arakawa et al J. Biochem. 120, 657-662 (1996) and International Patent Application WO 2015/158868 (see SEQ ID NOS: 17 and 18 in the Sequence Listings of WO 2015/158868). Another preferred ABP comprises a second binding site that corresponds to the antigen binding site of the anti-CD3 antibody UCHT1. The VH and VL sequences of a humanized UCHT1 antibody are described in International Patent Application WO 2013/092001. Other examples of CD3 binding ABPs that can be used in the present invention include the ABPs described in European Patent 2

155 783 B1 or European Patent EP 2 155 788 B1 that are capable of binding to an epitope of human and *Callithrix jacchus, Saguinus oedipus* or *Saimiri sciureus* CD3ε chain.

Accordingly, the bispecific ABP of the invention may be a bispecific ABP such as a IgGsc-molecule that comprises a Fab fragment and a scFv fragment as described herein. In this molecule the first binding site may bind to FLT3 and may be comprised in a Fab (or a bivalent FLT3 F(ab)2 in context of the IgGsc format) fragment as described herein and the second binding site (that may bind to an immune receptor) may be comprised in a scFv fragment, such as an scFv binding specifically to CD3. Alternatively, the first binding site that binds to FLT3 is comprised in a single chain Fv fragment and the second binding site (that may bind to CD3) is comprised in a Fab fragment.

In some embodiments, the bispecific ABP of the invention does not by itself activate the immune cell, e.g. the T cell, upon binding, such as binding to CD3. Instead, only when both binding sites, e.g. the FLT3-specific binding sited and the CD3 specific binding site are bound to the receptor on the T cell and to FLT3 on the target cancer cell, the former may cross-link the activating receptor, triggering the effector cells to kill the specific target cell. Standard functional assays to evaluate the target cell-killing capability by lymphocytes in the presence and absence of an bispecific ABP of the invention can be set up to assess and/or screen for the ability of the ABP to activate the receptor to which it binds.

In some embodiments of the invention the bispecific ABP comprises as second antigen binding domain a scFv of and anti-CD3 antibody, such as UCHT1 or variants thereof, which are for example disclosed in the present application in SEQ ID NO: 14, and 25 to 27.

It is noted in this context that it is within the scope of the invention that an ABP may comprise one or more mutated amino acid residues. The terms "mutated", "mutant" and "mutation" in reference to a nucleic acid or a polypeptide refers to the exchange, deletion, or insertion of one or more nucleotides or amino acids, respectively, compared to the "naturally" or "parent" (if a reference is provided) occurring nucleic acid or polypeptide, i.e. to a reference sequence that can be taken to define the wild-type. For example, the variable domains of the ABPs of the invention as obtained by extensive mutational alteration of the parent 4G8 molecule and as described herein may be taken as a parent sequence.

It is understood in this regard that the term "position", when used in accordance with the present invention, means the position of an amino acid within an amino acid sequence depicted herein. This position may be indicated relative to a resembling native sequence, e.g. a sequence of a naturally occurring IgG domain or chain. The term "corresponding" as used herein also includes that a position is not necessarily, or not only, determined by the number of the preceding nucleotides/amino acids. Thus, the position of a given amino acid in accordance with the present invention which may be substituted may vary due to deletion or addition of amino acids elsewhere in the antibody chain.

Thus, under a "corresponding position" in accordance with the present invention it is to be understood that amino acids may differ in the indicated number but may still have similar neighbouring amino acids. Said amino acids which may be exchanged, deleted or added are also encompassed by the term "corresponding position". In order to determine whether an amino acid residue in a given amino acid sequence corresponds to a certain position in the amino acid sequence of a naturally occurring immunoglobulin domain or chain, the skilled person can use means and methods well-known in the art, e.g., alignments, either manually or by using computer programs such as BLAST2.0, which stands for Basic Local Alignment Search Tool or ClustalW or any other suitable program which is suitable to generate sequence alignments.

In some embodiments a substitution (or replacement) is a conservative substitution. Conservative substitutions are generally the following substitutions, listed according to the amino acid to be mutated, each followed by one or more replacement(s) that can be taken to be conservative: Ala→Gly, Ser, Val; Arg→Lys; Asn→Gln, His; Asp→Glu; Cys→Ser; Gln→Asn; Glu→Asp; Gly→Ala; His→Arg, Asn, Gln; Ile→Leu, Val; Leu→Ile, Val; Lys→Arg, Gln, Glu; Met→Leu, Tyr, Ile; Phe→Met, Leu, Tyr; Ser→Thr; Thr→Ser; Trp→Tyr; Tyr→Trp, Phe; Val→Ile, Leu. Other substitutions are also permissible and can be determined empirically or in accord with other known conservative or non-conservative substitutions. As a further orientation, the following eight groups each contain amino acids that can typically be taken to define conservative substitutions for one another:

Alanine (Ala), Glycine (Gly);
Aspartic acid (Asp), Glutamic acid (Glu);
Asparagine (Asn), Glutamine (Gln);
Arginine (Arg), Lysine (Lys);
Isoleucine (Ile), Leucine (Leu), Methionine (Met), Valine (Val);
Phenylalanine (Phe), Tyrosine (Tyr), Tryptophan (Trp);
Serine (Ser), Threonine (Thr); and
Cysteine (Cys), Methionine (Met)

If such substitutions result in a change in biological activity, then more substantial changes, such as the following, or as further described below in reference to amino acid classes, may be introduced and the products screened for a desired characteristic. Examples of such more substantial changes are: Ala→Leu, Ile; Arg→Gln; Asn→Asp, Lys, Arg, His; Asp→Asn; Cys→Ala; Gln→Glu; Glu→Gln; His→Lys; Ile→Met, Ala, Phe; Leu→Ala, Met, Norleucine; Lys→Asn; Met→Phe; Phe→Val, Ile, Ala; Trp→Phe; Tyr→Thr, Ser; Val→Met, Phe, Ala.

In some embodiments an ABP according to the invention includes one or more amino acid residues, including two, three, four, five, six, seven, eight, nine, ten, eleven, twelve, thirteen, fourteen, fifteen, sixteen, seventeen or eighteen amino acid residues, that are mutated to prevent dimerization via cysteine residues or to modulate Fc-function (see above). In some of these embodiments one or more amino acid residue(s) of the CH2 domain and/or of the hinge region that is able to mediate binding to Fc receptors are mutated. If present, the one or more amino acid residue(s) able to mediate binding to Fc receptors may be an amino acid residue that is able to activate antibody dependent cellular cytotoxicity (ADCC) or complement-mediated cytotoxicity (CDC). In some embodiments a respective amino acid residue capable of mediating binding to Fc receptors is substituted by another amino acid, generally when comparing the sequence to the sequence of a corresponding naturally occurring domain in an immunoglobulin, such as an IgG. In some embodiments such an amino acid residue capable of mediating binding to Fc receptors is deleted, generally relative to the sequence of a corresponding naturally occurring domain in an immunoglobulin, such as an IgG.

In some embodiments the one or more mutated, e.g. substituted or deleted, amino acid residues is/are an amino acid located at one of the positions 226, 228, 229, 230, 231, 232, 233, 234, 235, 236, 237, 238, 265, 297, 327, and 330.

Again, the numbering of amino acids used corresponds to the sequence positions according to the Kabat numbering [EU-Index]. A corresponding deletion of an amino acid may for example be a deletion of amino acid 228, generally a proline in IgG, a deletion of amino acid 229, generally a cysteine in IgG, a deletion of amino acid 230, generally a proline in IgG, a deletion of amino acid 231, generally an alanine in IgG, a deletion of amino acid 232, generally a proline in IgG, a deletion of amino acid 233, generally a glutamic acid in IgG, a deletion of amino acid 234, generally a leucine in IgG, a deletion of amino acid 235, generally a leucine in IgG, a deletion of amino acid 236, generally a glycine in IgG, a deletion of amino acid 237, generally a glycine in IgG, a deletion of amino acid 238, generally a proline in IgG and a deletion of amino acid 265, generally an aspartic acid in IgG. A corresponding substitution of an amino acid may for example be a substitution of amino acid 226, generally a cysteine in IgG, a substitution of amino acid 228, generally a proline in IgG, a substitution of amino acid 229, generally a cysteine in IgG, a substitution of amino acid 230, generally a proline in IgG, a substitution of amino acid 231, generally an alanine in IgG, a substitution of amino acid 232, generally a proline in IgG, a substitution of amino acid 233, generally a glutamic acid in IgG, a substitution of amino acid 234, generally a leucine in IgG, a substitution of amino acid 235, generally a leucine in IgG, a substitution of amino acid 265, generally an aspartic acid in IgG, a substitution of amino acid 297, generally an asparagine in IgG, a substitution of amino acid 327, generally an alanine in IgG, and a substitution of amino acid 330, generally an alanine in IgG. A respective substitution may be one of substitution Cys226→Ser, substitution Cys229→Ser, substitution Glu233→Pro, substitution Leu234→Val, substitution Leu235→Ala, substitution Asp265→Gly, substitution Asn297→Gln, substitution Ala327→Gln, substitution Ala327→Gly, and substitution Ala330→Ser. As can be taken from the above, in some embodiments one or two of the cysteine residues at positions 226 and 229 in the hinge region are being substituted for another amino acid, for instance substituted for a serine residue. Thereby the formation of a disulphide bond with another main chain can be prevented. Further, and as also explained below, deleting and/or substituting (mutating) selected amino acid residues in the CH2 domain that is able to mediate binding to Fc-receptors can cause an ABP of the invention to have less or no activity in terms of antibody-dependent cell-mediated cytotoxicity and fixation of complement.

Another type of amino acid variant of an antibody alters the original glycosylation pattern (if any) of the ABP. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

In the context of the present invention, in some embodiments the portion of the main chain of the ABP of the invention, which represents the Fc region of an immunoglobulin, is typically inert, or at least essentially of low influence, with regard to binding to Fc receptors. As said, this is achieved by deleting and/or substituting (mutating) at least one of selected amino acid residues in the CH2 domain that are able to mediate binding to an Fc-receptor. Such molecules are also referred to herein as "Fc-attenuated" ABPs or "Fcko" ABPs. The portion of an antibody chain according to the invention that can be taken to represent a portion of an Fc fragment, i.e. the CH2 domain, and, where present, the CH3 domain, thus might define a "scaffold" without providing a particular biological function such as an effector function, for example. However, it has been found in the present invention, that this scaffold may provide significant advantages in terms of purification, production efficiency and/or stability of the ABPs of the invention compared to known ABPs.

In some embodiments the recognition, and accordingly binding, of this Fc-corresponding portion to a given Fc receptor is of about 2-fold, about 5-fold, about 8-fold, about 10-fold, about 12-fold, about 15-fold, about 20-fold or lower than the Fc region of a naturally occurring immunoglobulin. In some embodiments this Fc-corresponding portion is entirely void of its ability of binding to Fc receptors. The binding of an antibody to Fc receptors, including determining a dissociation constant, can easily be determined by the skilled artisan using standard techniques such as surface plasmon resonance, e.g. using a Biacore™ measurement. Any other method of measuring biomolecular binding may likewise be used, which may for instance rely on spectroscopical, photochemical, photometric or radiological means. Examples for the corresponding detection methods are fluorescence correlation spectroscopy, photochemical cross-linking and the use of photoactive or radioactive labels respectively. Some of these methods may include additional separation techniques such as electrophoresis or HPLC.

Where required, a substitution or deletion of amino acid residues, as explained above, may be carried out to this effect. Suitable mutations can be taken from Armour et al. (Eur. J. Immunol. [1999] 29, 2613-2624), for example. Further suitable positions for mutations to a sequence of an antibody chain can be taken from the crystal structure data published on the complex between FcγRIII and the human IgG1 Fc fragment (Sondermann et al., Nature [2000]406, 267-273). In addition to measuring the binding affinity as described above in order to assess the level of "Fc attenuation" or loss of binding affinity, it is also possible to functionally assess the (lack of the) ability to mediate binding to an Fc-receptor. In the case of ABPs which bind CD3 as one target, it is for example possible to assess the binding through the mitogenity of such CD3 binding ABPs on cells. The mitogenity is mediated by binding of CD3 antibodies to the Fc-receptors on accessory cells, such as monocytes. If an ABP of the invention that has one binding site for CD3 does not show any mitogenic effect whereas the parent monoclonal anti-CD3 antibody that has a functional Fc part induces strong mitosis in T cells, it is clear that, due to the lack of mitosis, the ABP of the invention lacks the ability for Fc binding and can thus be considered as a "Fc knock-out" molecule. Illustrative examples of a method of assessing anti-CD3 mediated mitogenity have been described by Davis, Vida & Lipsky (J. Immunol (1986) 137, 3758), and by Ceuppens, J L, & van Vaeck, F, (see J. Immunol. (1987) 139, 4067, or Cell. Immunol. (1989) 118, 136). Further illustrative suitable examples of an assay for assessing mitogenity of an antibody have been described by Rosenthal-Allieri et al. (Rosenthal-Allieri M A, Ticcioni M, Deckert M, Breittmeyer J P, Rochet N, Rouleaux M, and Senik A, Bernerd A, Cell Immunol. 1995 163(1):88-95) and Grosse-Hovest et al. (Grosse-Hovest L, Hartlapp I, Marwan W, Brem G, Rammensee H-G, and Jung G, Eur J Immunol. [2003] May; 33(5):1334-1340). In addition, the lack of Fc binding can be assessed by the ability of an ABP of the invention to mediate one or more of the well-known effector functions of the Fc part.

As noted above, substitutions or deletions of cysteine residues may be carried out in order to introduce or to remove one or more disulfide bonds, including introducing or removing a potential or a previously existing disulfide bond. Thereby linkage between a main chain and a chain of lower weight/shorter length of an ABP according to the invention may be controlled including established, strengthened or abolished. By introducing or removing one or more cysteine residues a disulfide bridge may be introduced or removed. As an illustrative example, a tetrameric ABP according to the invention generally has one or more disulfide bonds that link two dimeric ABPs. One such disulfide bond is typically defined by a cysteine in the main chain of a first dimeric ABP and a cysteine in the hinge region of a second dimeric ABP. In this regard, in some embodiments an antibody according to the invention may include an amino acid substitution of a native cysteine residue at positions 226 and/or 229, relative to the sequence of a human IgG immunoglobulin according to the Kabat numbering [EU-Index], by another amino acid residue.

Substitutions or deletions of amino acid residues such as arginine, asparagine, serine, threonine or tyrosine residues may also be carried out to modify the glycosylation pattern of an antibody. As an illustrative example, an IgG molecule has a single N-linked biantennary carbohydrate at Asn297 of the CH2 domain. For IgG from either serum or produced ex vivo in hybridomas or engineered cells, the IgG are heterogeneous with respect to the Asn297 linked carbohydrate. For human IgG, the core oligosaccharide typically consists of GlcNAc2Man3GlcNAc, with differing numbers of outer residues.

As indicated, besides binding of antigens/epitopes, an immunoglobulin is known to have further "effector functions", biological activities attributable to the Fc region (a native sequence Fc region or amino acid sequence variant Fc region) of an immunoglobulin, and vary with the immunoglobulin isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptors); and B cell activation. Exerting effector functions of an antibody generally involves recruiting effector cells. Several immunoglobulin effector functions are mediated by Fc receptors (FcRs), which bind the Fc region of an antibody. FcRs are defined by their specificity for immunoglobulin isotypes; Fc receptors for IgG antibodies are referred to as FcγR, for IgE as FcεR, for IgA as FcαR and so on. Any of these effector functions (or the loss of such effector functions) such a CDC or ADCC can be used in order to evaluate whether an ABP of the invention lacks the ability of Fc binding.

In this context, it is noted that the term "Fc receptor" or "FcR" defines a receptor, generally a protein that is capable of binding to the Fc region of an antibody. Fc receptors are found on the surface of certain cells of the immune system of an organism, for example natural killer cells, macrophages, neutrophils, and mast cells. In vivo Fc receptors bind to immunoglobulins that are immobilized on infected cells or present on invading pathogens. Their activity stimulates phagocytic or cytotoxic cells to destroy microbes, or infected cells by antibody-mediated phagocytosis or antibody-dependent cell-mediated cytotoxicity. Some viruses such as flaviviruses use Fc receptors to help them infect cells, by a mechanism known as antibody-dependent enhancement of infection. FcRs have been reviewed in Ravetch and Kinet, Annu. Rev. Immunol. 9: 457-92 (1991); Capel et al., Immunomethods 4: 25-34 (1994); and de Haas et al., J. Lab. Clin. Med. 126: 330-41 (1995).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202: 163 (1997) may be performed.

The term "complement system" is used in the art to refer a number of small proteins—called complement factors—found in blood, generally circulating as inactive precursors (pro-proteins). The term refers to the ability of this inalterable and not adaptable system to "complement" the capability of antibodies and phagocytic cells to clear pathogens such as bacteria, as well as antigen-antibody complexes, from an organism. An example of complement factors is the complex C1, which includes C1q and two serine protases, C1r and C1s. The complex C1 is a component of the CDC pathway. C1q is a hexavalent molecule with a molecular weight of approximately 460,000 and a structure likened to a bouquet of tulips in which six collagenous "stalks" are connected to six globular head regions. To activate the complement cascade, C1q has to bind to at least two molecules of IgG1, IgG2 or IgG3.

"Antibody-dependent cellular cytotoxicity" or ADCC refers to a form of cytotoxicity in which immunoglobulin molecules, bound onto Fc receptors (FcRs), present on certain cytotoxic cells—such as natural killer (NK) cells, neutrophils and macrophages—enable these cytotoxic effector cells to bind specifically to an antigen-bearing target cell and to subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9: 457-92 (1991). To assess ADCC activity of a molecule of interest, an in vitro ADCC assay, such as described in U.S. Pat. No. 5,500,362 or 5,821,337 may be carried out. Useful effector cells for such assays include, but are not limited to, peripheral blood mononuclear cells (PBMC) and natural killer (NK) cells. In some embodiments ADCC activity of the molecule of interest may be assessed in vivo, e.g., in an animal model such as disclosed in Clynes et al., PNAS USA 95: 652-656 (1998).

An ABP of the invention may be produced using any known and well-established expression system and recombinant cell culturing technology, for example, by expression in bacterial hosts (prokaryotic systems), or eukaryotic systems such as yeasts, fungi, insect cells or mammalian cells. For example, an ABP of the invention when being used in the "IgGsc" format, the ABP can (of course) be produced as described by Coloma and Morrison (Nat Biotechnol 15:159-63, 1997) or as described in the Example Section of the present application. Likewise, an ABP of the invention employed in the "Fabsc" format can be produced as described in International patent application WO 2013/092001 or as described here in the Example Section. An ABP of the present invention may also be produced in transgenic organisms such as a goat, a plant or a XENOMOUSE transgenic mouse, an engineered mouse strain that has large fragments of the human immunoglobulin loci and is deficient in mouse antibody production. An antibody may also be produced by chemical synthesis.

For production of a recombinant ABP of the invention, typically a polynucleotide encoding the antibody is isolated and inserted into a replicable vector such as a plasmid for further cloning (amplification) or expression. An illustrative example of a suitable expression system is a glutamate synthetase system (such as sold by Lonza Biologics), with the host cell being for instance CHO or NSo. A polynucleotide encoding the antibody is readily isolated and sequenced using conventional procedures. Vectors that may be used include plasmid, virus, phage, transposons, minichromsomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotides encoding the light and heavy chains may be inserted into separate vectors and transfected into the same host cell or, if desired both the heavy chain and light chain can be inserted into the same vector for transfection into the host cell. Both chains can, for example, be arranged, under the control of a dicistronic operon and expressed to result in the functional and correctly folded ABP as described in Skerra, A. (1994) Use of the tetracycline promoter for the tightly regulated production of a murine antibody fragment in *Escherichia coli*, Gene 151, 131-135, or Skerra, A. (1994) A general vector, pASK84, for cloning, bacterial production, and single-step purification of antibody Fab fragments, Gene 141, 79-8. Thus, according to one aspect of the present invention there is provided a process of constructing a vector encoding the light and/or heavy chains of an antibody or antigen binding fragment thereof of the invention, which method includes inserting into a vector, a polynucleotide encoding either a light chain and/or heavy chain of an ABP of the invention.

When using recombinant techniques, the ABP can be produced intracellularly, in the periplasmic space, or directly secreted into the medium (cf. also Skerra 1994, supra). If the antibody is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E coli*. The antibody can also be produced in any oxidizing environment. Such an oxidizing environment may be provided by the periplasm of Gram-negative bacteria such as *E. coli*, in the extracellular milieu of Gram-positive bacteria or in the lumen of the endoplasmatic reticulum of eukaryotic cells (including animal cells such as insect or mammalian cells) and usually favors the formation of structural disulfide bonds. It is, however, also possible to produce an ABP of the invention in the cytosol of a host cell such as *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi M, Seifert C, Hunte C. (2002) "High level production of functional antibody Fab fragments in an oxidizing bacterial cytoplasm." J. Mol. Biol. 315, 1-8).

The ABP produced by the cells can be purified using any conventional purification technology, for example, hydroxylapatite chromatography, gel electrophoresis, dialysis, and affinity chromatography, with affinity chromatography being one preferred purification technique. ABPs may be purified via affinity purification with proteins/ligands that specifically and reversibly bind constant domains such as the CH1 or the CL domains. Examples of such proteins are immunoglobulin-binding bacterial proteins such as Protein A, Protein G, Protein A/G or Protein L, wherein Protein L binding is restricted to ABPs that contain kappa light chains. An alternative method for purification of antibodies with κ-light chains is the use of bead coupled anti kappa antibodies (KappaSelect). The suitability of protein A as an affinity ligand depends on the species and isotype of any immunoglobulin Fc domain that is present in the antibody. Protein A can be used to purify antibodies (Lindmark et al., J. Immunol. Meth. 62: 1-13 (1983)). Protein G is recommended for all mouse isotypes and for human gamma3 (Guss et al., EMBO J. 5: 15671575 (1986)). The choice of the purification method that is used for a particular ABP of the invention is within the knowledge of the person of average skill in the art.

It is also possible to equip one of the chains of the ABP of the invention with one or more affinity tags. Affinity tags such as the Strep-Tag® or Strep-Tag® II (Schmidt, T. G. M. et al. (1996) J. Mol. Biol. 255, 753-766), the myc-tag, the FLAG™-tag, the His6-tag or the HA-tag allow easy detection and also simple purification of the recombinant ABP.

Turning now to nucleic acids of the invention, a nucleic acid molecule encoding one or more chains of an antibody according to the invention may be any nucleic acid in any possible configuration, such as single stranded, double stranded or a combination thereof. Nucleic acids include for instance DNA molecules, RNA molecules, analogues of the DNA or RNA generated using nucleotide analogues or using nucleic acid chemistry, locked nucleic acid molecules (LNA), and protein nucleic acids molecules (PNA). DNA or RNA may be of genomic or synthetic origin and may be single or double stranded. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label.

In some embodiments a nucleic acid sequence encoding a chain, such as a main chain and/or a smaller chain of an antibody according to the invention is included in a vector such as a plasmid. Where a substitution or deletion is to be included in an antibody chain, when compared to a naturally occurring domain or region of an antibody, the coding sequence of the respective native domain/region, e.g. included in the sequence of an immunoglobulin, can be used as a starting point for the mutagenesis. For the mutagenesis of selected amino acid positions, the person skilled in the art has at his disposal the various established standard methods for site-directed mutagenesis. A commonly used technique is the introduction of mutations by means of PCR (polymerase chain reaction) using mixtures of synthetic oligonucleotides, which bear a degenerate base composition at the desired sequence positions. For example, use of the codon NNK or NNS (wherein N=adenine, guanine or cytosine or thymine; K=guanine or thymine; S=adenine or cytosine) allows incorporation of all 20 amino acids plus the amber stop codon during mutagenesis, whereas the codon VVS limits the number of possibly incorporated amino acids to 12, since it excludes the amino acids Cys, Ile, Leu, Met, Phe, Trp, Tyr, Val from being incorporated into the selected position of the polypeptide sequence; use of the codon NMS (wherein M=adenine or cytosine), for example, restricts the number of possible amino acids to 11 at a selected sequence position since it excludes the amino acids Arg, Cys, Gly, Ile, Leu, Met, Phe, Trp, Val from being incorporated at a selected sequence position. In this respect it is noted that codons for other amino acids (than the regular 20 naturally occurring amino acids) such as selenocystein or pyrrolysine can also be incorporated into a nucleic acid of an ABP. It is also possible, as described by Wang, L., et al. (2001) Science 292, 498-500, or Wang, L., and Schultz, P. G. (2002) Chem. Comm. 1, 1-11, to use "artificial" codons such as UAG which are usually recognized as stop codons in order to insert other unusual amino acids, for example o-methyl-L-tyrosine or p-aminophenylalanine.

The use of nucleotide building blocks with reduced base pair specificity, as for example inosine, 8-oxo-2'deoxyguanosine or 6(2-deoxy-β-D-ribofuranosyl)-3,4-dihydro-8H-pyrimin-do-1,2-oxazine-7-one (Zaccolo et al. (1996) J. Mol. Biol. 255, 589-603), is another option for the introduction of mutations into a chosen sequence segment. A further possibility is the so-called triplet-mutagenesis. This method uses mixtures of different nucleotide triplets, each of which codes for one amino acid, for incorporation into the coding sequence (Virnekäs B, et al., 1994 Nucleic Acids Res 22, 5600-5607).

A nucleic acid molecule encoding a chain, such as a main chain and/or a smaller chain of an antibody according to the invention can be expressed using any suitable expression system, for example in a suitable host cell or in a cell-free system. The obtained ABP may be enriched by means of selection and/or isolation. Preferably the nucleic acids of the invention are provided in context of genetic constructs such as vectors/plasmids.

Further provided is a system of nucleic acids, or constructs comprising such nucleic acid of the invention, wherein the system of the invention comprises at least two nucleic acids of the invention each encoding one monomer of an ABP of the invention, for example one nucleic acid encoding a heavy chain sequence, and a second nucleic acid encoding a light chain sequence.

In some embodiments, the polypeptides of the ABP of the invention can be encoded by nucleic acids for expression in vivo or in vitro. Thus, in some embodiments, an isolated nucleic acid encoding an ABP of the invention is provided. In some embodiments, the nucleic acid encodes one part or monomer of an ABP of the invention (for example one of two (heavy and light) chains of an antibody), and/or another nucleic acid encodes another part or monomer of an ABP of the invention (for example the other of two chains of an antibody). Such nucleic acids may be provided in combination or as a system together. In some embodiments, the nucleic acid encodes two or more ABP polypeptide chains, for example, at least 2 antibody chains. Nucleic acids encoding multiple ABP chains can include nucleic acid cleavage sites between at least two chain sequences, can encode transcription or translation start site between two or more chains sequences, and/or can encode proteolytic target sites between two or more ABP chains.

Yet, one further aspect of the invention provides a vector (such as an expression vector) that comprises a nucleic acid encoding an ABP as disclosed herein, or a part or monomer of an ABP. For example, in some embodiments, where the ABP is a multimeric protein, the nucleic acid encodes only a single polypeptide chain of the antigen construct. Therefore, to express such an antigen binding construct, an expression vector of the invention may contain two or more nucleic acids that each encode a separate part or monomer of an ABP, which in combination would express an entire ABP. Analogously, an expression vector of the invention that comprises a nucleic acid that encodes only part or monomer of an antigen binding construct, may be used in combination with other separate expression vectors of the invention that each encode a separate part or monomer of an ABP. In other embodiments the nucleic acid encodes multiple polypeptide chains of the ABP of the invention. In some embodiments, the expression vector includes pcDNA3.1™/myc-His (−) Version A vector for mammalian expression (Invitrogen, Inc.) or a variant thereof. The pcDNA3.1 expression vector features a CMV promoter for mammalian expression and both mammalian (Neomycin) and bacterial (Ampicillin) selection markers. In some embodiments, the expression vector includes a plasmid. In some embodiments, the vector includes a viral vector, for example a retroviral or adenoviral vector. In embodiments, the vector includes a cosmid, YAC, or BAC.

In another related aspect, the invention relates to a cell (such as a host cell and/or a recombinant host cell) comprising one or more nucleic acid of the invention. Preferably, such cell is capable of expressing the ABP (or component thereof) encoded by said nucleic acids. For example, if an ABP of the invention comprises two separate polypeptide chains (e.g. a heavy and light chain of an IgG), then the cell of the invention may comprise a first nucleic acid that encodes (and can express) the heavy chain of such ABP as well as a second nucleic acid that encodes (and can express) the light chain of such ABP; alternatively, the cell may comprise a single nucleic acid that encodes both chains of such ABP. In these ways, such a cell of the invention would be capable of expressing a functional ABP of the invention. A (host) cell of invention may be one of the mammalian, prokaryotic or eukaryotic host cells as described elsewhere herein, in particularly where the cell is a Chinese hamster ovary (CHO) cell.

In certain embodiments of such aspect, the (host) cell is a human cell; in particular it may be a human cell that has been sampled from a specific individual (e.g. an autologous human cell). In such embodiments, such human cell can be propagated and/or manipulated in-vitro so as to introduce a nucleic acid of the present invention. The utility of a manipulated human cell from a specific individual can be to produce an ABP of the invention, including to reintroduce a population of such manipulated human cells into a human subject, such as for use in therapy. In certain of such uses, the manipulated human cell may be introduced into the same human individual from which it was first sampled; for example, as an autologous human cell.

The human cell that is subject to such manipulation can be of any germ cell or somatic cell type in the body. For example, the donor cell can be a germ cell or a somatic cell selected from the group consisting of fibroblasts, B cells, T cells, dendritic cells, keratinocytes, adipose cells, epithelial cells, epidermal cells, chondrocytes, cumulus cells, neural cells, glial cells, astrocytes, cardiac cells, oesophageal cells, muscle cells, melanocytes, hematopoietic cells, macrophages, monocytes, and mononuclear cells. The donor cell can be obtained from any organ or tissue in the body; for example, it can be a cell from an organ selected from the group consisting of liver, stomach, intestines, lung, pancreas, cornea, skin, gallbladder, ovary, testes, kidneys, heart, bladder, and urethra.

The invention also provides a pharmaceutical composition that includes an ABP of the invention and, optionally a pharmaceutically acceptable excipient.

The ABP according to the invention can be administered via any parenteral or non-parenteral (enteral) route that is therapeutically effective for proteinaceous drugs. Parenteral application methods include, for example, intracutaneous, subcutaneous, intramuscular, intratracheal, intranasal, intravitreal or intravenous injection and infusion techniques, e.g. in the form of injection solutions, infusion solutions or tinctures, as well as aerosol installation and inhalation, e.g. in the form of aerosol mixtures, sprays or powders. An overview about pulmonary drug delivery, i.e. either via inhalation of aerosols (which can also be used in intranasal administration) or intracheal instillation is given by J. S. Patton et al. The lungs as a portal of entry for systemic drug delivery. Proc. Amer. Thoracic Soc. 2004 Vol. 1 pages 338-344, for example). Non-parenteral delivery modes are, for instance, orally, e.g. in the form of pills, tablets, capsules, solutions or suspensions, or rectally, e.g. in the form of suppositories. ABPs of the invention can be administered systemically or topically in formulations containing conventional non-toxic pharmaceutically acceptable excipients or carriers, additives and vehicles as desired.

In one embodiment of the present invention the pharmaceutical is administered parenterally to a mammal, and in particular to humans. Corresponding administration methods include, but are not limited to, for example, intracutaneous, subcutaneous, intramuscular, intratracheal or intravenous injection and infusion techniques, e.g. in the form of injection solutions, infusion solutions or tinctures as well as aerosol installation and inhalation, e.g. in the form of aerosol mixtures, sprays or powders. A combination of intravenous and subcutaneous infusion and/or injection might be most convenient in case of compounds with a relatively short serum half-life. The pharmaceutical composition may be an aqueous solution, an oil-in water emulsion or a water-in-oil emulsion.

In this regard it is noted that transdermal delivery technologies, e.g. iontophoresis, sonophoresis or microneedle-enhanced delivery, as described in Meidan V M and Michniak B B 2004 Am. J. Ther. 11(4): 312-316, can also be used for transdermal delivery of an ABP described herein. Non-parenteral delivery modes are, for instance, oral, e.g. in the form of pills, tablets, capsules, solutions or suspensions, or rectal administration, e.g. in the form of suppositories. The ABPs of the invention can be administered systemically or topically in formulations containing a variety of conventional non-toxic pharmaceutically acceptable excipients or carriers, additives, and vehicles.

The dosage of the ABP applied may vary within wide limits to achieve the desired preventive effect or therapeutic response. It will, for instance, depend on the affinity of the ABP for a chosen target as well as on the half-life of the complex between the ABP and the ligand in vivo. Further, the optimal dosage will depend on the biodistribution of the ABP or a conjugate thereof, the mode of administration, the severity of the disease/disorder being treated as well as the medical condition of the patient. For example, when used in an ointment for topical applications, a high concentration of the ABP can be used. However, if wanted, the ABP may also be given in a sustained release formulation, for example liposomal dispersions or hydrogel-based polymer microspheres, like PolyActive™ or OctoDEX™ (cf. Bos et al., Business Briefing: Pharmatech 2003: 1-6). Other sustained release formulations available are for example PLGA based polymers (PR pharmaceuticals), PLA-PEG based hydrogels (Medincell) and PEA based polymers (Medivas).

Accordingly, the ABPs of the present invention can be formulated into compositions using pharmaceutically acceptable ingredients as well as established methods of preparation (Gennaro, A. L. and Gennaro, A. R. (2000) Remington: The Science and Practice of Pharmacy, 20th Ed., Lippincott Williams & Wilkins, Philadelphia, Pa.). To prepare the pharmaceutical compositions, pharmaceutically inert inorganic or organic excipients can be used. To prepare e.g. pills, powders, gelatin capsules or suppositories, for example, lactose, talc, stearic acid and its salts, fats, waxes, solid or liquid polyols, natural and hardened oils can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The pharmaceutical composition may also contain additives, such as, for example, fillers, binders, wetting agents, glidants, stabilizers, preservatives, emulsifiers, and furthermore solvents or solubilizers or agents for achieving a depot effect. The latter is that fusion proteins may be incorporated into slow or sustained release or targeted delivery systems, such as liposomes and microcapsules.

The formulations can be sterilized by numerous means, including filtration through a bacteria-retaining filter, or by incorporating sterilizing agents in the form of sterile solid compositions which can be dissolved or dispersed in sterile water or other sterile medium just prior to use.

The ABP may be suitable for and may be used in the treatment or prevention of a disease. Accordingly, in some embodiments, an ABP according to the invention may be used in a method of treating and/or preventing a medical condition such as a disorder or disease. Similarly, the ABP of the present invention can be used in the treatment of a disease. The disease to be treated or prevented may be a proliferative disease. Such a proliferative disease may preferably be tumor or cancer. Due to the ability of the ABP of the invention to bind FLT3, this ABP can be used to treat cancer that consists of cells that express FLT3, both wild-type or mutated FLT3. With respect to the inventive treatments, the cancer can be any cancer, including any of acute lymphocytic cancer, acute myeloid leukemia (AMI), alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer., larynx cancer, leukemia, liquid tumors, liver cancer, lung cancer (e.g., non-small cell lung carcinoma and long adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkiht's lymphoma, ovarian cancer, pancreatic cancer, peritoneum, omentum, and mesentery cancer, pharynx cancer, prostate cancer, rectal cancer, renal cancer, skin cancer, small intestinal cancer, soft tissue cancer, solid tumors, synovial sarcoma, gastric cancer, testicular cancer, thyroid cancer, and ureter cancer. Preferably, the cancer is characterized by the expression of FLT3. Most preferably the cancer is a FLT3 positive leukemia, such as AML or ALL.

The subject to be treated with the fusion protein can be a human or non-human animal. Such an animal is preferably a mammal, for instance a human, pig, cattle, rabbit, mouse, rat, primate, goat, sheep, chicken, or horse, most preferably a human.

The ABP of the invention may also be used in the diagnosis of a disease, such as a disease as described herein. The ABP may for this purpose be labeled with a suitable detectable signaling label. Such a labeled ABP may permit detection or quantitation of FLT3 level or cancer such as leukemia, or any of the above-mentioned cancers, or subject. When designated for in vivo use, said detectable signaling label is preferably detectable in vivo.

The labelled ABP may be used in an immune-imaging technique. The detectable signaling label may then be selected, for instance, based on the immuno-imaging technique employed for the diagnosis, for example, gamma-emitting radionuclide (or gamma-emitter) in case of gamma camera-imaging technique/SPECT, metal or positron emitter in case of MRI or PET imaging techniques, respectively. In this regard, one or more detectable signaling labels of the disclosure include gamma camera-imageable agents, PET-imageable agents and MRI-imageable agents, such as, radionuclides, fluorescers, fluorogens, chromophores, chromogens, phosphorescers, chemiluminescers and bioluminescers.

A suitable detectable signaling label may be a radionuclide. Said radionuclide may selected from the group consisting of 3H, 14C, 35S, 99Tc, 123I, 125I, 131I, mIn, 97Ru, 67Ga, 68Ga, 72As, 89Zr and 201Tl.

A suitable detectable signaling label may also be fluorophore or fluorogen. Said fluorophore or fluorogen may be selected from the group consisting of fluorescein, rhodamine, dansyl, phycoerythrin, phycocyanin, allophycocyanin, o-phthaldehyde, fluorescamine, fluorescein derivative, Oregon Green, Rhodamine Green, Rhodol Green or Texas Red.

The labelled ABP may be coupled either directly or indirectly to a detectable signaling label. For example, the ABP may be coupled either directly (e.g. via tyrosine residues of the ABP) or indirectly (e.g. via a linker—as a metal chelating agent) to a detectable signaling label. In some other embodiments, the ABP may be coupled to a molecule that is able to be coupled (either in vitro or in vivo) to the detectable signaling label at the time and place of use.

A detectable signaling label may be bound to the ABP through one or more diethylenetriaminepentaacetic acid (DTPA) residues that are coupled to the ABP.

Also contemplated by the invention is an in vitro method of detecting or diagnosing a disease defined herein. Such a method may comprise contacting a sample obtained from a subject with a preferably labelled ABP of the invention. The sample may be a blood, urine or cerebrospinal fluid sample, but may preferably be a liquid sample or a biopsy sample. The disease to be detected or diagnosed is preferably leukemia, such as ALL or AML.

The terms "of the [present] invention", "in accordance with the invention", "according to the invention" and the like, as used herein are intended to refer to all aspects and embodiments of the invention described and/or claimed herein.

As used herein, the term "comprising" is to be construed as encompassing both "including" and "consisting of", both meanings being specifically intended, and hence individually disclosed embodiments in accordance with the present invention. Where used herein, "and/or" is to be taken as specific disclosure of each of the two specified features or components with or without the other. For example, "A and/or B" is to be taken as specific disclosure of each of (i) A, (ii) B and (iii) A and B, just as if each is set out individually herein. In the context of the present invention, the terms "about" and "approximately" denote an interval of accuracy that the person skilled in the art will understand to still ensure the technical effect of the feature in question. The term typically indicates deviation from the indicated numerical value by ±20%, ±15%, ±10%, and for example ±5%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. Where an indefinite or definite article is used when referring to a singular noun, e.g. "a", "an" or "the", this includes a plural of that noun unless something else is specifically stated.

It is to be understood that application of the teachings of the present invention to a specific problem or environment, and the inclusion of variations of the present invention or additional features thereto (such as further aspects and embodiments), will be within the capabilities of one having ordinary skill in the art in light of the teachings contained herein.

Unless context dictates otherwise, the descriptions and definitions of the features set out above are not limited to any particular aspect or embodiment of the invention and apply equally to all aspects and embodiments which are described.

All references, patents, and publications cited herein are hereby incorporated by reference in their entirety.

In view of the above, it will be appreciated that the present invention also relates to the following itemised embodiments:

Item 1: A bispecific antigen binding protein (ABP) which comprises a first antigen binding domain capable of binding to the human fms like tyrosine kinase 3 (FLT3) antigen, and a second antigen binding domain binding to the human cluster of differentiation 3 (CD3) antigen.

Item 2: The bispecific ABP according to item 1, wherein the bispecific ABP binds to FLT3 with an EC50 of lower than 10 nM, preferably lower than 9 nM, more preferably lower than 8 nM, more preferably lower than 7 nM, more preferably lower than 6 nM, or lower than 5.5 nM. Item 3: The bispecific ABP according to item 1 or 2, wherein the bispecific ABP binds to FLT3 with an EC50 of higher than 0.5 nM, more preferably higher than 1 nM, more preferably higher than 1.3 nM, more preferably higher than 2 nM, more preferably higher than 3 nM, or 4 nM, or higher than 4.5 nM.

Item 4: The bispecific ABP according to any one of items 1 to 3, wherein the bispecific ABP binds to FLT3 with an EC50 of lower than 10 nM and higher than 0.5 nM, more preferably of lower than 9 nM and higher than 1 nM, preferably of lower than 8 nM and higher than 1.3 nM, preferably of lower than 7 nM and higher than 3 nM, preferably of lower than 6 nM and higher than 4 nM, preferably of lower than 5.5 nM and higher than 4.5 nM, Item 5: The bispecific ABP according to any one of items 2 to 4, wherein the EC50 of the binding of the bispecific ABP to FLT3 is as determined by analyzing the binding of the bispecific ABP to FLT3 positive cells by flow cytometry using a fluorescent activated cell sorting (FACS) device; preferably wherein the FLt3 positive cells are B cell precursor leukemia cells, preferably NALM-16 cells (as deposited under ACC 680 at the DSMZ); and/or preferably wherein the binding is detected using a fluorescent labeled secondary antibody; and/or wherein the bispecific ABP is incubated with the FLT3 positive cells for about 30 min before flow cytometry.

Item 6: The bispecific ABP according to any one of items 1 to 5, wherein the bispecific ABP binds FLT3 with an kD of less than 50 μM, more preferably of less than 20 μM, more preferably less than 10 μM, more preferably less than 5 μM, more preferably less than 1 μM.

Item 7: The bispecific ABP according to any one of items 1 to 5, wherein the bispecific ABP binds FLT3 with an kD of more than 50 nM, more preferably of more than 100 nM, more preferably of more than 160 nM, more preferably of more than 200 NM, more preferably of more than 300 nM.

Item 8: The bispecific ABP according to any one of items 1 to 5, wherein the bispecific ABP binds FLT3 with an kD of less than 50 μM and more than 50 nM, more preferably of less than 20 μM and more than 100 nM, more preferably less than 10 μM and more than 160 nM, more preferably less than 5 μM and more than 200 nM, more preferably less than 1 μm and more than 300 nM.

Item 9: The bispecific ABP according to any one of items 6 to 8, wherein the kD is as measured by surface plasmon resonance, for example in a BIAcore Affinity Assay.

Item 10: The bispecific ABP according to any one of items 1 to 9, wherein the bispecific ABP binds to CD3 with an EC50 of lower than 200 nM, preferably lower than 90 nM, more preferably lower than 50 nM, more preferably lower than 20 nM, more preferably lower than 15 nM.

Item 11: The bispecific ABP according to any one of items 1 to 10, wherein the bispecific ABP binds to CD3 with an EC50 of higher than 1 nM, preferably higher than 2 nM, more preferably higher than 4.1 nM, more preferably higher than 6 nM, more preferably higher than 8 nM.

Item 12: The bispecific ABP according to any one of items 1 to 11, wherein the bispecific ABP binds to CD3 with an EC50 of lower than 200 nM and higher than 1 nM, preferably lower than 200 nM and higher than 2 nM, more preferably lower than 90 nM and higher than 4.1 nM, more preferably lower than 20 nM and higher than 6 nM, more preferably lower than 15 nM and higher than 8 nM.

Item 13: The bispecific ABP according to any one of items 10 to 12, wherein the EC50 of the binding of the bispecific ABP to CD3 is as determined by analyzing the binding of the bispecific ABP to CD3 positive cells by flow cytometry using a fluorescent activated cell sorting (FACS) device; preferably wherein the CD3 positive cells are T cell leukemia cells, preferably Jurkat cells (as deposited under ACC 282 at the DSMZ); and/or preferably wherein the binding is detected using a fluorescent labeled secondary antibody; and/or wherein the bispecific ABP is incubated with the CD3 positive cells for about 30 min before flow cytometry.

Item 14: The bispecific ABP according to any one of items 1 to 13, which inhibits proliferation and/or viability of leukemic blood mononuclear cells of a patient suffering from acute leukemia in an in-vitro assay compared to a non-treated control to equal or less than 50%, more preferably to equal or less than 40%, more preferably to equal or less than 30%, most preferably to equal or less than 25%.

Item 15: The bispecific ABP according to any one of items 1 to 14, wherein the bispecific ABP comprises two first antigen binding sites.

Item 16: The bispecific ABP according to any one of items 1 to 15, wherein the bispecific ABP comprises two second antigen binding sites.

Item 17: The bispecific ABP according to any one of items 1 to 16, which is an antibody or an antibody variant.

Item 18: The bispecific ABP according to item 17, wherein the antigen binding domain is composed of an antibody heavy chain variable domain and antibody light chain variable domain.

Item 19: The bispecific ABP according to any one of items 1 to 18, which is a tetravalent and homodimeric bispecific antibody comprising in each monomer: (i) an N-terminal Fab fragment comprising a variable region comprising a heavy chain variable domain and a light chain variable domain, wherein said variable region comprises the first antigen binding site; (ii) a C-terminal scFv fragment comprising the second antigen binding site, and wherein (i) and (ii) are connected by a CH2 and CH3 domain.

Item 20: The bispecific ABP according to any one of items 17 to 19, wherein at least one amino acid residue of the CH2 domain that is able to mediate binding to Fc receptors in said antibody is lacking or mutated.

Item 21: The bispecific ABP according to any one of items 1 to 20, wherein the second antigen binding site comprises in the orientation C- to N-terminal an antibody heavy chain variable domain and an antibody light chain variable domain.

Item 22: An ABP capable of binding to human fms related tyrosine kinase 3 (FLT3), comprising: (i) a heavy chain variable domain comprising the CDRH1 region set forth in SEQ ID NO: 01 (SYWMH), the CDRH2 region set forth in SEQ ID NO: 02 (EIDPSDSYKDYNQKFKD), and the CDRH3 region set forth in SEQ ID NO: 03 (AITTTPFDF), or wherein in each case independently the CDRH1, CDRH2 and/or CDRH3 comprise a sequence having no more than three or two, preferably no more than one amino acid substitution(s), deletion(s) or insertion(s) compared to SEQ ID NO: 01, SEQ ID NO: 02, or SEQ ID NO: 03, respectively; or comprising a CDRH1, CDRH2 or CDRH3 sequence having at least 75% sequence identity or at least 80%, preferably 90% sequence identity with SEQ ID NO: 01, SEQ ID NO: 02, or SEQ ID NO: 03; and (ii) a light chain variable domain comprising the CDRL1 region set forth in SEQ ID NO: 05 (RASQSISNNLH), the CDRL2 region set forth in SEQ ID NO: 06 (YASQSIS), and the CDRL3 region set forth in SEQ ID NO: 07 (QQSNTWPYT) or wherein in each case independently CDRL1, CDRL2 and/or CDRL3 comprise a sequence having no more than three or two, preferably no more than one amino acid substitution(s), deletion(s) or insertion(s) compared to SEQ ID NO: 05, SEQ ID NO: 06, or SEQ ID NO: 07, respectively; or comprising a CDRL1, CDRL2 or CDRL3 sequence having at least 75% sequence identity or at least 80% sequence identity with SEQ ID NO: 05, SEQ ID NO: 06, or SEQ ID NO: 07; characterized in that, said heavy chain variable region and said light chain variable region each comprise human variable region framework sequences.

Item 23: The ABP according to item 22, which is a bispecific ABP according to any one of items 1 to 21, and wherein said CDR regions of (i) and (ii) in item 22 are comprised in said first antigen binding domain.

Item 24: The ABP according to any item 22 or 23, wherein the heavy chain variable domain human framework sequences are derived from IGHV1-46, preferably IGHV1-46*3, and/or wherein the heavy chain variable domain human framework sequences are derived from IGKV3D-15.

Item 25: The ABP according to item 24, wherein the heavy chain variable region comprises any one of, or a combination of, the following mutations: K16G, V18L, K19R, V20L, K22A, M48I, K57T, N60A, M69I, T70S, T75K, S76N, V78L, M80L, E81Q, S87A, and T108L, wherein the numbering is according to the Kabat system.

Item 26: The ABP according to item 24 or 25, wherein the light chain variable region comprises any one of, or a combination of, the following mutations: Y49K, Y87F, and I55A, wherein the numbering is according to the Kabat system.

Item 27: The ABP thereof of item 1, wherein the heavy chain variable region comprises the amino acid sequence having a sequence identity of at least 80% to an amino acid sequence selected from SEQ ID NO: 15, 17, 19, 21 or 23, or, in each case independently, optionally with no more than ten, nine, eight, seven, six, five, four, preferably no more than three, two or one, amino acid substitution(s), insertion(s) or deletion(s) compared to these sequences; and/or wherein the light chain variable region comprises the amino acid sequence having a sequence identity of at least 80% to the amino acid sequence selected from SEQ ID NO: 16, 18, 20, 22 or 24, or, in each case independently, optionally with no more than ten, nine, eight, seven, six, five, four, preferably no more than three, two or one, amino acid substitution(s), insertion(s) or deletion(s) compared to these sequences.

Item 28: The ABP according to item 27, wherein in the heavy chain variable region the amino acid positions 16, 18, 19, 20, 22, 48, 57, 60, 69, 70, 75, 76, 78, 80, 81, 87, and 108 are as in any one of SEQ ID NO: 15, 17, 19, 21 or 23; and/or wherein in the light chain variable region the amino acid positions 49, 55, and 87 are as in any one of SEQ ID NO: 16, 18, 20, 22 or 24; wherein the numbering is according to the Kabat system.

Item 29: The ABP according to any one of items 1 to 28, comprising a least one, preferably two, second antigen binding domain(s), wherein said second antigen binding domain binds to CD3, preferably wherein said second antigen binding domain is fused to the heavy chain of the first antibody binding domain.

Item 30: The ABP according to item 29, wherein the second antigen binding domain comprises an scFv fragment comprising an amino acid sequence having at least 80% sequence identity to, or, in each case independently, optionally with no more than ten, nine, eight, seven, six, five, four, preferably no more than three, two or one, amino acid substitution(s), insertion(s) or deletion(s) compared to, a sequence selected from SEQ ID NO: 14, 25, 26 and 27.

Item 31: An ABP according to item 27 or 28, comprising at least one antibody heavy chain having an amino acid sequence with at least 80% sequence identity to, or having no more than twenty, fifteen, ten, nine, eight, seven, six, four, preferably three or two, preferably no more than one amino acid substitution(s), deletion(s) or insertion(s) compared to, a sequence selected from selected from SEQ ID NO: 28, 30, 32, 34, 36, 38, 40, 42, 44, 46, 48, 50, 52, 54, 56, 58, 60, 62, 64, 66, 68, 70, 72, and 74; and/or comprising at least one antibody light chain having an amino acid sequence with at least 80% sequence identity to, or having no more than twenty, fifteen, ten, nine, eight, seven, six, four, preferably three or two, preferably no more than one amino acid substitution(s), deletion(s) or insertion(s) compared to, a sequence selected from selected from SEQ ID NO: 29, 31, 33, 35, 37, 39, 41, 43, 45, 47, 49, 51, 53, 55, 57, 59, 61, 63, 65, 67, 69, 71, 73, and 75.

Item 32: The ABP according to item 31, comprising one, preferably two, antibody heavy chains and one, preferably two, antibody light chains, each comprising an amino acid sequence with at least 80% sequence identity to, or having no more than twenty, fifteen, ten, nine, eight, seven, six, four, preferably three or two, preferably no more than one amino acid substitution(s), deletion(s) or insertion(s) compared to:

a. a sequence selected from SEQ ID NO: 28 for the heavy chain and SEQ ID NO: 29 for the light chain;
b. a sequence selected from SEQ ID NO: 30 for the heavy chain and SEQ ID NO: 31 for the light chain;
c. a sequence selected from SEQ ID NO: 32 for the heavy chain and SEQ ID NO: 33 for the light chain;
d. a sequence selected from SEQ ID NO: 34 for the heavy chain and SEQ ID NO: 35 for the light chain;
e. a sequence selected from SEQ ID NO: 36 for the heavy chain and SEQ ID NO: 37 for the light chain;
f. a sequence selected from SEQ ID NO: 38 for the heavy chain and SEQ ID NO: 39 for the light chain;
g. a sequence selected from SEQ ID NO: 40 for the heavy chain and SEQ ID NO: 41 for the light chain;
h. a sequence selected from SEQ ID NO: 42 for the heavy chain and SEQ ID NO: 43 for the light chain;
i. a sequence selected from SEQ ID NO: 44 for the heavy chain and SEQ ID NO: 45 for the light chain;
j. a sequence selected from SEQ ID NO: 46 for the heavy chain and SEQ ID NO: 47 for the light chain;
k. a sequence selected from SEQ ID NO: 48 for the heavy chain and SEQ ID NO: 49 for the light chain;
l. a sequence selected from SEQ ID NO: 50 for the heavy chain and SEQ ID NO: 51 for the light chain;
m. a sequence selected from SEQ ID NO: 52 for the heavy chain and SEQ ID NO: 53 for the light chain;
n. a sequence selected from SEQ ID NO: 54 for the heavy chain and SEQ ID NO: 55 for the light chain;
o. a sequence selected from SEQ ID NO: 56 for the heavy chain and SEQ ID NO: 57 for the light chain;
p. a sequence selected from SEQ ID NO: 58 for the heavy chain and SEQ ID NO: 59 for the light chain;
q. a sequence selected from SEQ ID NO: 60 for the heavy chain and SEQ ID NO: 61 for the light chain;
r. a sequence selected from SEQ ID NO: 62 for the heavy chain and SEQ ID NO: 63 for the light chain;
s. a sequence selected from SEQ ID NO: 64 for the heavy chain and SEQ ID NO: 65 for the light chain;
t. a sequence selected from SEQ ID NO: 66 for the heavy chain and SEQ ID NO: 67 for the light chain;
u. a sequence selected from SEQ ID NO: 68 for the heavy chain and SEQ ID NO: 69 for the light chain;
v. a sequence selected from SEQ ID NO: 70 for the heavy chain and SEQ ID NO: 71 for the light chain;
w. a sequence selected from SEQ ID NO: 72 for the heavy chain and SEQ ID NO: 73 for the light chain;
x. a sequence selected from SEQ ID NO: 74 for the heavy chain and SEQ ID NO: 75 for the light chain;
wherein the heavy chain and the light chain are paired with each other.

Item 33: An ABP or an antigen-binding fragment thereof, capable of binding to human FLT3 that is able to compete with the binding of an ABP according to any one of items 1 to 32.

Item 34: The ABP of any one of items 1 to 33, having an activity to bind to a T-cell and to an FLT3 expressing tumor cell, preferably wherein the antibody increases the recruitment of T-cells to a FLT3 expressing tumor cell by binding to FLT3 and CD3.

Item 35: The ABP according to any one of items 1 to 34, wherein the heavy chain variable region and a light chain variable region of an antibody molecule comprising a second binding domain is the heavy chain variable region and a light chain variable region of UCHT1.

Item 36: The ABP according to any one of items 1 to 35, comprising constant heavy chain regions CH1 to CH3, and wherein at least one amino acid residue of the human CH2 domain that is able to mediate binding to Fc receptors is lacking or mutated.

Item 37: The ABP of any one of items 1 to 36, wherein ABP is a tetrameric antibody molecule, or a homodimeric and tetravalent antibody molecule.

Item 38: An isolated nucleic acid encoding for an ABP, or for an antigen binding fragment or a monomer of an ABP, of any one of items 1 to 37.

Item 39: A recombinant host cell comprising a nucleic acid of item 38.

Item 40: A pharmaceutical composition comprising: (i) an ABP of any one of items 1 to 37, or (ii) a nucleic acid of item 38, or (iii) a recombinant host cell according to item 39, and a pharmaceutically acceptable carrier, stabiliser and/or excipient.

Item 41: A component for use in medicine, wherein the component is selected from the list consisting of: an ABP of any one of items 1 to 37, an isolated nucleic acid of item 38, a recombinant host cell according to item 39 and a pharmaceutical composition according to item 40.

Item 42: The component for use of item 41, wherein the use in medicine is the use in the treatment of a proliferative disorder that is associated with the expression FLt3.

Item 43: The component for use of items 41 or 42, wherein the component is for use in enhancing an T cell mediated killing and/or inhibiting of proliferation of FLT3 positive tumor cells.

Item 44: The component for use according to any one of items 41 to 43, wherein the component is for use in the diagnosis, prevention and/or treatment of a proliferative disease, wherein the proliferative disease is preferably cancer, wherein the cancer is selected from leukemia, such as acute myeloid leukemia (AML) or acute lymphoblastic leukemia (ALL), or a solid cancer selected from prostate cancer, colorectal cancer, cancer of the stomach, lung carcinoma, osteosarcoma, mammary cancer, pancreatic cancer, or squamous cell carcinoma; preferably the cancer is leukemia, such as AML or ALL.

Item 45: The component for use according to item 44, wherein the cancer is associated with tumor cells expressing FLT3.

BRIEF DESCRIPTION OF THE FIGURES AND SEQUENCES

The figures show:

FIG. 1 depicts the Fc-attenuated IgGsc-format that was used for construction of the bispecific FLT3×CD3 antibody-variants described in this invention. Variants of the FLT3 antigen binding domain (V1 to V5) were obtained starting from humanization of the V-regions of the FLT3 antibody 4G8 by CDR-grafting using replacement strategies with different stringency. For generation of different CD3-antigen binding domains (V6 to V9), UCHT1 scFv sequences were used.

FIG. 2 shows the amino acid sequence of the heavy chain and light chain of CC-2. A: heavy chain sequence of the FLT3 (4G8)×CD3 (humanized hUCHT1) bispecific IgGsc format antibody molecule (SEQ ID NO: 68). The heavy chain comprises the mouse heavy chain (HC) variable region of 4G8, an IgG1 CH1 domain, an IgG1 hinge region, a modified IgG1 CH2 domain, an IgG1 CH3 domain, and a humanized CD3 (UCHT1) single chain Fv fragment. B: shows the amino acid sequence of the kappa light chain of the FLT3 (4G8)×CD3 (humanized hUCHT1) (SEQ ID NO: 69). This light chain completes the heavy chain constructs of SEQ ID NO: 68 to form a chimeric 4G8×UCHT1 IgGsc- and Fabsc-molecule, respectively (see FIG. 1).

Figure 3:
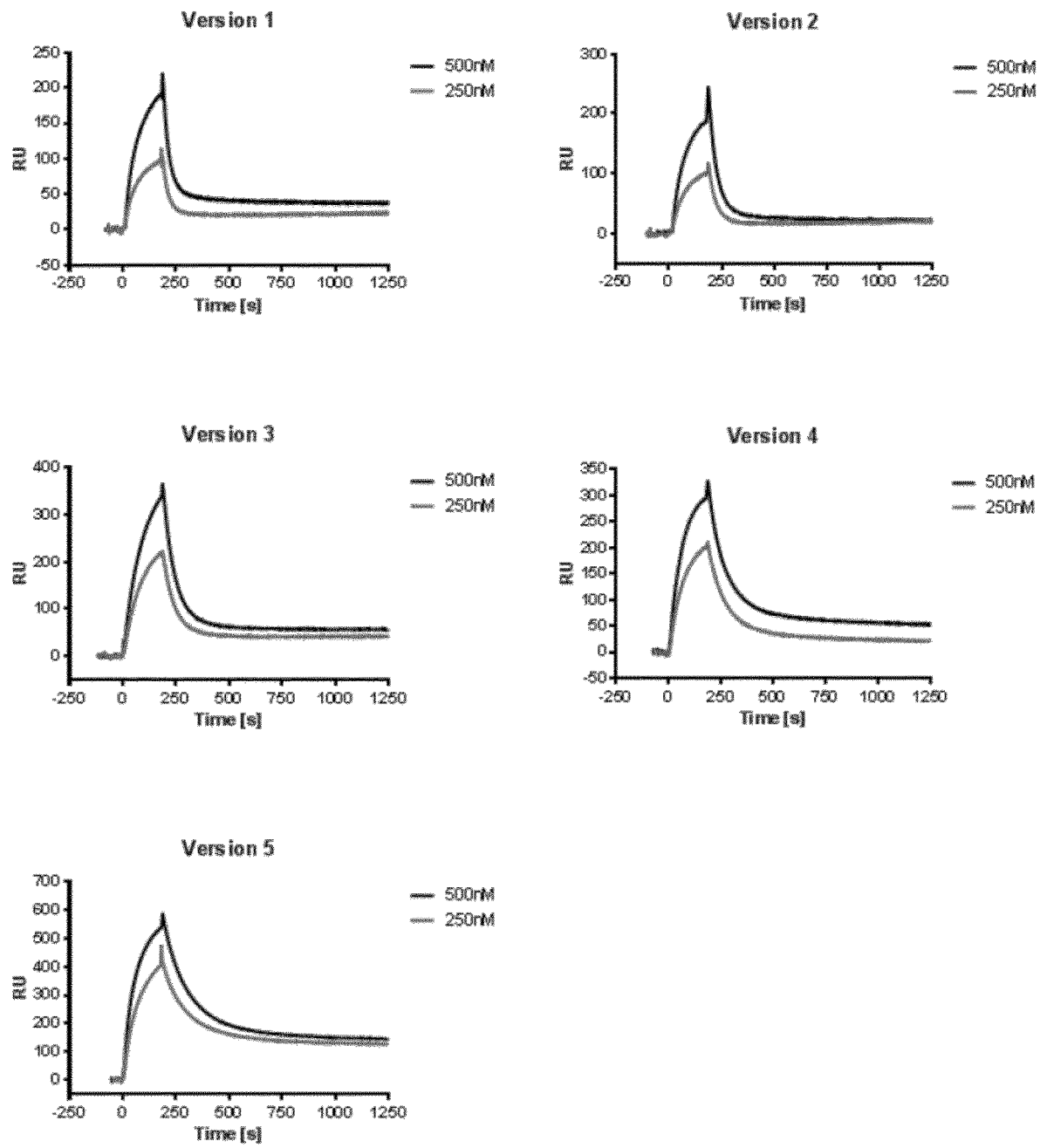

FIG. 3 depicts binding of different CC-2 variants to soluble recombinant FLT3 protein. Respective antibody variants were immobilized to a Biacore chip coated with protein A and binding of His tagged, recombinant FLT3 protein (Sino Biologicals) was determined using a Biacore X instrument (GE Healthcare). Shown are the results of various mutated variants of the FLT3 antigen binding domain (V1 to V5).

Figure 4:
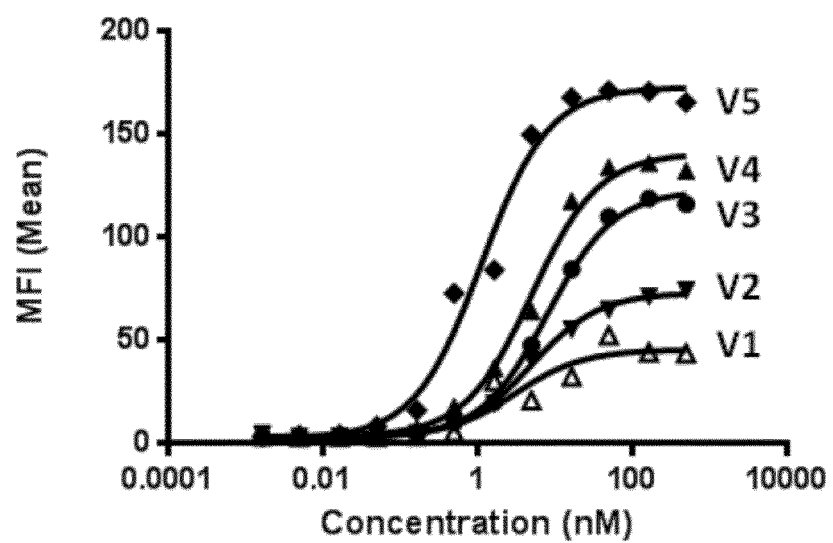

FIG. 4 shows the binding of CC-2 variants to Nalm16 cells expressing FLT3. Calculated EC50 values are indicated at the corresponding bars in FIG. 3. Tested were mutated variants of the FLT3 antigen binding domain (V1 to V5).

Figure 5:
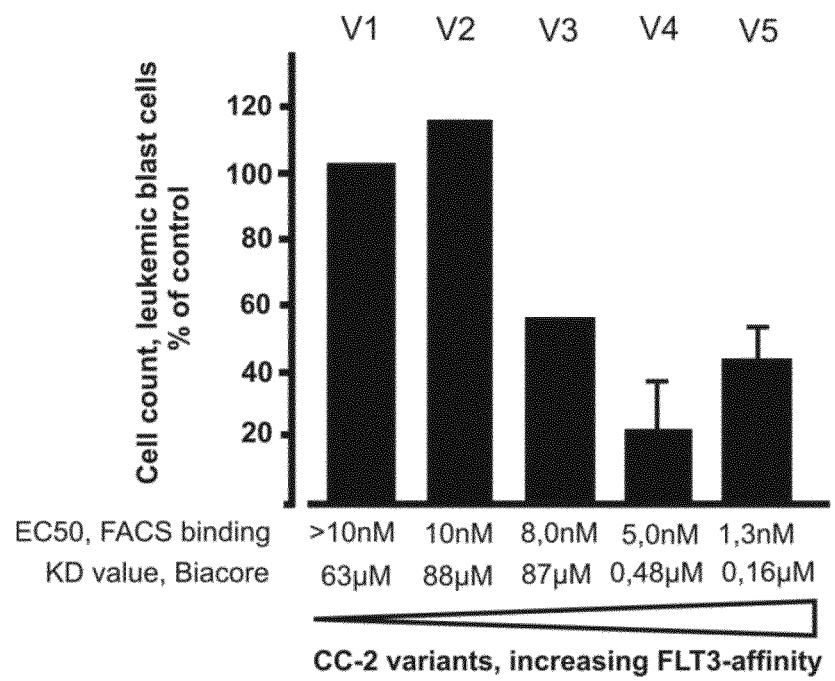

FIG. 5 depicts the depletion of leukemic cells from blood samples of AML patients using the various different CC-2 constructs of the invention. Shown is a comparison of mutated variants of the FLT3 antigen binding domain (V1 to V5). Also indicated are the values of Biacore results of FIG. 3 and flow cytometry EC50 of FIG. 4.

Figure 6:
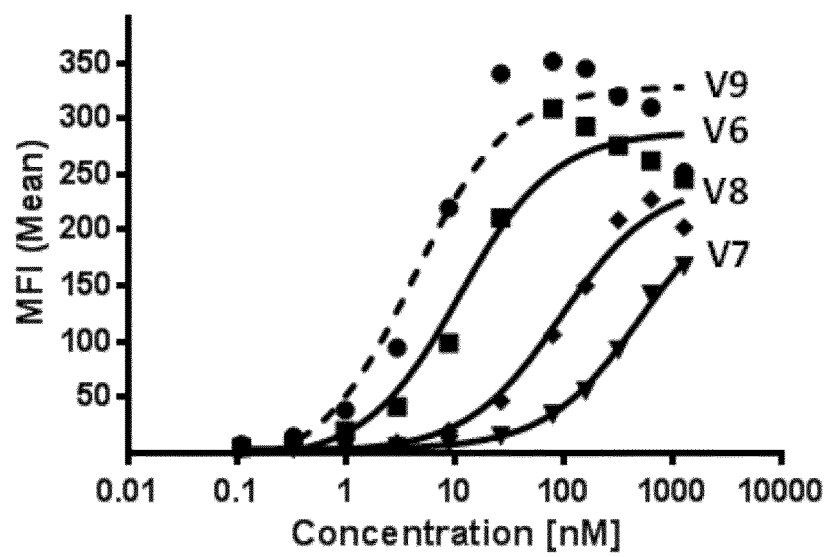

FIG. 6 shows the binding of CC-2 variants to Jurkat cells expressing CD3. Calculated EC50 values are indicated at the corresponding bars in FIG. 5. Tested were mutated variants of the CD3 antigen binding domain (V7 to V9).

Figure 7:
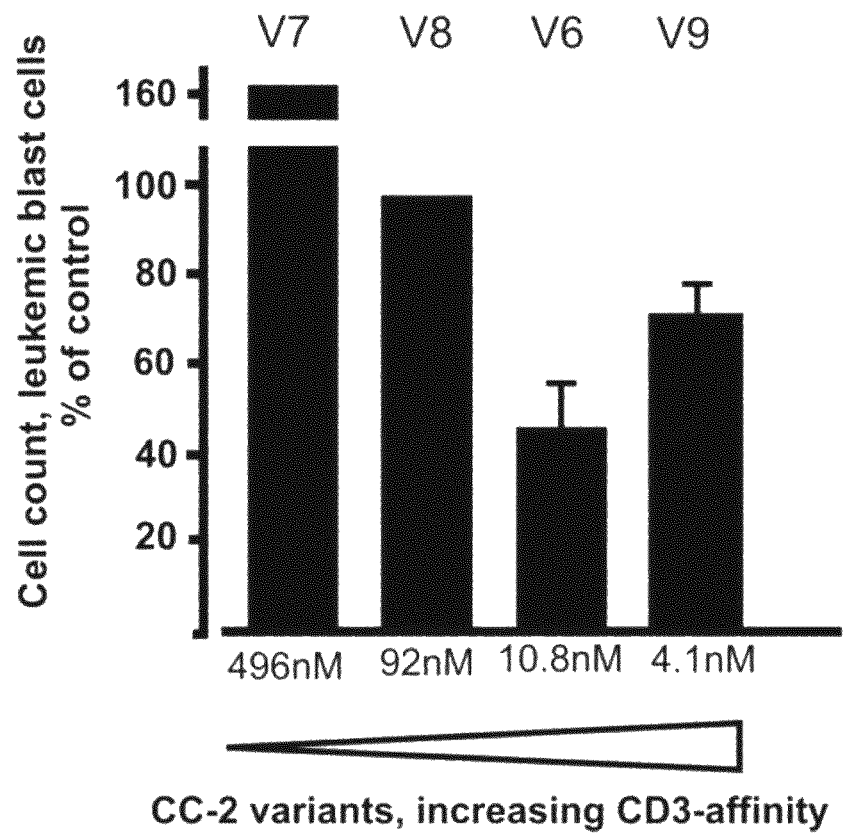

FIG. 7. depicts the depletion of leukemic cells from blood samples of AML patients using the various different CC-2 constructs of the invention. Shown is a comparison of mutated variants of the CD3 antigen binding domain (V7 to V9). Also indicated are the values of the flow cytometry EC50 of FIG. 6.

FIG. 8. depicts the results of T cell activation and blast reduction by different CC-2 variants in a flow cytometry assay. The used CC2 variants are different in both their FLT3 antigen binding domains and CD3 antigen binding domains (antibodies used are V6-V6 (V6); V6-V9 (V9); V4-V6 (V4)). A: reduction of CD4 positive cells; B: reduction of CD8 positive cells; C: Blast count.

Figure 9:
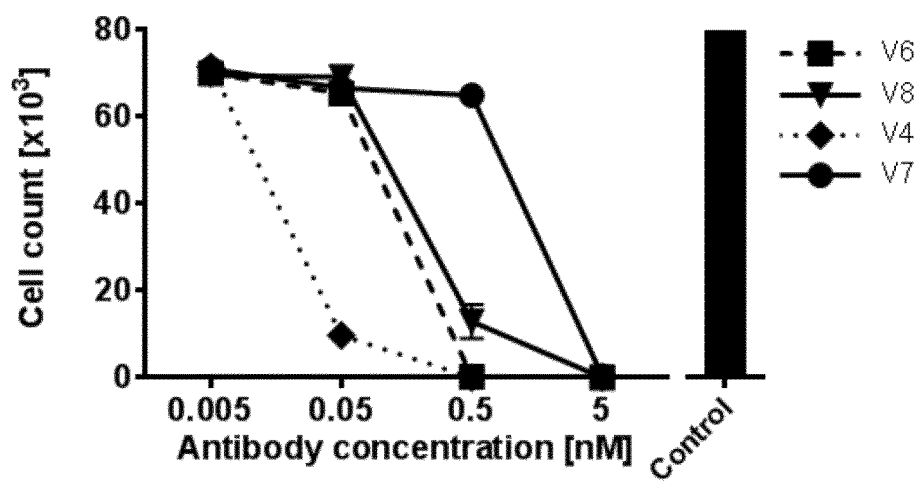

FIG. 9. depicts depletion of NALM16 leukemia cells by different variants of CC-2 in a flow cytometry assay. The used CC2 variants are different in both their FLT3 antigen binding domains and CD3 antigen binding domains (antibodies used are V6-V6 (V6); V6-V8 (V8); V4-V6 (V4); V6-V7 (V7)).

FIG. 10 depicts the anti-leukemic activity of CC-2 variant 4 in vivo in immune-deficient NSG mice engrafted with primary AML (A) or ALL (B). As an example CC-2 variants having the FLT3 antigen binding domain V4 (V4-V6) are shown.

Figure 11:
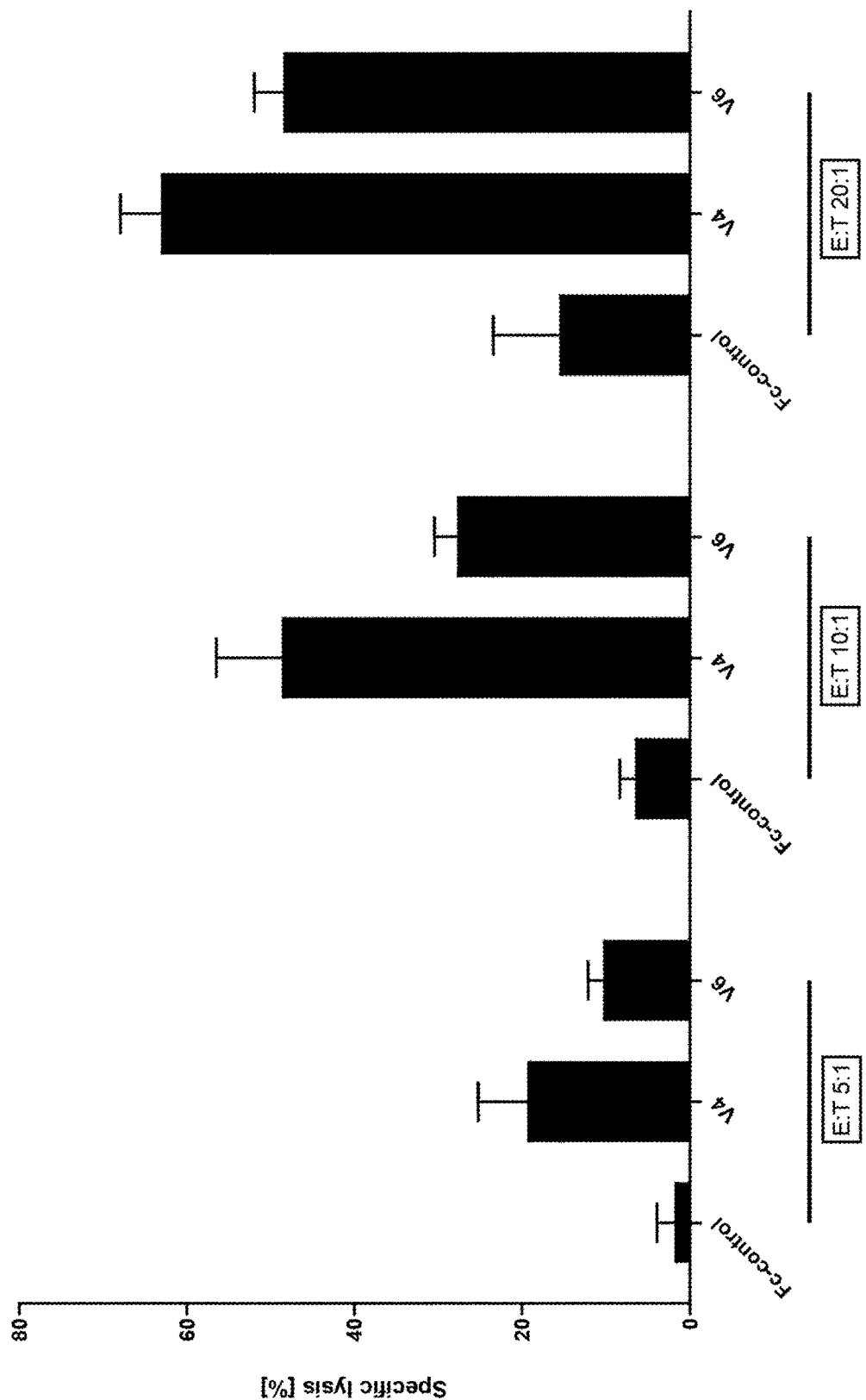

FIG. 11 depicts antibody dependent cellular cytotoxicity (ADCC) of monospecific anti-FLT3 antibody variant. Shown is the specific lysis of FLT3+ leukemic cells (SEM; DSMZ no. ACC 546) by allogeneic polyclonal natural killer cells (pNKC) in the presence of the indicated FLT3 constructs or Fc-control (each 5 µg/ml) was measured by 2h BATDA-Europium cytotoxicity assays.

The ABP of the invention are all described in the sequence listing and the following table 1:

| SEQ ID NO: | Antibody Name | Description | Sequence |
|---|---|---|---|
| 1 | V6-V6 | V6 FLT$_3$ CDRH$_1$ | SYWMH |
| 2 | V6-V6 | V6 FLT$_3$ CDRH$_2$ | EIDPSDSYKDYNQKFKD |
| 3 | V6-V6 | V6 FLT$_3$ CDRH$_3$ | AITTTPFDF |
| 4 | V6-V6 | V6 FLT$_3$ HCV | QVQLQQPGAELVKPGASLKLSCKSSGYTFTSYWMH WVRQRPGHGLEWIGEIDPSDSYKDYNQKFKDKATL TVDRSSNTAYMHLSSLTSDDSAVYYCARAITTTPFDF WGQGTTLTVSS |
| 5 | V6-V6 | V6 FLT$_3$ CDRL$_1$ | RASQSISNNLH |
| 6 | V6-V6 | V6 FLT$_3$ CDRL$_2$ | YASQSIS |
| 7 | V6-V6 | V6 FLT$_3$ CDRL$_3$ | QQSNTWPYT |
| 8 | V6-V6 | V6 FLT$_3$ LCV | DIVLTQSPATLSVTPGDSVSLSCRASQSISNNLHWYQ QKSHESPRLLIKYASQSIS- GIPSRFSGSGSGTDFTLSIN SVETEDFGVYFCQQSNTWPYTFGGGTKLEIK |
| 9 | V6-V6 | V6 FLT$_3$ LCC | RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC |
| 10 | V6-V6 | V6 CH$_1$ | ASTKGPSVFPLAPSSKSTSGGTAALGCLVKDYFPEPVT VSWNSGALTSGVHTFPAVLQSSGLYSLSSVVTVPSSS LGTQTYICNVNHKPSNTKVDKKV |
| 11 | V6-V6 | V6 Hinge | EPKSCDKTHTCPPCP |
| 12 | V6-V6 | V6 CH$_2$ | APPVAGPSVFLFPPKPKDTLMISRTPEVTCVVVGVSH EDPEVKFNWYVDGVEVHNAKTKPREEQYNSTYRVV SVLTVLHQDWLNGKEYKCKVSNKQLPSPIEKTISKAK |
| 13 | V6-V6 | V6 CH$_3$ | GQPREPQVYTLPPSRDELTKNQVSLTCLVKGFYPSDI AVEWESNGQPENNYKTTPPVLDSDGSFFLYSKLTVD KSRWQQGNVFSCSVMHEALHNHYTQKSLSLSPGKS G |
| 14 | V6-V6 | V6 CD$_3$ scFv | DIQMTQSPSSLSASVGDRVTITCRASQDIRNYLNWYQ QKPGKAPKLLIYYTSRLESGVPSRFSGSGSGTDYTLTI SSLQPEDFATYYCQQGNTLPWTFGQGTKVEIKGGGG SGGGGSGGGGSEVQLVESGGGLVQPGGSLRLSCAAS GYSFTGYTMNWVRQAPGKGLEWVALINPYKGVSTY NQKFKDRFTISVDKSKNTAYLQMNSLRAEDTAVYYC ARSGYYGDSDWYFDVWGQGTLVTVSS |
| 15 | V$_1$-V6 | V$_1$ FLT$_3$ HCV | QVQLVQSGAEVKKPGGSLRLSCAASGYTFTSYWMH WVRQAPGQGLEWIGEIDPSDSYTDYAQKFKDRVTIS RDTSKNTLYLQLSSLRAEDTAVYYCARAITTTPFDFW GQGTLVTVSS |
| 16 | V$_1$-V6 | V$_1$ FLT$_3$ LCV | EIVMTQSPATLSVSPGERATLSCRASQSISNNLHWYQ QKPGQAPRLLIYYASQSASGIPARFSGSGSGTEFTLTI SSLQSEDFAVYFCQQSNTWPYTFGGGTKLEIK |
| 17 | V$_2$-V6 | V$_2$ FLT$_3$ HCV | QVQLVQSGAEVKKPGGSLRLSCAASGYTFTSYWMH WVRQAPGQGLEWIGEIDPSDSYTDYAQKFKDRVTIS RDTSKNTLYLQLSSLRAEDTAVYYCARAITTTPFDFW GQGTLVTVSS |
| 18 | V$_2$-V6 | V$_2$ FLT$_3$ LCV | EIVMTQSPATLSVSPGERATLSCRASQSISNNLHWYQ QKPGQAPRLLIKYASQSISGIPARFSGSGSGTEFTL- TIS SLQSEDFAVYFCQQSNTWPYTFGGGTKLEIK |

-continued

| SEQ ID NO: | Antibody Name | Description | Sequence |
|---|---|---|---|
| 19 | V$_3$-V6 | V$_3$ FLT$_3$ HCV | QVQLVQSGAEVKKPGASVKVSCKASGYTFTSYWMH WVRQAPGQGLEWIGEIDPSDSYKDYNQKFKDRVTM TRDTSTSTVYMELSSLRSEDTAVYYCARAITTTPFDF WGQGTTVTVSS |
| 20 | V$_3$-V6 | V$_3$ FLT$_3$ LCV | EIVMTQSPATLSVSPGERATLSCRASQSISNNLHWYQ QKPGQAPRLLIYYASQSASGIPARFSGSGSGTEFTLTI SSLQSEDFAVYFCQQSNTWPYTFGGGTKLEIK |
| 21 | V$_4$-V6 | V$_4$ FLT$_3$ HCV | QVQLVQSGAEVKKPGASVKVSCKASGYTFTSYWMH WVRQAPGQGLEWIGEIDPSDSYKDYNQKFKDRVTM TRDTSTSTVYMELSSLRSEDTAVYYCARAITTTPFDF WGQGTTVTVSS |
| 22 | V$_4$-V6 | V$_4$ FLT$_3$ LCV | EIVMTQSPATLSVSPGERATLSCRASQSISNNLHWYQ QKPGQAPRLLIKYASQSISGIPARFSGSGSGTEFTL-TIS SLQSEDFAVYFCQQSNTWPYTFGGGTKLEIK |
| 23 | V$_5$-V6 | V$_5$ FLT$_3$ HCV | QVQLVQSGAEVKKPGGSLRLSCAASGYTFTSYWMH WVRQAPGQGLEWIGEIDPSDSYKDYNQKFKDRVTIS RDTSKNTLYLQLSSLRAEDTAVYYCARAITTTPFDFW GQGTLVTVSS |
| 24 | V$_5$-V6 | V$_5$ FLT$_3$ LCV | EIVMTQSPATLSVSPGERATLSCRASQSISNNLHWYQ QKPGQAPRLLIKYASQSISGIPARFSGSGSGTEFTL-TIS SLQSEDFAVYFCQQSNTWPYTFGGGTKLEIK |
| 25 | V6-V$_7$ | V$_7$ CD$_3$ scFv | DIQMTQSPSSLSASVGDRVTITCRASQDIRNYLNWYQ QKPGKAPKLLIYYTSRLESGVPSRFSGSGSGTDYTLTI SSLQPEDFATYYCQQGNTLPWTFGQGTKVEIKGGGG SGGGGSGGGGSEVQLVESGGGLVQPGGSLRLSCAAS GYSFTGYTMNWVRQAPGKGLEWVALINPYKGVSTY ADSFKGRFTISVDDSKNTAYLQMNSLRAEDTAVYYC ARSGYYGDSDWYFDVWGQGTLVTVSS |
| 26 | V6-V$_8$ | V8 CD$_3$ scFv | DIQMTQSPSSLSASVGDRVTITCRASQDIRNYLNWYQ QKPGKAPKLLIYYTSRLESGVPSRFSGSGSGTDYTLTI SSLQPEDFATYYCQQGNTLPWTFGQGTKVEIKGGGG SGGGGSGGGGSEVQLVESGGGLVQPGGSLRLSCAAS GYSFTGYTMNWVRQAPGKGLEWVALINPYKGVSTY NQKFKDRFTISVDDSKNTAYLQMNSLRAEDTAVYYC ARSGYYGDSDWYFDVWGQGTLVTVSS |
| 27 | V6-V$_9$ | V$_9$ CD$_3$ scFv | EVQLVESGGGLVQPGGSLRLSCAASGYSFTGYTMNW VRQAPGKGLEWVALINPYKGVSTYNQKFKDRFTISV DKSKNTAYLQMNSLRAEDTAVYYCARSGYYGDSDW YFDVWGQGTLVTVSSGGGGSGGGGSGGGGSDIQMT QSPSSLSASVGDRVTITCRASQDIRNYLNWYQQKPG KAPKLLIYYTSR-LESGVPSRFSGSGSGTDYTLTISSLQP EDFATYYCQQGNTLPWTFGQGTKVEIK |
| 28 | V$_1$-V6 | Full Length heavy | QVQLVQSGAEVKKPGGSLRLSCAASGYTFTSYWMH WVRQAPGQGLEWIGEIDPSDSYTDYAQKFKDRVTIS RDTSKNTLYLQLSSLRAEDTAVYYCARAITTTPFDFW GQGTLVTVSSASTKGPSVFPLAPSSKSTSGGTAALGCL VKDYFPEPVTVSWNSGALTSGVHTFPAVLQSSGLYSL SSVVTVPSSSLGTQTYICNVNHKPSNTKVDKKVEPKS CDKTHTCPPCPAPPVAGPSVFLFPPKPKDTLMISRTP EVTCVVVGVSHEDPEVKFNWYVDGVEVHNAKTKPR EEQYNSTYRVVSVLTVLHQDWLNGKEYKCKVSNKQ LPSPIEKTISKAKGQPREPQVYTLPPSRDELTKNQVSL TCLVKGFYPSDIAVEWESNGQPENNYKTTPPVLDSD GSFFLYSKLTVDKSRWQQGNVFSCSVMHEALHNHY TQKSLSLSPGKSGDIQMTQSPSSLSASVGDRVTITCRA SQDIRNYLNWYQQKPGKAPKLLIYYTSRLESGVPSRF SGSGSGTDYTLTISSLQPEDFATYYCQQGNTLPWTFG QGTKVEIKGGGGSGGGGSGGGGSEVQLVESGGGLV QPGGSLRLSCAASGYSFTGYTMNWVRQAPGKGLEW VALINPYKGVSTYNQKFKDRFTISVDKSKNTAYLQM NSLRAEDTAVYYCARSGYYGDSDWYFDVWGQGTLV TVSS |

-continued

| SEQ ID NO: | Antibody Name | Description | Sequence |
|---|---|---|---|
| 29 | V₁-V6 | Full Length light | EIVMTQSPATLSVSPGERATLSCRASQSISNNLHWYQ QKPGQAPRLLIYYASQSASGIPARFSGSGSGTEFTLTI SSLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 30 | V₂-V6 | Full Length heavy | QVQLVQSGAEVKKPGGSLRLSCAASGYTFTSYWMH WVRQAPGQGLEWIGEIDPSDSYTDYAQKFKDRVTIS RDTSKNTLYLQLSSLRAEDTAVYYCARAITTTPFDFW GQGTLVTVSSASTKGPSVFPLAPSSKSTSGGTAALGCL VKDYFPEPVTVSWNSGALTSGVHTFPAVLQSSGLYSL SSVVTVPSSSLGTQTYICNVNHKPSNTKVDKKVEPKS CDKTHTCPPCPAPPVAGPSVFLFPPKPKDTLMISRTP EVTCVVVGVSHEDPEVKFNWYVDGVEVHNAKTKPR EEQYNSTYRVVSVLTVLHQDWLNGKEYKCKVSNKQ LPSPIEKTISKAKGQPREPQVYTLPPSRDELTKNQVSL TCLVKGFYPSDIAVEWESNGQPENNYKTTPPVLDSD GSFFLYSKLTVDKSRWQQGNVFSCSVMHEALHNHY TQKSLSLSPGKSGDIQMTQSPSSLSASVGDRVTITCRA SQDIRNYLNWYQQKPGKAPKLLIYYTSRLESGVPSRF SGSGSGTDYTLTISSLQPEDFATYYCQQGNTLPWTFG QGTKVEIKGGGGSGGGGSGGGGSEVQLVESGGGLV QPGGSLRLSCAASGYSFTGYTMNWVRQAPGKGLEW VALINPYKGVSTYNQKFKDRFTISVDKSKNTAYLQM NSLRAEDTAVYYCARSGYYGDSDWYFDVWGQGTLV TVSS |
| 31 | V₂-V6 | Full Length light | EIVMTQSPATLSVSPGERATLSCRASQSISNNLHWYQ QKPGQAPRLLIKYASQSISGIPARFSGSGSGTEFTL-TIS SLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 32 | V₃-V6 | Full Length heavy | QVQLVQSGAEVKKPGASVKVSCKASGYTFTSYWMH WVRQAPGQGLEWIGEIDPSDSYKDYNQKFKDRVTM TRDTSTSTVYMELSSLRSEDTAVYYCARAITTTPFDF WGQGTTVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKKVEP KSCDKTHTCPPCPAPPVAGPSVFLFPPKPKDTLMISR TPEVTCVVVGVSHEDPEVKFNWYVDGVEVHNAKTK PREEQYNSTYRVVSVLTVLHQDWLNGKEYKCKVSN KQLPSPIEKTISKAKGQPREPQVYTLPPSRDELTKNQ VSLTCLVKGFYPSDIAVEWESNGQPENNYKTTPPVL DSDGSFFLYSKLTVDKSRWQQGNVFSCSVMHEALH NHYTQKSLSLSPGKSGDIQMTQSPSSLSASVGDRVTI TCRASQDIRNYLNWYQQKPGKAPKLLIYYTSRLESGV PSRFSGSGSGTDYTLTISSLQPEDFATYYCQQGNTLP WTFGQGTKVEIKGGGGSGGGGSGGGGSEVQLVESG GGLVQPGGSLRLSCAASGYSFTGYTMNWVRQAPGK GLEWVALINPYKGVSTYNQKFKDRFTISVDKSKNTA YLQMNSLRAEDTAVYYCARSGYYGDSDWYFDVWGQ GTLVTVSS |
| 33 | V₃-V6 | Full Length light | EIVMTQSPATLSVSPGERATLSCRASQSISNNLHWYQ QKPGQAPRLLIYYASQSASGIPARFSGSGSGTEFTLTI SSLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 34 | V₄-V6 | Full Length heavy | QVQLVQSGAEVKKPGASVKVSCKASGYTFTSYWMH WVRQAPGQGLEWIGEIDPSDSYKDYNQKFKDRVTM TRDTSTSTVYMELSSLRSEDTAVYYCARAITTTPFDF WGQGTTVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKKVEP KSCDKTHTCPPCPAPPVAGPSVFLFPPKPKDTLMISR TPEVTCVVVGVSHEDPEVKFNWYVDGVEVHNAKTK PREEQYNSTYRVVSVLTVLHQDWLNGKEYKCKVSN KQLPSPIEKTISKAKGQPREPQVYTLPPSRDELTKNQ VSLTCLVKGFYPSDIAVEWESNGQPENNYKTTPPVL DSDGSFFLYSKLTVDKSRWQQGNVFSCSVMHEALH |

| SEQ ID NO: | Antibody Name | Description | Sequence |
|---|---|---|---|
| | | | NHYTQKSLSLSPGKSGDIQMTQSPSSLSASVGDRVTI TCRASQDIRNYLNWYQQKPGKAPKLLIYYTSRLESGV PSRFSGSGSGTDYTLTISSLQPEDFATYYCQQGNTLP WTFGQGTKVEIKGGGGSGGGGSGGGGSEVQLVESG GGLVQPGGSLRLSCAASGYSFTGYTMNWVRQAPGK GLEWVALINPYKGVSTYNQKFKDRFTISVDKSKNTA YLQMNSLRAEDTAVYYCARSGYYGDSDWYFDVWGQ GTLVTVSS |
| 35 | V$_4$-V6 | Full Length light | EIVMTQSPATLSVSPGERATLSCRASQSISNNLHWYQ QKPGQAPRLLIKYASQSISGIPARFSGSGSGTEFTL-TIS SLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 36 | V$_5$-V6 | Full Length heavy | QVQLVQSGAEVKKPGGSLRLSCAASGYTFTSYWMH WVRQAPGQGLEWIGEIDPSDSYKDYNQKFKDRVTIS RDTSKNTLYLQLSSLRAEDTAVYYCARAITTTPFDFW GQGTLVTVSSASTKGPSVFPLAPSSKSTSGGTAALGCL VKDYFPEPVTVSWNSGALTSGVHTFPAVLQSSGLYSL SSVVTVPSSSLGTQTYICNVNHKPSNTKVDKKVEPKS CDKTHTCPPCPAPPVAGPSVFLFPPKPKDTLMISRTP EVTCVVVGVSHEDPEVKFNWYVDGVEVHNAKTKPR EEQYNSTYRVVSVLTVLHQDWLNGKEYKCKVSNKQ LPSPIEKTISKAKGQPREPQVYTLPPSRDELTKNQVSL TCLVKGFYPSDIAVEWESNGQPENNYKTTPPVLDSD GSFFLYSKLTVDKSRWQQGNVFSCSVMHEALHNHY TQKSLSLSPGKSGDIQMTQSPSSLSASVGDRVTITCRA SQDIRNYLNWYQQKPGKAPKLLIYYTSRLESGVPSRF SGSGSGTDYTLTISSLQPEDFATYYCQQGNTLPWTFG QGTKVEIKGGGGSGGGGSGGGGSEVQLVESGGGLV QPGGSLRLSCAASGYSFTGYTMNWVRQAPGKGLEW VALINPYKGVSTYNQKFKDRFTISVDKSKNTAYLQM NSLRAEDTAVYYCARSGYYGDSDWYFDVWGQGTLV TVSS |
| 37 | V$_5$-V6 | Full Length light | EIVMTQSPATLSVSPGERATLSCRASQSISNNLHWYQ QKPGQAPRLLIKYASQSISGIPARFSGSGSGTEFTL-TIS SLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 38 | V$_1$-V$_7$ | Full Length heavy | QVQLVQSGAEVKKPGGSLRLSCAASGYTFTSYWMH WVRQAPGQGLEWIGEIDPSDSYTDYAQKFKDRVTIS RDTSKNTLYLQLSSLRAEDTAVYYCARAITTTPFDFW GQGTLVTVSSASTKGPSVFPLAPSSKSTSGGTAALGCL VKDYFPEPVTVSWNSGALTSGVHTFPAVLQSSGLYSL SSVVTVPSSSLGTQTYICNVNHKPSNTKVDKKVEPKS CDKTHTCPPCPAPPVAGPSVFLFPPKPKDTLMISRTP EVTCVVVGVSHEDPEVKFNWYVDGVEVHNAKTKPR EEQYNSTYRVVSVLTVLHQDWLNGKEYKCKVSNKQ LPSPIEKTISKAKGQPREPQVYTLPPSRDELTKNQVSL TCLVKGFYPSDIAVEWESNGQPENNYKTTPPVLDSD GSFFLYSKLTVDKSRWQQGNVFSCSVMHEALHNHY TQKSLSLSPGKSGDIQMTQSPSSLSASVGDRVTITCRA SQDIRNYLNWYQQKPGKAPKLLIYYTSRLESGVPSRF SGSGSGTDYTLTISSLQPEDFATYYCQQGNTLPWTFG QGTKVEIKGGGGSGGGGSGGGGSEVQLVESGGGLV QPGGSLRLSCAASGYSFTGYTMNWVRQAPGKGLEW VALINPYKGVSTYADSFKGRFTISVDDSKNTAYLQMN SLRAEDTAVYYCARSGYYGDSDWYFDVWGQGTLVT VSS |
| 39 | V$_1$-V$_7$ | Full Length light | EIVMTQSPATLSVSPGERATLSCRASQSISNNLHWYQ QKPGQAPRLLIYYASQSASGIPARFSGSGSGTEFTLTI SSLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 40 | V$_2$-V$_7$ | Full Length heavy | QVQLVQSGAEVKKPGGSLRLSCAASGYTFTSYWMH WVRQAPGQGLEWIGEIDPSDSYTDYAQKFKDRVTIS |

| SEQ ID NO: | Antibody Name | Description | Sequence |
|---|---|---|---|
| | | | RDTSKNTLYLQLSSLRAEDTAVYYCARAITTTPFDFW GQGTLVTVSSASTKGPSVFPLAPSSKSTSGGTAALGCL VKDYFPEPVTVSWNSGALTSGVHTFPAVLQSSGLYSL SSVVTVPSSSLGTQTYICNVNHKPSNTKVDKKVEPKS CDKTHTCPPCPAPPVAGPSVFLFPPKPKDTLMISRTP EVTCVVVGVSHEDPEVKFNWYVDGVEVHNAKTKPR EEQYNSTYRVVSVLTVLHQDWLNGKEYKCKVSNKQ LPSPIEKTISKAKGQPREPQVYTLPPSRDELTKNQVSL TCLVKGFYPSDIAVEWESNGQPENNYKTTPPVLDSD GSFFLYSKLTVDKSRWQQGNVFSCSVMHEALHNHY TQKSLSLSPGKSGDIQMTQSPSSLSASVGDRVTITCRA SQDIRNYLNWYQQKPGKAPKLLIYYTSRLESGVPSRF SGSGSGTDYTLTISSLQPEDFATYYCQQGNTLPWTFG QGTKVEIKGGGGSGGGGSGGGGSEVQLVESGGGLV QPGGSLRLSCAASGYSFTGYTMNWVRQAPGKGLEW VALINPYKGVSTYADSFKGRFTISVDDSKNTAYLQMN SLRAEDTAVYYCARSGYYGDSDWYFDVWGQGTLVT VSS |
| 41 | $V_2$-$V_7$ | Full Length light | EIVMTQSPATLSVSPGERATLSCRASQSISNNLHWYQ QKPGQAPRLLIKYASQSISGIPARFSGSGSGTEFTL- TIS SLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 42 | $V_3$-$V_7$ | Full Length heavy | QVQLVQSGAEVKKPGASVKVSCKASGYTFTSYWMH WVRQAPGQGLEWIGEIDPSDSYKDYNQKFKDRVTM TRDTSTSTVYMELSSLRSEDTAVYYCARAITTTPFDF WGQGTTVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKKVEP KSCDKTHTCPPCPAPPVAGPSVFLFPPKPKDTLMISR TPEVTCVVVGVSHEDPEVKFNWYVDGVEVHNAKTK PREEQYNSTYRVVSVLTVLHQDWLNGKEYKCKVSN KQLPSPIEKTISKAKGQPREPQVYTLPPSRDELTKNQ VSLTCLVKGFYPSDIAVEWESNGQPENNYKTTPPVL DSDGSFFLYSKLTVDKSRWQQGNVFSCSVMHEALH NHYTQKSLSLSPGKSGDIQMTQSPSSLSASVGDRVTI TCRASQDIRNYLNWYQQKPGKAPKLLIYYTSRLESGV PSRFSGSGSGTDYTLTISSLQPEDFATYYCQQGNTLP WTFGQGTKVEIKGGGGSGGGGSGGGGSEVQLVESG GGLVQPGGSLRLSCAASGYSFTGYTMNWVRQAPGK GLEWVALINPYKGVSTYADSFKGRFTISVDDSKNTAY LQMNSLRAEDTAVYYCARSGYYGDSDWYFDVWGQG TLVTVSS |
| 43 | $V_3$-$V_7$ | Full Length light | EIVMTQSPATLSVSPGERATLSCRASQSISNNLHWYQ QKPGQAPRLLIYYASQSASGIPARFSGSGSGTEFTLTI SSLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 44 | $V_4$-$V_7$ | Full Length heavy | QVQLVQSGAEVKKPGASVKVSCKASGYTFTSYWMH WVRQAPGQGLEWIGEIDPSDSYKDYNQKFKDRVTM TRDTSTSTVYMELSSLRSEDTAVYYCARAITTTPFDF WGQGTTVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKKVEP KSCDKTHTCPPCPAPPVAGPSVFLFPPKPKDTLMISR TPEVTCVVVGVSHEDPEVKFNWYVDGVEVHNAKTK PREEQYNSTYRVVSVLTVLHQDWLNGKEYKCKVSN KQLPSPIEKTISKAKGQPREPQVYTLPPSRDELTKNQ VSLTCLVKGFYPSDIAVEWESNGQPENNYKTTPPVL DSDGSFFLYSKLTVDKSRWQQGNVFSCSVMHEALH NHYTQKSLSLSPGKSGDIQMTQSPSSLSASVGDRVTI TCRASQDIRNYLNWYQQKPGKAPKLLIYYTSRLESGV PSRFSGSGSGTDYTLTISSLQPEDFATYYCQQGNTLP WTFGQGTKVEIKGGGGSGGGGSGGGGSEVQLVESG GGLVQPGGSLRLSCAASGYSFTGYTMNWVRQAPGK GLEWVALINPYKGVSTYADSFKGRFTISVDDSKNTAY LQMNSLRAEDTAVYYCARSGYYGDSDWYFDVWGQG TLVTVSS |

| SEQ ID NO: | Antibody Name | Description | Sequence |
|---|---|---|---|
| 45 | V₄-V₇ | Full Length light | EIVMTQSPATLSVSPGERATLSCRASQSISNNLHWYQ QKPGQAPRLLIKYASQSISGIPARFSGSGSGTEFTL-TIS SLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 46 | V₅-V₇ | Full Length heavy | QVQLVQSGAEVKKPGGSLRLSCAASGYTFTSYWMH WVRQAPGQGLEWIGEIDPSDSYKDYNQKFKDRVTIS RDTSKNTLYLQLSSLRAEDTAVYYCARAITTTPFDFW GQGTLVTVSSASTKGPSVFPLAPSSKSTSGGTAALGCL VKDYFPEPVTVSWNSGALTSGVHTFPAVLQSSGLYSL SSVVTVPSSSLGTQTYICNVNHKPSNTKVDKKVEPKS CDKTHTCPPCPAPPVAGPSVFLFPPKPKDTLMISRTP EVTCVVVGVSHEDPEVKFNWYVDGVEVHNAKTKPR EEQYNSTYRVVSVLTVLHQDWLNGKEYKCKVSNKQ LPSPIEKTISKAKGQPREPQVYTLPPSRDELTKNQVSL TCLVKGFYPSDIAVEWESNGQPENNYKTTPPVLDSD GSFFLYSKLTVDKSRWQQGNVFSCSVMHEALHNHY TQKSLSLSPGKSGDIQMTQSPSSLSASVGDRVTITCRA SQDIRNYLNWYQQKPGKAPKLLIYYTSRLESGVPSRF SGSGSGTDYTLTISSLQPEDFATYYCQQGNTLPWTFG QGTKVEIKGGGGSGGGGSGGGGSEVQLVESGGGLV QPGGSLRLSCAASGYSFTGYTMNWVRQAPGKGLEW VALINPYKGVSTYADSFKGRFTISVDDSKNTAYLQMN SLRAEDTAVYYCARSGYYGDSDWYFDVWGQGTLVT VSS |
| 47 | V₅-V₇ | Full Length light | EIVMTQSPATLSVSPGERATLSCRASQSISNNLHWYQ QKPGQAPRLLIKYASQSISGIPARFSGSGSGTEFTL-TIS SLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 48 | V₁-V8 | Full Length heavy | QVQLVQSGAEVKKPGGSLRLSCAASGYTFTSYWMH WVRQAPGQGLEWIGEIDPSDSYTDYAQKFKDRVTIS RDTSKNTLYLQLSSLRAEDTAVYYCARAITTTPFDFW GQGTLVTVSSASTKGPSVFPLAPSSKSTSGGTAALGCL VKDYFPEPVTVSWNSGALTSGVHTFPAVLQSSGLYSL SSVVTVPSSSLGTQTYICNVNHKPSNTKVDKKVEPKS CDKTHTCPPCPAPPVAGPSVFLFPPKPKDTLMISRTP EVTCVVVGVSHEDPEVKFNWYVDGVEVHNAKTKPR EEQYNSTYRVVSVLTVLHQDWLNGKEYKCKVSNKQ LPSPIEKTISKAKGQPREPQVYTLPPSRDELTKNQVSL TCLVKGFYPSDIAVEWESNGQPENNYKTTPPVLDSD GSFFLYSKLTVDKSRWQQGNVFSCSVMHEALHNHY TQKSLSLSPGKSGDIQMTQSPSSLSASVGDRVTITCRA SQDIRNYLNWYQQKPGKAPKLLIYYTSRLESGVPSRF SGSGSGTDYTLTISSLQPEDFATYYCQQGNTLPWTFG QGTKVEIKGGGGSGGGGSGGGGSEVQLVESGGGLV QPGGSLRLSCAASGYSFTGYTMNWVRQAPGKGLEW VALINPYKGVSTYNQKFKDRFTISVDDSKNTAYLQM NSLRAEDTAVYYCARSGYYGDSDWYFDVWGQGTLV TVSS |
| 49 | V₁-V8 | Full Length light | EIVMTQSPATLSVSPGERATLSCRASQSISNNLHWYQ QKPGQAPRLLIYYASQSASGIPARFSGSGSGTEFTLTI SSLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 50 | V₂-V8 | Full Length heavy | QVQLVQSGAEVKKPGGSLRLSCAASGYTFTSYWMH WVRQAPGQGLEWIGEIDPSDSYTDYAQKFKDRVTIS RDTSKNTLYLQLSSLRAEDTAVYYCARAITTTPFDFW GQGTLVTVSSASTKGPSVFPLAPSSKSTSGGTAALGCL VKDYFPEPVTVSWNSGALTSGVHTFPAVLQSSGLYSL SSVVTVPSSSLGTQTYICNVNHKPSNTKVDKKVEPKS CDKTHTCPPCPAPPVAGPSVFLFPPKPKDTLMISRTP EVTCVVVGVSHEDPEVKFNWYVDGVEVHNAKTKPR EEQYNSTYRVVSVLTVLHQDWLNGKEYKCKVSNKQ LPSPIEKTISKAKGQPREPQVYTLPPSRDELTKNQVSL TCLVKGFYPSDIAVEWESNGQPENNYKTTPPVLDSD |

| SEQ ID NO: | Antibody Name | Description | Sequence |
|---|---|---|---|
| | | | GSFFLYSKLTVDKSRWQQGNVFSCSVMHEALHNHY TQKSLSLSPGKSGDIQMTQSPSSLSASVGDRVTITCRA SQDIRNYLNWYQQKPGKAPKLLIYYTSRLESGVPSRF SGSGSGTDYTLTISSLQPEDFATYYCQQGNTLPWTFG QGTKVEIKGGGGSGGGGSGGGGSEVQLVESGGGLV QPGGSLRLSCAASGYSFTGYTMNWVRQAPGKGLEW VALINPYKGVSTYNQKFKDRFTISVDDSKNTAYLQM NSLRAEDTAVYYCARSGYYGDSDWYFDVWGQGTLV TVSS |
| 51 | V$_2$-V8 | Full Length light | EIVMTQSPATLSVSPGERATLSCRASQSISNNLHWYQ QKPGQAPRLLIKYASQSISGIPARFSGSGSGTEFTL-TIS SLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 52 | V$_3$-V8 | Full Length heavy | QVQLVQSGAEVKKPGASVKVSCKASGYTFTSYWMH WVRQAPGQGLEWIGEIDPSDSYKDYNQKFKDRVTM TRDTSTSTVYMELSSLRSEDTAVYYCARAITTTPFDF WGQGTTVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKKVEP KSCDKTHTCPPCPAPPVAGPSVFLFPPKPKDTLMISR TPEVTCVVVGVSHEDPEVKFNWYVDGVEVHNAKTK PREEQYNSTYRVVSVLTVLHQDWLNGKEYKCKVSN KQLPSPIEKTISKAKGQPREPQVYTLPPSRDELTKNQ VSLTCLVKGFYPSDIAVEWESNGQPENNYKTTPPVL DSDGSFFLYSKLTVDKSRWQQGNVFSCSVMHEALH NHYTQKSLSLSPGKSGDIQMTQSPSSLSASVGDRVTI TCRASQDIRNYLNWYQQKPGKAPKLLIYYTSRLESGV PSRFSGSGSGTDYTLTISSLQPEDFATYYCQQGNTLP WTFGQGTKVEIKGGGGSGGGGSGGGGSEVQLVESG GGLVQPGGSLRLSCAASGYSFTGYTMNWVRQAPGK GLEWVALINPYKGVSTYNQKFKDRFTISVDDSKNTA YLQMNSLRAEDTAVYYCARSGYYGDSDWYFDVWGQ GTLVTVSS |
| 53 | V$_3$-V8 | Full Length light | EIVMTQSPATLSVSPGERATLSCRASQSISNNLHWYQ QKPGQAPRLLIYYASQSASGIPARFSGSGSGTEFTLTI SSLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 54 | V$_4$-V8 | Full Length heavy | QVQLVQSGAEVKKPGASVKVSCKASGYTFTSYWMH WVRQAPGQGLEWIGEIDPSDSYKDYNQKFKDRVTM TRDTSTSTVYMELSSLRSEDTAVYYCARAITTTPFDF WGQGTTVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKKVEP KSCDKTHTCPPCPAPPVAGPSVFLFPPKPKDTLMISR TPEVTCVVVGVSHEDPEVKFNWYVDGVEVHNAKTK PREEQYNSTYRVVSVLTVLHQDWLNGKEYKCKVSN KQLPSPIEKTISKAKGQPREPQVYTLPPSRDELTKNQ VSLTCLVKGFYPSDIAVEWESNGQPENNYKTTPPVL DSDGSFFLYSKLTVDKSRWQQGNVFSCSVMHEALH NHYTQKSLSLSPGKSGDIQMTQSPSSLSASVGDRVTI TCRASQDIRNYLNWYQQKPGKAPKLLIYYTSRLESGV PSRFSGSGSGTDYTLTISSLQPEDFATYYCQQGNTLP WTFGQGTKVEIKGGGGSGGGGSGGGGSEVQLVESG GGLVQPGGSLRLSCAASGYSFTGYTMNWVRQAPGK GLEWVALINPYKGVSTYNQKFKDRFTISVDDSKNTA YLQMNSLRAEDTAVYYCARSGYYGDSDWYFDVWGQ GTLVTVSS |
| 55 | V$_4$-V8 | Full Length light | EIVMTQSPATLSVSPGERATLSCRASQSISNNLHWYQ QKPGQAPRLLIKYASQSISGIPARFSGSGSGTEFTL-TIS SLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |

| SEQ ID NO: | Antibody Name | Description | Sequence |
|---|---|---|---|
| 56 | V₅-V8 | Full Length heavy | QVQLVQSGAEVKKPGGSLRLSCAASGYTFTSYWMH WVRQAPGQGLEWIGEIDPSDSYKDYNQKFKDRVTIS RDTSKNTLYLQLSSLRAEDTAVYYCARAITTTPFDFW GQGTLVTVSSASTKGPSVFPLAPSSKSTSGGTAALGCL VKDYFPEPVTVSWNSGALTSGVHTFPAVLQSSGLYSL SSVVTVPSSSLGTQTYICNVNHKPSNTKVDKKVEPKS CDKTHTCPPCPAPPVAGPSVFLFPPKPKDTLMISRTP EVTCVVVGVSHEDPEVKFNWYVDGVEVHNAKTKPR EEQYNSTYRVVSVLTVLHQDWLNGKEYKCKVSNKQ LPSPIEKTISKAKGQPREPQVYTLPPSRDELTKNQVSL TCLVKGFYPSDIAVEWESNGQPENNYKTTPPVLDSD GSFFLYSKLTVDKSRWQQGNVFSCSVMHEALHNHY TQKSLSLSPGKSGDIQMTQSPSSLSASVGDRVTITCRA SQDIRNYLNWYQQKPGKAPKLLIYYTSRLESGVPSRF SGSGSGTDYTLTISSLQPEDFATYYCQQGNTLPWTFG QGTKVEIKGGGGSGGGGSGGGGSEVQLVESGGGLV QPGGSLRLSCAASGYSFTGYTMNWVRQAPGKGLEW VALINPYKGVSTYNQKFKDRFTISVDDSKNTAYLQM NSLRAEDTAVYYCARSGYYGDSDWYFDVWGQGTLV TVSS |
| 57 | V₅-V8 | Full Length light | EIVMTQSPATLSVSPGERATLSCRASQSISNNLHWYQ QKPGQAPRLLIKYASQSISGIPARFSGSGSGTEFTL- TIS SLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 58 | V₁-V₉ | Full Length heavy | QVQLVQSGAEVKKPGGSLRLSCAASGYTFTSYWMH WVRQAPGQGLEWIGEIDPSDSYTDYAQKFKDRVTIS RDTSKNTLYLQLSSLRAEDTAVYYCARAITTTPFDFW GQGTLVTVSSASTKGPSVFPLAPSSKSTSGGTAALGCL VKDYFPEPVTVSWNSGALTSGVHTFPAVLQSSGLYSL SSVVTVPSSSLGTQTYICNVNHKPSNTKVDKKVEPKS CDKTHTCPPCPAPPVAGPSVFLFPPKPKDTLMISRTP EVTCVVVGVSHEDPEVKFNWYVDGVEVHNAKTKPR EEQYNSTYRVVSVLTVLHQDWLNGKEYKCKVSNKQ LPSPIEKTISKAKGQPREPQVYTLPPSRDELTKNQVSL TCLVKGFYPSDIAVEWESNGQPENNYKTTPPVLDSD GSFFLYSKLTVDKSRWQQGNVFSCSVMHEALHNHY TQKSLSLSPGKSGEVQLVESGGGLVQPGGSLRLSCAA SGYSFTGYTMNWVRQAPGKGLEWVALINPYKGVST YNQKFKDRFTISVDKSKNTAYLQMNSLRAEDTAVYY CARSGYYGDSDWYFDVWGQGTLVTVSSGGGGSGGG GSGGGGSDIQMTQSPSSLSASVGDRVTITCRASQDIR NYLNWYQQKPGKAPKLLIYYTSRLESGVPSRFSGSGS GTDYTLTISSLQPEDFATYYCQQGNTLPWTFGQGTK VEIK |
| 59 | V₁-V₉ | Full Length light | EIVMTQSPATLSVSPGERATLSCRASQSISNNLHWYQ QKPGQAPRLLIYYASQSASGIPARFSGSGSGTEFTLTI SSLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 60 | V₂-V₉ | Full Length heavy | QVQLVQSGAEVKKPGGSLRLSCAASGYTFTSYWMH WVRQAPGQGLEWIGEIDPSDSYTDYAQKFKDRVTIS RDTSKNTLYLQLSSLRAEDTAVYYCARAITTTPFDFW GQGTLVTVSSASTKGPSVFPLAPSSKSTSGGTAALGCL VKDYFPEPVTVSWNSGALTSGVHTFPAVLQSSGLYSL SSVVTVPSSSLGTQTYICNVNHKPSNTKVDKKVEPKS CDKTHTCPPCPAPPVAGPSVFLFPPKPKDTLMISRTP EVTCVVVGVSHEDPEVKFNWYVDGVEVHNAKTKPR EEQYNSTYRVVSVLTVLHQDWLNGKEYKCKVSNKQ LPSPIEKTISKAKGQPREPQVYTLPPSRDELTKNQVSL TCLVKGFYPSDIAVEWESNGQPENNYKTTPPVLDSD GSFFLYSKLTVDKSRWQQGNVFSCSVMHEALHNHY TQKSLSLSPGKSGEVQLVESGGGLVQPGGSLRLSCAA SGYSFTGYTMNWVRQAPGKGLEWVALINPYKGVST YNQKFKDRFTISVDKSKNTAYLQMNSLRAEDTAVYY |

| SEQ ID NO: | Antibody Name | Description | Sequence |
|---|---|---|---|
| | | | CARSGYYGDSDWYFDVWGQGTLVTVSSGGGGSGGG GSGGGGSDIQMTQSPSSLSASVGDRVTITCRASQDIR NYLNWYQQKPGKAPKLLIYYTSRLESGVPSRFSGSGS GTDYTLTISSLQPEDFATYYCQQGNTLPWTFGQGTK VEIK |
| 61 | V₂-V₉ | Full Length light | EIVMTQSPATLSVSPGERATLSCRASQSISNNLHWYQ QKPGQAPRLLIKYASQSISGIPARFSGSGSGTEFTL- TIS SLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 62 | V₃-V₉ | Full Length heavy | QVQLVQSGAEVKKPGASVKVSCKASGYTFTSYWMH WVRQAPGQGLEWIGEIDPSDSYKDYNQKFKDRVTM TRDTSTSTVYMELSSLRSEDTAVYYCARAITTTPFDF WGQGTTVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKKVEP KSCDKTHTCPPCPAPPVAGPSVFLFPPKPKDTLMISR TPEVTCVVVGVSHEDPEVKFNWYVDGVEVHNAKTK PREEQYNSTYRVVSVLTVLHQDWLNGKEYKCKVSN KQLPSPIEKTISKAKGQPREPQVYTLPPSRDELTKNQ VSLTCLVKGFYPSDIAVEWESNGQPENNYKTTPPVL DSDGSFFLYSKLTVDKSRWQQGNVFSCSVMHEALH NHYTQKSLSLSPGKSGEVQLVESGGGLVQPGGSLRL SCAASGYSFTGYTMNWVRQAPGKGLEWVALINPYK GVSTYNQKFKDRFTISVDKSKNTAYLQMNSLRAEDT AVYYCARSGYYGDSDWYFDVWGQGTLVTVSSGGGG SGGGGSGGGGSDIQMTQSPSSLSASVGDRVTITCRAS QDIRNYLNWYQQKPGKAPKLLIYYTSRLESGVPSRFS GSGSGTDYTLTISSLQPEDFATYYCQQGNTLPWTFGQ GTKVEIK |
| 63 | V₃-V₉ | Full Length light | EIVMTQSPATLSVSPGERATLSCRASQSISNNLHWYQ QKPGQAPRLLIYYASQSASGIPARFSGSGSGTEFTLTI SSLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 64 | V₄-V₉ | Full Length heavy | QVQLVQSGAEVKKPGASVKVSCKASGYTFTSYWMH WVRQAPGQGLEWIGEIDPSDSYKDYNQKFKDRVTM TRDTSTSTVYMELSSLRSEDTAVYYCARAITTTPFDF WGQGTTVTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKKVEP KSCDKTHTCPPCPAPPVAGPSVFLFPPKPKDTLMISR TPEVTCVVVGVSHEDPEVKFNWYVDGVEVHNAKTK PREEQYNSTYRVVSVLTVLHQDWLNGKEYKCKVSN KQLPSPIEKTISKAKGQPREPQVYTLPPSRDELTKNQ VSLTCLVKGFYPSDIAVEWESNGQPENNYKTTPPVL DSDGSFFLYSKLTVDKSRWQQGNVFSCSVMHEALH NHYTQKSLSLSPGKSGEVQLVESGGGLVQPGGSLRL SCAASGYSFTGYTMNWVRQAPGKGLEWVALINPYK GVSTYNQKFKDRFTISVDKSKNTAYLQMNSLRAEDT AVYYCARSGYYGDSDWYFDVWGQGTLVTVSSGGGG SGGGGSGGGGSDIQMTQSPSSLSASVGDRVTITCRAS QDIRNYLNWYQQKPGKAPKLLIYYTSRLESGVPSRFS GSGSGTDYTLTISSLQPEDFATYYCQQGNTLPWTFGQ GTKVEIK |
| 65 | V₄-V₉ | Full Length light | EIVMTQSPATLSVSPGERATLSCRASQSISNNLHWYQ QKPGQAPRLLIKYASQSISGIPARFSGSGSGTEFTL- TIS SLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 66 | V₅-V₉ | Full Length heavy | QVQLVQSGAEVKKPGGSLRLSCAASGYTFTSYWMH WVRQAPGQGLEWIGEIDPSDSYKDYNQKFKDRVTIS RDTSKNTLYLQLSSLRAEDTAVYYCARAITTTPFDFW GQGTLVTVSSASTKGPSVFPLAPSSKSTSGGTAALGCL VKDYFPEPVTVSWNSGALTSGVHTFPAVLQSSGLYSL |

| SEQ ID NO: | Antibody Name | Description | Sequence |
|---|---|---|---|
| | | | SSVVTVPSSSLGTQTYICNVNHKPSNTKVDKKVEPKS CDKTHTCPPCPAPPVAGPSVFLFPPKPKDTLMISRTP EVTCVVVGVSHEDPEVKFNWYVDGVEVHNAKTKPR EEQYNSTYRVVSVLTVLHQDWLNGKEYKCKVSNKQ LPSPIEKTISKAKGQPREPQVYTLPPSRDELTKNQVSL TCLVKGFYPSDIAVEWESNGQPENNYKTTPPVLDSD GSFFLYSKLTVDKSRWQQGNVFSCSVMHEALHNHY TQKSLSLSPGKSGEVQLVESGGGLVQPGGSLRLSCAA SGYSFTGYTMNWVRQAPGKGLEWVALINPYKGVST YNQKFKDRFTISVDKSKNTAYLQMNSLRAEDTAVYY CARSGYYGDSDWYFDVWGQGTLVTVSSGGGGSGGG GSGGGGSDIQMTQSPSSLSASVGDRVTITCRASQDIR NYLNWYQQKPGKAPKLLIYYTSRLESGVPSRFSGSGS GTDYTLTISSLQPEDFATYYCQQGNTLPWTFGQGTK VEIK |
| 67 | V₅-V₉ | Full Length light | EIVMTQSPATLSVSPGERATLSCRASQSISNNLHWYQ QKPGQAPRLLIKYASQSISGIPARFSGSGSGTEFTL-TIS SLQSEDFAVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 68 | V6-V6 | Full Length heavy | QVQLQQPGAELVKPGASLKLSCKSSGYTFTSYWMH WVRQRPGHGLEWIGEIDPSDSYKDYNQKFKDKATL TVDRSSNTAYMHLSSLTSDDSAVYYCARAITTTPFDF WGQGTTLTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKKVEP KSCDKTHTCPPCPAPPVAGPSVFLFPPKPKDTLMISR TPEVTCVVVGVSHEDPEVKFNWYVDGVEVHNAKTK PREEQYNSTYRVVSVLTVLHQDWLNGKEYKCKVSN KQLPSPIEKTISKAKGQPREPQVYTLPPSRDELTKNQ VSLTCLVKGFYPSDIAVEWESNGQPENNYKTTPPVL DSDGSFFLYSKLTVDKSRWQQGNVFSCSVMHEALH NHYTQKSLSLSPGKSGDIQMTQSPSSLSASVGDRVTI TCRASQDIRNYLNWYQQKPGKAPKLLIYYTSRLESGV PSRFSGSGSGTDYTLTISSLQPEDFATYYCQQGNTLP WTFGQGTKVEIKGGGGSGGGGSGGGGSEVQLVESG GGLVQPGGSLRLSCAASGYSFTGYTMNWVRQAPGK GLEWVALINPYKGVSTYNQKFKDRFTISVDKSKNTA YLQMNSLRAEDTAVYYCARSGYYGDSDWYFDVWGQ GTLVTVSS |
| 69 | V6-V6 | Full Length light | DIVLTQSPATLSVTPGDSVSLSCRASQSISNNLHWYQ QKSHESPRLLIKYASQSIS-GIPSRFSGSGSGTDFTLSIN SVETEDFGVYFCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 70 | V6-V₇ | Full Length heavy | QVQLQQPGAELVKPGASLKLSCKSSGYTFTSYWMH WVRQRPGHGLEWIGEIDPSDSYKDYNQKFKDKATL TVDRSSNTAYMHLSSLTSDDSAVYYCARAITTTPFDF WGQGTTLTVSSASTKGPSVFPLAPSSKSTSGGTAALG CLVKDYFPEPVTVSWNSGALTSGVHTFPAVLQSSGLY SLSSVVTVPSSSLGTQTYICNVNHKPSNTKVDKKVEP KSCDKTHTCPPCPAPPVAGPSVFLFPPKPKDTLMISR TPEVTCVVVGVSHEDPEVKFNWYVDGVEVHNAKTK PREEQYNSTYRVVSVLTVLHQDWLNGKEYKCKVSN KQLPSPIEKTISKAKGQPREPQVYTLPPSRDELTKNQ VSLTCLVKGFYPSDIAVEWESNGQPENNYKTTPPVL DSDGSFFLYSKLTVDKSRWQQGNVFSCSVMHEALH NHYTQKSLSLSPGKSGDIQMTQSPSSLSASVGDRVTI TCRASQDIRNYLNWYQQKPGKAPKLLIYYTSRLESGV PSRFSGSGSGTDYTLTISSLQPEDFATYYCQQGNTLP WTFGQGTKVEIKGGGGSGGGGSGGGGSEVQLVESG GGLVQPGGSLRLSCAASGYSFTGYTMNWVRQAPGK GLEWVALINPYKGVSTYADSFKGRFTISVDDSKNTAY LQMNSLRAEDTAVYYCARSGYYGDSDWYFDVWGQG TLVTVSS |

| SEQ ID NO: | Antibody Name | Description | Sequence |
|---|---|---|---|
| 71 | V6-V7 | Full Length light | DIVLTQSPATLSVTPGDSVSLSCRASQSISNNLHWYQQKSHESPRLLIKYASQSIS-GIPSRFSGSGSGTDFTLSINSVETEDFGVYFCQQSNTWPYTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 72 | V6-V8 | Full Length heavy | QVQLQQPGAELVKPGASLKLSCKSSGYTFTSYWMHWVRQRPGHGLEWIGEIDPSDSYKDYNQKFKDKATLTVDRSSNTAYMHLSSLTSDDSAVYYCARAITTTPFDFWGQGTTLTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVGVSHEDPEVKFNWYVDGVEVHNAKTKPREEQYNSTYRVVSVLTVLHQDWLNGKEYKCKVSNKQLPSPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGKSGDIQMTQSPSSLSASVGDRVTITCRASQDIRNYLNWYQQKPGKAPKLLIYYTSRLESGVPSRFSGSGSGTDYTLTISSLQPEDFATYYCQQGNTLPWTFGQGTKVEIKGGGGSGGGGSGGGGSEVQLVESGGGLVQPGGSLRLSCAASGYSFTGYTMNWVRQAPGKGLEWVALINPYKGVSTYNQKFKDRFTISVDDSKNTAYLQMNSLRAEDTAVYYCARSGYYGDSDWYFDVWGQGTLVTVSS |
| 73 | V6-V8 | Full Length light | DIVLTQSPATLSVTPGDSVSLSCRASQSISNNLHWYQQKSHESPRLLIKYASQSIS-GIPSRFSGSGSGTDFTLSINSVETEDFGVYFCQQSNTWPYTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 74 | V6-V9 | Full Length heavy | QVQLQQPGAELVKPGASLKLSCKSSGYTFTSYWMHWVRQRPGHGLEWIGEIDPSDSYKDYNQKFKDKATLTVDRSSNTAYMHLSSLTSDDSAVYYCARAITTTPFDFWGQGTTLTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPPVAGPSVFLFPPKPKDTLMISRTPEVTCVVVGVSHEDPEVKFNWYVDGVEVHNAKTKPREEQYNSTYRVVSVLTVLHQDWLNGKEYKCKVSNKQLPSPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGKSGEVQLVESGGGLVQPGGSLRLSCAASGYSFTGYTMNWVRQAPGKGLEWVALINPYKGVSTYNQKFKDRFTISVDKSKNTAYLQMNSLRAEDTAVYYCARSGYYGDSDWYFDVWGQGTLVTVSSGGGGSGGGGSGGGGSDIQMTQSPSSLSASVGDRVTITCRASQDIRNYLNWYQQKPGKAPKLLIYYTSRLESGVPSRFSGSGSGTDYTLTISSLQPEDFATYYCQQGNTLPWTFGQGTKVEIK |
| 75 | V6-V9 | Full Length light | DIVLTQSPATLSVTPGDSVSLSCRASQSISNNLHWYQQKSHESPRLLIKYASQSIS-GIPSRFSGSGSGTDFTLSINSVETEDFGVYFCQQSNTWPYTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 76 | Vo-V6 | Vo FLT3 HCV | QVQLVQSGAEVKKPGASVKVSCKASGYTFTSYWMHWVRQAPGQGLEWMGEIDPSDSYKDYNQKFKDRVTMTRDTSTSTVYMELSSLRSEDTAVYYCARAITTTPFDFWGQGTTVTVSS |
| 77 | Vo-V6 | Vo FLT3 LCV | EIVMTQSPATLSVSPGERATLSCRASQSISNNLHWYQQKPGQAPRLLIYYASQSISGIPARFSGSGSGTEFTL-TISSLQSEDFAVYYCQQSNTWPYTFGGGTKLEIK |

| SEQ ID NO: | Antibody Name | Description | Sequence |
|---|---|---|---|
| 78 | Vo-V6 | Full Length heavy | QVQLVQSGAEVKKPGASVKVSCKASGYTFTSYWMH WVRQAPGQGLEWMGEIDPSDSYKDYNQKFKDRVT MTRDTSTSTVYMELSSLRSEDTAVYYCARAITTTPFD FWGQGTTVTVSSASTKGPSVFPLAPSSKSTSGGTAAL GCLVKDYFPEPVTVSWNSGALTSGVHTFPAVLQSSG LYSLSSVVTVPSSSLGTQTYICNVNHKPSNTKVDKKV EPKSCDKTHTCPPCPAPPVAGPSVFLFPPKPKDTLMI SRTPEVTCVVVGVSHEDPEVKFNWYVDGVEVHNAK TKPREEQYNSTYRVVSVLTVLHQDWLNGKEYKCKVS NKQLPSPIEKTISKAKGQPREPQVYTLPPSRDELTKN QVSLTCLVKGFYPSDIAVEWESNGQPENNYKTTPPV LDSDGSFFLYSKLTVDKSRWQQGNVFSCSVMHEAL HNHYTQKSLSLSPGKSGDIQMTQSPSSLSASVGDRVT ITCRASQDIRNYLNWYQQKPGKAPKLLIYYTSRLESG VPSRFSGSGSGTDYTLTISSLQPEDFATYYCQQGNTLP WTFGQGTKVEIKGGGGSGGGGSGGGGSEVQLVESG GGLVQPGGSLRLSCAASGYSFTGYTMNWVRQAPGK GLEWVALINPYKGVSTYNQKFKDRFTISVDKSKNTA YLQMNSLRAEDTAVYYCARSGYYGDSDWYFDVWGQ GTLVTVSS |
| 79 | Vo-V6 | Full Length light | EIVMTQSPATLSVSPGERATLSCRASQSISNNLHWYQ QKPGQAPRLLIYYASQSISGIPARFSGSGSGTEFTL-TIS SLQSEDFAVYYCQQSNTWPYTFGGGTKLEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |

EXAMPLES

Certain aspects and embodiments of the invention will now be illustrated by way of example and with reference to the description, figures and tables set out herein. Such examples of the methods, uses and other aspects of the present invention are representative only, and should not be taken to limit the scope of the present invention to only such representative examples.

The examples show:

Example 1: Production of Recombinant Bispecific FLT3×CD3 ABPs (CC-2)

The 4G8 anti-FLT3 antibody was used for construction of recombinant bispecific ABPs in the IgGsc format (FIG. 1), that is, the variable domain of the mouse FLT3 antibody 4G8 was fused to human constant regions and variable regions of the CD3 antibody UCHT1 in the following order. VL-CL for the light chain and VH-CH1-CH2mod-CH3-scFv(UCHT1) for the heavy chain (see FIG. 1). In these ABPs, the FLT3 binding site is present as Fab2 fragment while the CD3 binding site is present as scFv fragment (cf. again FIG. 1). To abrogate FcR-binding, the following modifications were introduced into the hinge region and the CH2 domain (EU-index): E233P; L234V; L235A; ΔG236; D265G; A327Q; A330S (see in this respect also International patent application WO 2013/092001). The constructs were cloned in an expression vector derived from pcDNA3.1 (InVitrogen, Thermo Fisher) as also described in International patent application WO 2013/092001 and transiently transfected into CHO-cells. ABPs were purified from the supernatants of transfected cells by affinity chromatography with Protein A resins. (purchased from GE Health Care Freiburg, Germany). The resulting mouse FLT3×CD3 bispecific antibody is denoted V6-V6.

Example 2: Generation of Humanized 4G8 Antibodies

The 4G8 anti-FLT3 antibody was humanized by grafting the CDR regions of the light chain of the antibody 4G8 (that means the CDR loops of SEQ ID NO: 5 to SEQ ID NO: 7) into (the variable domain) of the human κ light sequence IGKV3-15*01 that is deposited in the IMGT/LIGM-database under accession number M23090, see also Ichiyoshi Y., Zhou M., Casali P. A human anti-insulin IgG autoantibody apparently arises through clonal selection from an insulin-specific 'germ-line' natural antibody template. Analysis by V gene segment reassortment and site-directed mutagenesis' J. Immunol. 154(1):226-238 (1995). Further the CDR regions of the heavy chain of the antibody 4G8 (that means the CDR loops of SEQ ID NO: 01 to SEQ ID NO: 03) were included into the (variable domains) of the heavy chain sequence IGHV1-46*03 which is deposited in the IMGT/LIGM-database under accession number L06612 (See also Watson C. T., et al. Complete haplotype sequence of the human immunoglobulin heavy-chain variable, diversity, and joining genes and characterization of allelic and copy-number variation. Am. J. Hum. Genet. 92(4):530-546 (2013). The resulting humanized 4G8 was used as a basis for the mutational analysis/variations of the present invention.

Example 3: Generation of Inventive Variants of Bispecific FLT3×CD3 ABPs (CC-2)

Multiple variants (V1 to V5) of the FLT3 binding domain of humanized 4G8 were generated. Furthermore, multiple published variants of the CD3 binding domain scFv derived from the humanized CD3 antibody UCHT1 (V7 to V9) were used in various combinations with the inventive FLT3 binding domain variants. The following preferred mutated variants having specific technical effects that are desirous for the use of such humanized 4G8 variants were identified (CDRs are underlined, and mutations are indicated vis-à-vis the corresponding heavy and light chains present in the humanized 4G8 FLT3 antigen binding domain detonated as Variant 0 or V0):

Humanized 4G8 FLT3 Variable Region Variant 1 (V1)
Heavy chain variable region:
Mutations: K16G, V18L, K19R, V20L, K22A, K57T, N60A, M69I, T70S, T75K, S76N, V78L, M80L, E81Q, S87A, T108L QVQLVQSGAEVKKPGGSLRLSCAASGYTFTSYWMHWVRQAPGQGLEWIG
EIDPSDSYTDYAQKFKDRVTISRDTSKNTLYLQLSSLRAEDTAVYYCAR
AITTTPFDFWGQGTLVTVSS.

Light chain variable region:

Mutations: K49Y, I55A

EIVMTQSPATLSVSPGERATLSCRASQSISNNLHWYQQKPGQAPRLLIY
YASQSASGIPARFSGSGSGTEFTLTISSLQSEDFAVYFCQQSNTWPYTF
GGGTKLEIK

Humanized 4G8 FLT3 Variable Region Variant 2 (V2)

Heavy chain variable region:

Mutations: K16G, V18L, K19R, V20L, K22A, K57T, N60A, M69I, T70S, T75K, S76N, V78L, M80L, E81Q, S87A, T108L QVQLVQSGAEVKKPGGSLRLSCAASGYTFTSYWMHWVRQAPGQGLEWIG
EIDPSDSYTDYAQKFKDRVTISRDTSKNTLYLQLSSLRAEDTAVYYCAR
AITTTPFDFWGQGTLVTVSS Light chain variable region:

EIVMTQSPATLSVSPGERATLSCRASQSISNNLHWYQQKPGQAPRLLIK
YASQSISGIPARESGSGSGTEFTLTISSLQSEDFAVYFCQQSNTWPYTF
GGGTKLEIK

Humanized 4G8 FLT3 Variable Region Variant 3 (V3)

Heavy chain variable region:

Mutations: 48I

QVQLVQSGAEVKKPGASVKVSCKASGYTFTSYWMHWVRQAPGQGLEWIG
EIDPSDSYKDYNQKFKDRVTMTRDTSTSTVYMELSSLRSEDTAVYYCAR
AITTTPFDFWGQGTTVTVSS

Light chain variable region:

Mutations: K49Y, I55A

EIVMTQSPATLSVSPGERATLSCRASQSISNNLHWYQQKPGQAPRLLIY
YASQSASGIPARFSGSGSGTEFTLTISSLQSEDFAVYFCQQSNTWPYTF
GGGTKLEIK

Humanized 4G8 FLT3 Variable Region Variant 4 (V4)

Heavy chain variable region:

Mutations: 48I

QVQLVQSGAEVKKPGASVKVSCKASGYTFTSYWMHWVRQAPGQGLEWIG
EIDPSDSYKDYNQKFKDRVTMTRDTSTSTVYMELSSLRSEDTAVYYCAR
AITTTPFDFWGQGTTVTVSS

Light chain variable region:

Mutations: 49K, 87F

EIVMTQSPATLSVSPGERATLSCRASQSISNNLHWYQQKPGQAPRLLIK
YASQSISGIPARFSGSGSGTEFTLTISSLQSEDFAVYFCQQSNTWPYTF
GGGTKLEIK

Humanized 4G8 FLT3 Variable Region Variant r (V5)

Heavy chain variable region:

Mutations: K16G, V18L, K19R, V20L, K22A, M69I, T70S, T75K, S76N, V78L, M80L, E81Q, S87A, T108L QVQLVQSGAEVKKPGGSLRLSCAASGYTFTSYWMHWVRQAPGQGLEWIG
EIDPSDSYKDYNQKFKDRVTISRDTSKNTLYLQLSSLRAEDTAVYYCAR
AITTTPFDFWGQGTLVTVSS Light chain variable region:

EIVMTQSPATLSVSPGERATLSCRASQSISNNLHWYQQKPGQAPRLLIK
YASQSISGIPARFSGSGSGTEFTLTISSLQSEDFAVYFCQQSNTWPYTF
GGGTKLEIK

Humanized UCHT1 CD3 scFv Variant 1 (V7)

Mutations: N60A, Q61D, K62S, D65G, K73D

DIQMTQSPSSLSASVGDRVTITCRASQDIRNYLNWYQQKPGKAPKLLIY
YTSRLESGVPSRFSGSGSGTDYTLTISSLQPEDFATYYCQQGNTLPWTF
GQGTKVEIKGGGGSGGGGSGGGGSEVQLVESGGGLVQPGGSLRLSCAAS
GYSFTGYTMNWVRQAPGKGLEWVALINPYKGVSTYADSFKGRFTISVDD
SKNTAYLQMNSLRAEDTAVYYCARSGYYGDSDWYFDVWGQGTLVTVSS

Humanized UCHT1 CD3 scFv Variant 2 (V8)

Mutations: K73D

DIQMTQSPSSLSASVGDRVTITCRASQDIRNYLNWYQQKPGKAPKLLIY
YTSRLESGVPSRFSGSGSGTDYTLTISSLQPEDFATYYCQQGNTLPWTF
GQGTKVEIKGGGGSGGGGSGGGGSEVQLVESGGGLVQPGGSLRLSCAAS
GYSFTGYTMNWVRQAPGKGLEWVALINPYKGVSTYNQKFKDRFTISVDD
SKNTAYLQMNSLRAEDTAVYYCARSGYYGDSDWYFDVWGQGTLVTVSS

Humanized UCHT1 CD3 scFv Variant 3 (Vg)
Mutations: light chain-heavy chain replacement (VL-VH→VH-VL):

EVQLVESGGGLVQPGGSLRLSCAASGYSFTGYTMNWVRQAPGKGLEWVA

LINPYKGVSTYNQKFKDRFTISVDKSKNTAYLQMNSLRAEDTAVYYCAR

SGYYGDSDWYFDVWGQGTLVTVSSGGGGSGGGGSGGGGSDIQMTQSPSS

LSASVGDRVTITCRASQDIRNYLNWYQQKPGKAPKLLIYYTSRLESGVP

SRFSGSGSGTDYTLTISSLQPEDFATYYCQQGNTLPWTFGQGTKVEIK

The above variants were used to create the bispecific ABP versions as indicated in the above table 1.

Example 4: Binding Affinity of FLT3 Antigen Binding Domain Variants of the Humanized 4G8

In FIG. 3 the binding of different FLT3 binding domain variants V1 to V5 as indicated above was tested for their dissociation constant using a soluble recombinant FLT3 protein. Respective antibody variants were immobilized to a Biacore chip coated with protein A and binding of His tagged, recombinant FLT3 protein (Sino Biologicals) was determined using a Biacore X instrument (GE Healthcare). Results are indicated in table 2:

|  | ka [1/Ms] | Ka-STD | kd [1/s] | Kd-STD | KD [M] | KD-STD |
|---|---|---|---|---|---|---|
| Version 1 | 489 | 380.4235 | 0.022 | 0.00113137 | 6.3E−05 | 4.7023E−05 |
| Version 2 | 539.5 | 454.6697 | 0.03175 | 0.00289914 | 8.8E−05 | 6.8377E−05 |
| Version 3 | 276.5 | 71.41779 | 0.02335 | 0.0006364 | 8.7E−05 | 2.0011E−05 |
| Version 4 | 18850 | 3747.666 | 0.00887 | 8.4853E−05 | 4.8E−07 | 9.1924E−08 |
| Version 5 | 29650 | 7848.885 | 0.00449 | 0.00041012 | 1.6E−07 | 5.5861E−08 |

In addition, antibody binding affinity was also tested using binding of the antibody to its target(s) as expressed on cells. Analyzed is the binding of CC-2 variants to Nalm16 cells expressing FLT3 (FIG. 4) or Jurkat cells expressing CD3 (FIG. 6). Variants V1 to V9 (with V6 being V6-V6) were produced after transient transfection of CHO cells using the insert sequences listed above. The antibodies were purified by protein A affinity- and size exclusion-chromatography. V1 to V5 contain different variants of the FLT3 antibody as indicated above and an identical CD3 binding antibody (a UCHT1 variant that binds to CD3 with an EC50 of ~10 nM). V6 to V9 contain the parental 4G8 antibody that binds to FLT3 with an EC50 of ~1 nM and different UCHT1 variants. To measure antibody binding to FLT3 and CD3 NALM16 (FLT3+) and Jurkat (CD3+) cells were incubated with the respective variants for 30 min, washed, stained with a goat anti human Fcγ-specific and PE-conjugated secondary antibody (Jackson Immuno Research), washed again and analyzed by flow cytometry (FACSCalibur, BD Biosciences).

Conclusions: As shown in FIGS. 3 and 4 variant 5 has the highest binding affinity to FLT3 followed by V4 as measured by surface plasmon resonance (Biacore) and flow cytometry, respectively.

Example 5: Depletion of Leukemic Cells from Blood Samples of AML Patients of Different FLT3-Binding or CD3-Binding Domain Variants Peripheral blood mononuclear cells (PBMC) were obtained from patients with acute leukemia by density gradient centrifugation, incubated for 5 days with the indicated CC-2 variants at 1 µg/ml and analyzed by flow cytometry using a FACSCanto-II (BD Biosciences). Leukemic cells were identified using antibodies to CD33, CD34 or CD117. For calibration of cell numbers a defined amount of compensation beads (BD Biosciences) was added to every sample. Data were obtained from three (V4, V5, V6, V9) and two (V3) independent experiments with cells from two different donors. All values were related to data obtained with a control IgGsc antibody with unrelated specificity. Results for FLT3 binding variants are indicated in FIG. 5, for CD3 binding variants in FIG. 7.

Conclusion: Anti leukemic activity initially follows the affinity values on both sides of the bispecific molecule. Highly active and affine to FLT3 is the variant V5. However, surprisingly, the less affine variant V4 has a significant better cytotoxic potential against leukemic cells as the other variants, indicating that for certain applications a lower affinity range for anti-FLT3 antibodies may be selected. A similar result was seen for the CD3 binding part.

T cell activity and Blast cell reduction was analyzed for different antibody concentrations in FIGS. 8 and 9. A PBMC preparation of patient MM2 was obtained and incubated with the indicated concentrations of CC-2 variants. After 5 days T cell activation and depletion of leukemic cells was assessed by flow cytometry (FIG. 8). Nalm16 cells were incubated for 3 days with the indicated concentrations of CC-2 variants at an E:T ratio of 2:1 and were then analyzed by flow cytometry (FIG. 9).

Example 6: Anti Leukemic Activity of ABPs of the Invention In Vivo

In order to test in-vivo application of the CC-2 variants of the invention, preferred variants for FLT3 and CD3 binding were tested for their therapeutic potential in an immune deficient mouse model (FIG. 10). Immunodeficient NSG mice were engrafted with primary AML (left) or ALL (right) cells. On day 7 PBMC together with CC-2 (V4-V6) or control antibody were injected, and bsAb treatment was repeated on day 10. At day 17, leukemic burden (ratio hCD45$^+$/mCD45$^+$ cells) in bone marrow was determined by flow cytometry.

Conclusions: The experiment demonstrates therapeutic potential for even less affine CC2 variants such as V4.

The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the

Example 7: Humanized 4G8 Variants in Monospecific IgG Format

In order to test the superiority of the generated antibody variants of the invention the new variable domain sequences were cloned into a monospecific anti-FLT3 human IgG format. For this, the respective variable heavy and light chain sequences were cloned into a monospecific human IgG format. For this, antibody genes were codon optimized for expression in human cells and designed with NheI and Not restriction sites at the 5' and 3' ends. Genes were synthesized and then cloned into a mammalian expression vector following standard procedures. Following sequence verification plasmids were prepared in sufficient quantity for transfection using Plasmid Plus purification kits (Qiagen).

HEK 293 (human embryonic kidney 293) mammalian cells were passaged to the optimum stage for transient transfection. Cells were transiently transfected with expression vector and cultured for a further 6 days.

Cultures were harvested by centrifugation at 4000 rpm and filtered through a 0.22 mm filter. A first step of purification was performed by Nickel affinity chromatography with elution using PBS containing 400 mM imidazole. A second step of purification was performed by size exclusion chromatography with elution in PBS (phosphate buffered saline) pH7.2. Antibody concentration was determined by UV spectroscopy and the antibodies concentrated as necessary. Antibody purity was determined by SDS-PAGE (sodium dodecyl sulphate polyacrylamide gel electrophoresis) and HPLC (high performance liquid chromatography). HPLC was performed on an Agilent 1100 series instrument using MabPac size exclusion column run in PBS at 0.2 ml/min.

In order to elucidate superiority of generated 4G8 variants a monospecific IgG with the heavy and light chain variable domain sequences of the V4 variant (variable domain heavy and light chain sequences as shown in SEQ ID NOs: 21 and 22 respectively) was compared with the parent (mouse) IgG V6 (variable domain heavy and light chain sequences as shown in SEQ ID NOs: 4 and 8 respectively) and Fc control in an ADCC assay. For this pNKC were generated by incubation of non-plastic adherent PBMCs with K562-41BBL-IL15 feeder cells obtained from St Jude's Children's Research Hospital as described previously (Schmiedel B J et al. Int J Cancer 2011; 128: 2911-2922; Fujisaki H et al. Cancer Res 2009; 69: 4010-4017). BATDA-Europium kills were performed as described previously (Baessler T et al. Cancer Res 2009: 69: 1037-1045). The results are shown in FIG. 11.

The data in FIG. 11 show exemplary results for one pNKC donor at the indicated effector:target ratios. Superior lysis rates for V4 compared to V6 FLT3 monospecific IgG antibody variants could be observed in this experimental setting thus demonstrating improved therapeutic potential of the variants of the invention compared to the parent 4G8 antibody.

The invention claimed is:

1. An Antigen Binding Protein (ABP), wherein the ABP comprises two antibody heavy chain sequences, and two antibody light chain sequences, wherein said antibody heavy chain sequences comprise the amino acid sequence of SEQ ID NO: 21 and the antibody light chain sequences comprise the amino acid sequence of SEQ ID NO: 22.

2. The ABP according to claim 1, wherein the ABP is labelled.

3. The ABP according to claim 1, wherein the ABP is a monoclonal antibody, a fragment of an antibody, or a fragment of a monoclonal antibody.

4. The ABP according to claim 3, wherein said antibody is an IgG, IgE, IgD, IgA, or IgM immunoglobulin.

5. The ABP according to claim 3, which is F(ab')2 antibody fragment.

6. The ABP according to claim 1, wherein said ABP is modified or engineered to increase antibody-dependent cellular cytotoxicity (ADCC), or wherein said ABP is afucosylated.

7. An Antigen Binding Protein (ABP), wherein the ABP is bispecific, comprising
   a. an FLT-3 antigen binding domain comprising two antibody heavy chain sequences and two antibody light chain sequences, wherein said antibody heavy chain sequences comprise the amino acid sequence of SEQ ID NO: 34 and the antibody light chain sequences comprise the amino acid sequence of SEQ ID NO: 35, and
   b. a second antigen binding domain.

8. The ABP of claim 7, wherein the second antigen binding domain comprises an UCHT1 anti-CD3 scFv comprising the amino acid sequence of SEQ ID NO: 14.

9. An isolated nucleic acid comprising a sequence encoding for the ABP of claim 1.

10. A nucleic acid construct (NAC) comprising the nucleic acid of claim 9 and one or more additional sequence features permitting the expression of the ABP in a cell.

11. A recombinant host cell comprising the nucleic acid of claim 9.

* * * * *